United States Patent [19]

Boswell et al.

[11] Patent Number: 5,512,681

[45] Date of Patent: Apr. 30, 1996

[54] ANGIOTENSIN II RECEPTOR BLOCKING IMIDAZOLINONE DERIVATIVES

[75] Inventors: George A. Boswell; Indawati DeLucca, both of Wilmington; Mimi L. Quan, Newark, all of Del.

[73] Assignee: E. I. Du Pont de Nemours and Company, Wilmington, Del.

[21] Appl. No.: 128,784

[22] Filed: Sep. 30, 1993

Related U.S. Application Data

[63] Continuation-in-part of Ser. No. 929,455, Aug. 14, 1992, abandoned, which is a continuation-in-part of Ser. No. 747,023, Aug. 19, 1991, abandoned.

[51] Int. Cl.⁶ .................... C07D 231/06; C07D 403/10; A61K 31/41; A61K 31/415
[52] U.S. Cl. ................. 548/300.7; 548/251; 548/253; 548/266.2; 548/260
[58] Field of Search .................. 548/300.7, 251, 548/253, 266.2, 260; 514/359, 383, 381, 382, 396, 397

[56] References Cited

FOREIGN PATENT DOCUMENTS

| | | |
|---|---|---|
| 0407342A2 | 6/1990 | European Pat. Off. . |
| 0419048A | 3/1991 | European Pat. Off. . |
| 0412594A | 7/1991 | European Pat. Off. . |
| 0475898A1 | 9/1991 | European Pat. Off. . |
| WO91/14679 | 3/1991 | WIPO . |

*Primary Examiner*—David B. Springer

[57] ABSTRACT

Novel imidazolinone derivatives of formula (I), which are useful as angiotensin II antagonists, are disclosed:

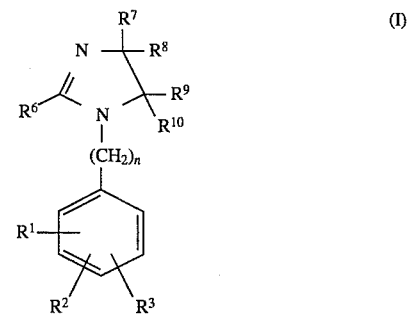

11 Claims, No Drawings

ANGIOTENSIN II RECEPTOR BLOCKING IMIDAZOLINONE DERIVATIVES

CROSS-REFERENCE TO RELATED APPLICATION

This application is a continuation-in-part of application Ser. No. 07/929,455, filed Aug. 14, 1992, now abandoned which is a continuation-in-part of application Ser. No. 07/747,023, filed Aug. 19, 1991, now abandoned.

BACKGROUND OF THE INVENTION

1. Field of the Invention

This invention relates to novel substituted imidazolinone derivatives. The invention also relates to pharmaceutical compositions containing the novel imidazolinone derivatives and pharmaceutical methods using them, alone and in conjugation with other drugs.

The compounds of this invention inhibit the action of the hormone angiotensin II(AII) and are useful therefore in alleviating angiotensin induced hypertension. The enzyme renin acts on a blood plasma α2-globulin, angiotensinogen, to produce angiotensin I, which is then converted by ACE to AII. The latter substance is a powerful vasopressor agent which has been implicated as a causative agent for producing high blood pressure in various mammalian species, such as the rat, dog, and man. The compounds of this invention inhibit the action of AII at its receptors on target cells and thus prevent the increase in blood pressure produced by this hormone-receptor interaction. By administering a compound of this invention to a species of mammal with hypertension due to AII, the blood pressure is reduced. The compounds of this invention are also useful for the treatment of congestive heart failure. Administration of a compound of this invention with a diuretic such as furosemide or hydrochlorothiazide, either as a stepwise combined therapy (diuretic first) or as a physical mixture, enhances the antihypertensive effect of the compound. Administration of a compound of this invention with a NSAID can prevent renal failure which sometimes results from administration of a NSAID.

Several peptide analogs of AII are known to inhibit the effects of this hormone by competitively blocking the receptors, but their experimental and clinical applications have been limited by the partial agonist activity and lack of oral absorption (M. Antonaccio, Clin. Exp. Hypertens., 1982, A4, 27–46; D. H. P. Streeten and G. H. Anderson, Jr., Handbook of Hypertension. Clinical Pharmacology of Antihypertensive Drugs, ed., A. E. Doyle, Vol. 5, pp. 246–271, Elsevier Science Publisher, Amsterdam, The Netherlands, 1984).

Several non-peptide antagonists of AII have been disclosed. These compounds are covered by U.S. Pat. Nos. 4,207,324; 4,340,598; 4,576,958; 4,582,847; and 4,880,804; in European Patent Applications 028,834; 245,637; 253,310; and 291,969; and in articles by A. T. Chiu et at. (Eur. J. Pharm. Exp. Therap., 1988, 157, 13–21) and by P. C. Wong et at. (J. Pharm. Exp. Therap., 1988, 247, 1–7). All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo [4,5-c]pyridine-6-carboxylic acid and analogs thereof as antihypertensive agents, specifically $Ca^{2+}$ channel blockers.

L. Chang et al., in EP 0 412 594 A (filed Jul. 23, 1990) disclose substituted triazolinones, triazolinethiones, and triazolinimines of the formula:

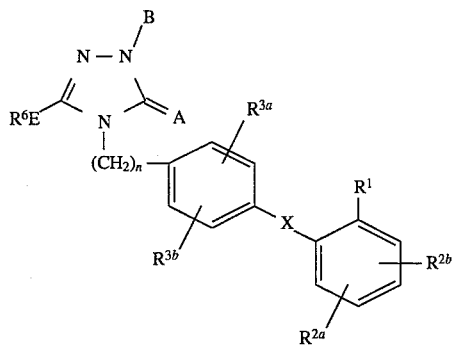

These are claimed to be antagonists of AII which are useful for treating hypertension, congestive heart failure (CHF), and elevated intraocular pressure.

C. Bernhart et al., in WO 91/14679 (published Oct. 3, 1991 )disclose heterocyclic N-substituted derivatives of the formula

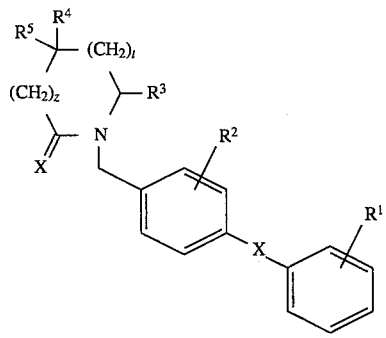

These compounds are disclosed to be antagonists of AII which are useful for treating cardiovascular disorders such as hypertension.

F. Ostermeyer et al., in EP 475,898 (published Mar. 18, 1992) disclose heterocyclic N-substituted derivatives of formula

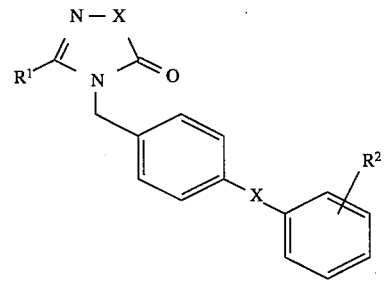

These compounds are disclosed to be antagonists of AII which are useful for treating cardiovascular disorders such as hypertension.

Wagner et al., in EP 0 503 162 (published Sep. 16, 1992) disclose azole derivatives of the general Formula (A) and the specific compound Example 150.

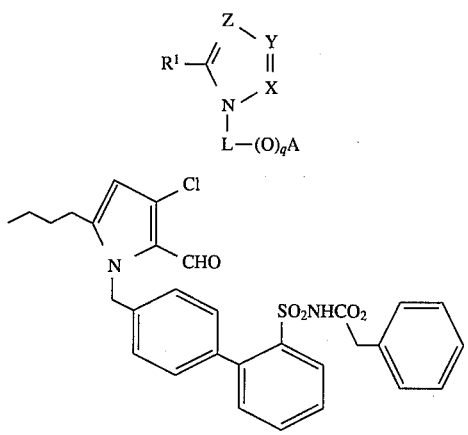

Formula (A)

Example 150

These compounds are disclosed to be antagonists of AII which are useful for treating cardiovascular disorders such as hypertension.

P. Herold and P. Buhlmayer in EP 0 407 342 A2 disclose substituted pyrimidinones, pyrimidinethiones, and pyrimidinimines of the formula:

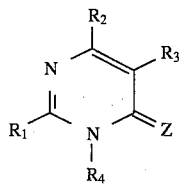

These are claimed to be antagonists of AII which are useful for treating hypertension.

E. Allen et al. in EP 0 419 048 A (filed Aug. 21, 1990) disclose a similar series of pyrimidinones which are claimed to be antagonists of AII useful for the treatment of CHF and elevated intraocular pressure.

SUMMARY OF THE INVENTION

The present invention provides novel angiotensin II receptor antagonists of formula (I), pharmaceutical compositions containing compounds of formula (I) and therapeutic methods using them wherein:

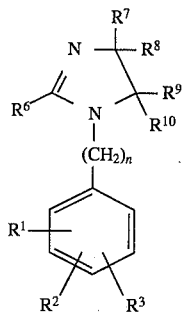

(I)

$R^1$ is other than in the ortho position and is:

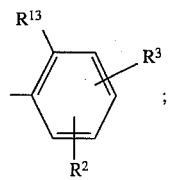

$R^2$ is
(a) H,
(b) halo (F, Cl, Br, I),
(c) $C_1$–$C_4$ alkyl,
(d) $C_1$–$C_4$ alkoxy,
(e) $C_1$–$C_4$ acyloxy,
(f) $C_1$–$C_4$ alkylthio,
(g) $C_1$–$C_4$ alkylsulfinyl,
(h) $C_1$–$C_4$ alkylsulfonyl,
(i) hydroxy ($C_1$–$C_4$) alkyl,
(j) aryl ($C_1$–$C_4$) alkyl,
(k) —$CO_2H$,
(l) —CN,
(m) —$CONHOR^{12}$,
(n) —$SO_2NHR^{21}$,
(o) —$NH_2$,
(p) $C_1$–$C_4$ alkylamino,
(q) $C_1$–$C_4$ dialkylamino,
(r) —$NHSO_2R^{20}$,
(s) —$NO_2$,
(t) furyl,
(u) aryl;

$R^3$ is
(a) H,
(b) halo,
(c) $C_1$–$C_4$ alkyl,
(d) $C_1$–$C_4$ alkoxy,
(e) $C_1$–$C_4$ alkoxyalkyl;

$R^4$ is
(a) —CN,
(b) —$NO_2$,
(c) —$CO_2R^{11}$;

$R^5$ is
(a) H,
(b) $C_1$–$C_6$ allyl,
(c) $C_3$–$C_6$ cycloalkyl,
(d) $C_2$–$C_4$ alkenyl,
(e) $C_2$–$C_4$ alkynyl;

$R^6$ is
(a) $C_1$–$C_{10}$ alkyl,
(b) $C_3$–$C_8$ alkenyl,
(c) $C_3$–$C_8$ alkynyl,
(d) $C_3$–$C_8$ cycloalkyl,
(e) $C_4$–$C_8$ cycloalkenyl,
(f) $C_4$–$C_{10}$ cycloalkylalkyl,
(g) $C_5$–$C_{10}$ cycloalkylalkenyl,
(h) $C_5$–$C_{10}$ cydoalkylalkynyl,
(i) —$(CH_2)_sZ(CH_2)_mR^5$,
(j) phenyl, optionally substituted with 1–2 substituents selected from the group of halo, $C_1$–$C_4$ alkyl, $C_1$–$C_4$ alkoxy, —$NO_2$, —$NH_2$, —OH and benzyloxy,
(k) benzyl, optionally substituted on the phenyl ring with 1–2 substituents selected from the group of halo, $C_1$–$C_4$ alkyl, $C_1$–$C_4$ alkoxy and —$NO_2$;

$R^7$, $R^8$, $R^9$, and $R^{10}$ are independently chosen from
(a) H,
(b) $C_1$–$C_8$ alkyl, (c) $C_1-C_8$ perfluoroalkyl,
(d) $C_3-C_6$ cycloalkyl,
(e) $-NO_2$,
(f) $-CN$,
(g) $-CONR^{15}R^{16}$
(h) $-CO_2R^{17}$,
(i) $-OR^{18}$
(j) $-(CH_2)_nCONR^{15}R^{16}$ where n is 1–4,
(k) $-(CH_2)_nCO_2R^{17}$ where n is 1–4,
(l) $(CH_2)_nOR^{18}$ where n is 1–4,
(m) aryl, wherein aryl is as defined above
(n) $-CH_2$ aryl, wherein aryl is as defined above,
(o) $R^7$ and $R^8$ taken together are $-(CH_2)_t-$, or $-(CH_2)_mX(CH_2)_q-$
(p) $R^9$ and $R^{10}$ taken together can be S or O;

$R^{11}$ is
(a) H,
(b) $C_1-C_4$ alkyl,
(c) $C_1-C_4$ cycloalkyl,
(d) phenyl,
(e) benzyl;

$R^{12}$ is
(a) H,
(b) methyl,
(c) benzyl;

$R^{13}$ is
(a) $-CH_2CO_2H$,
(b) $-C(CF_3)_2OH$,
(c) $-CONHNHSO_2CF_3$,
(d) $-CONHOR^{12}$,
(e) $-CONHSO_2R^{20}$,
(f) $-CONHSO_2NHR^{19}$,
(g) $-C(OH)R^{19}PO_3H_2$,
(h) $-NHCONHSO_2R^{20}$,
(i) $-NHPO_3H_2$
(j) $-SO_2NHCOR^{20}$,
(k) $-OPO_3H_2$,
(l) $-OSO_3H$,
(m) $-PO(OH)R^{19}$,
(n) $-PO_3H_2$,
(o) $-SO_3H$,
(p) $-SO_2NHR^{19}$,
(q) $-NHSO_2NHCOR^{20}$,
(r) $-SO_2NHCONHR^{19}$, (s) 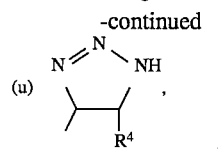

(t) 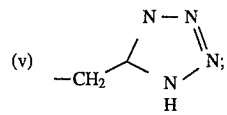

(u)

(v) 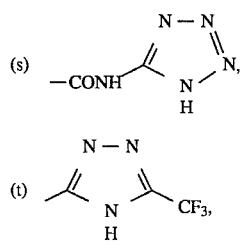

$R^{14}$ is
(a) H,
(b) $C_1-C_6$ alkyl,
(c) aryl,
(d) benzyl,
(e) $COR^{11}$,
(f) $CONHR^{11}$;

$R^{15}$ and $R^{16}$ are independently
(a) H,
(b) $C_1-C_6$ alkyl,
(c) aryl,
(d) aryl $(C_1-C_4)$ alkyl,
or when taken together constitute a
(e) piperidine ring,
(f) morpholine ring,
(g) piperazine ring, optionally N-substituted with $C_1-C_6$ alkyl, phenyl or benzyl;

$R^{17}$ is
(a) H,
(b) $C_1-C_6$ alkyl,
(c) phenyl,
(d) benzyl;

$R^{18}$ is
(a) H,
(b) $C_1-C_6$ alkyl,
(c) phenyl,
(d) benzyl;

$R^{19}$ is
(a) H,
(b) $C_1-C_5$ alkyl optionally substituted with a substituent selected from the group consisting of aryl, heteroaryl, $-OH$, $-SH$, $C_1-C_4$ alkyl, $C_1-C_4$ alkoxy, $C_1-C_4$ alkylthio, $-CF_3$, halo, $-NO_2$, $-CO_2H$, $-CO_2CH_3$, $-CO_2$-benzyl, $-NH_2$, $C_1-C_4$ alkylamino, $C_{1-4}$ dialkylamino, $-PO_3H_2$,
(c) aryl,
(d) $-CH_2$ aryl,
(e) heteroaryl, $R^{20}$ is
(a) aryl,
(b) $C_3-C_7$ cycloalkyl,
(c) $C_1-C_4$ perfluoroalkyl,
(d) $C_1-C_4$ alkyl optionally substituted with a substituent selected from the group consisting of aryl, heteroaryl, $-OH$, $-SH$, $C_1-C_4$ alkyl, $C_1-C_4$ alkoxy, $C_1-C_4$ alkylthio, $-CF_3$, halo, $-NO_2$, $-CO_2H$, $-CO_2CH_3$, $-CO_2$-benzyl, $-NH_2$, $C_1-C_4$ alkylamino, $C_1-C_4$ dialkylamino, $-PO_3H_2$,
(e) $C_1-C_4$ alkoxy optionally substituted with a substituent selected from the group consisting of aryl, heteroaryl, $-OH$, $-SH$, $C_1-C_4$ alkyl, $C_1-C_4$ alkoxy, $C_1-C_4$ alkylthio, $-CF_3$, halo, $-NO_2$, $-CO_2H$, $-CO_2CH_3$, $-CO_2$-benzyl, $-NH_2$, $C_1-C_4$ alkylamino, $C_1-C_4$ dialkylamino, $-PO_3H_2$, or
(f) heteroaryl, where heteroaryl is as defined above;

$R^{21}$ is (a) H,
(b) $C_1$–$C_6$ alkyl,
(c) phenyl,
(d) benzyl,

X is
(a) —S—,
(b) —O—,
(c) —SO—,
(d) —$SO_2$—,
(e) —$CHR^{14}$—,
(f) —$NR^{14}$—;

Z is
(a) —O—,
(b) —S—,
(c) —$NR^{11}$— m is 1 to 5;
n is 1 to 4;
q is 1 to 5;
t is 2 to 5;
or a pharmaceutically acceptable salt thereof.

Preferred compounds of tiffs invention are those of formula (I) wherein $R^1$ is in the para position and is

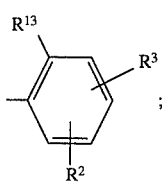

$R^6$ is
(a) $C_1$–$C_{10}$ alkyl,
(b) $C_3$–$C_{10}$ alkenyl,
(c) $C_3$–$C_{10}$ alkynyl,
(d) $C_3$–$C_8$ cycloalkyl,
(e) phenyl, optionally substituted with 1–2 substituents selected from the group of halo, $C_1$–$C_4$ alkyl, $C_1$–$C_4$ alkoxy, —$NO_2$, —$NH_2$, —OH and benzyloxy,
(f) benzyl, optionally substituted on the phenyl ring with one or two substituents selected from the group consisting of halo, $C_1$–$C_4$ alkyl, $C_1$–$C_4$ alkoxy and —$NO_2$;

$R^7$, $R^8$, $R^9$, $R^{10}$ are independently
(a) H,
(b) $C_1$–$C_4$ alkyl,
(c) $C_1$–$C_4$ perfluoroalkyl,
(d) $C_3$–$C_6$ cycloalkyl,
(e) phenyl, optionally substituted with one or two substituents selected from the group of halo, $C_1$–$C_3$ alkyl, $C_1$–$C_3$ alkoxy, $NO_2$, $CF_3$, $NH_2$, and OH,
(f) $R^7$ and $R^8$ taken together are —$(CH_2)_t$—, or —$(CH_2)_m X(CH_2)_q$—,
(g) $R^9$ and $R^{10}$ taken together can be S or O;

$R^{13}$ is
(a) —$CONHSO_2R^{20}$,
(b) —$NHCONHSO_2R^{20}$,
(c) —$HSO_2NHCOR^{20}$,
(d) —$PO_3H_2$,
(e) —$SO_3H$,
(f) —$SO_2NHR^{19}$,
(g) —$SO_2NHCOR^{20}$,
(h) —$SO_2NHCONHR^{19}$, (i) 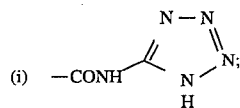

or a pharmaceutically acceptable salt thereof.

Still more preferred are compounds of the above preferred scope formula (I) wherein
$R^6$ is
(a) $C_{1-7}$ alkyl,
(b) $C_3$–$C_4$ alkenyl,
(c) $C_3$–$C_4$ alkynyl,
(d) phenyl, optionally substituted with 1–2 substituents selected from the group of halo, $C_1$–$C_4$ alkyl, $C_1$–$C_4$ alkoxy, —$NO_2$, —$NH_2$, —OH and benzyloxy;

$R^{13}$ is
(a) —$CONHSO_2R^{20}$,
(b) —$NHCONHSO_2R^{20}$,
(c) —$NHSO_2NHCOR^{20}$,
(d) —$SO_2NHR^{19}$,
(e) —$SO_2NHCOR^{20}$,
(f) —$SO_2NHCONHR^{19}$;

or a pharmaceutically acceptable salt thereof.

Most preferred due to their activity as angiotensin II antagonists are compounds of the more preferred scope wherein
$R^1$ is

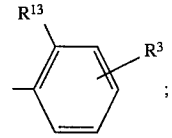

or a pharmaceutically acceptable salt thereof.

Illustrative of the most preferred compounds of the invention are the following:

N-[4'-[[4-oxo-2-propyl-8-thia-1,3-diazaspiro[4.5]dec-1-en-3 -yl]methyl](1,1'-biphenyl-2-ylsulfonyl)]-benzamide N-[4'-[[4-oxo-2-propyl-1,3-diazaspiro[4.4 ]non-1-en-3-yl]methyl](1,1'-biphenyl-2-ylsulfonyl)]-benzamide N-[4'-[[4-oxo-2-butyl-1,3-diazaspiro[4.4]non-1-en-3 -yl] methyl](1,1'-biphenyl-2-ylsulfonyl)]-benzamide N-[4'-[[4,5-dihydro-4,4-dimethyl-5-oxo-2-propyl-1H-imidazol-1-yl]methyl](1,1'-biphenyl-2-ylsulfonyl)]-benzamide N-[4'-[[4,5-dihydro-4,4-dimethyl-5-oxo-2-propyl-1H-imidazol-1 -yl]methyl](1,1-biphenyl-2-ylsulfonyl )]-4-chlorobenzamide N-[4'-[[4-oxo-2-propyl-8-thia-1,3-diazaspiro[4.5]dec-1-en-3 -yl]methyl](1,1'-biphenyl-2-ylsulfonyl)]-hexanamide N-[4'-[[4-oxo-2-propyl-1,3-diazaspiro[2.4]hept-1-en-3-yl]methyl](1,1' -biphenyl-2-ylsulfonyl)]-hexanamide N-[4'-[[4-oxo-2-propyl-1,3-diazaspiro[4.4]non-1-en-3-yl]methyl](1,1' -biphenyl- 2-ylsulfonyl )]-hexanamide N-[4'-[[4-oxo-2-propyl-1,3-diazaspiro[4.5]dec-1-en-3-yl]methyl](1,1' -biphenyl-2-ylsulfonyl)]-hexanamide N-[4'-[[4-oxo-2-butyl-1,3-diazaspiro[4.4]non-1-en-3-yl] methyl](1,1' -biphenyl-2-ylsulfonyl)]-hexanamide N-[4'-[[4,5-dihydro-4,4-dimethyl-5-oxo-2-propyl-1H-imidazol-1 -yl]methyl]( 1,1'-biphenyl-2-ylsulfonyl)]-hexanamide N-[4'-[[4,5-dihydro-4,4-dicyclopropyl-5-oxo-2-propyl-1H-imidazol-1 -yl]methyl](1,1'-biphenyl-2-ylsulfonyl)]-hexanamide N-[4'-[[4,5-dihydro-4,4-bistrifluoromethyl-5-oxo-2-propyl-1H-imidazol-1 -yl]methyl](1,1'-biphenyl-2-ylsulfonyl)]-hexanamide N-[4'-[[4,5-dihydro-4,4-dimethyl-5-oxo-2-propyl-1H-imidazol-1 -yl]methyl][3'-methyl(1,1-biphenyl-2-ylsulfonyl)]]-hexanamide N-[4'-[[4,5-dihydro-4,4-dimethyl-5-oxo-2-propyl-1H-imidazol-1 -yl]methyl][4-propyl(1,1'-biphenyl-2-ylsulfonyl)]]-hexanamide N-[4'-[[4,5-dihydro-4,4-dimethyl-5-oxo-2-propyl-1H-imidazol-1 -yl]methyl](1,1-biphenyl-2-ylsulfonyl)]-trifluoroacetamide 3,5-dihydro-5,5-dimethyl-2-propyl-3-[(2' -(N((phenylsulfonyl)carboxamido)biphen-4-yl)methyl]-4H-imidazol-4-one N-[4'-[[4-oxo-8-benzyl-2-propyl-1,3,8-triazaspiro[4.5]dec-1-en-3-yl]methyl](1,1'-biphenyl-2-ylsulfonyl)]-carbamic acid, phenethyl ester N-[4'-[[8-benzoyl-4-oxo-2-propyl-1,3,8-triazaspiro[4.5]dec-1-en-3 -yl]methyl](1,1'-biphenyl-2-ylsulfonyl)]-carbamic acid, n-butyl ester N-[4'-[[8-benzoyl-4-oxo-2-propyl- 1,3,8-triazaspiro[4.5]dec-1-en-3 -yl]methyl][3'-fluoro-(1,1'-biphenyl-2-ylsulfonyl)]]-carbamic acid, n-butyl ester N-[4'-[[8-benzoyl-4-oxo-2-propyl-1,3,8-triazaspiro[4.5]dec-1-en-3 -yl]methyl][3'-chloro-(1,1'-biphenyl-2-ylsulfonyl )]]-carbamic acid, n-butyl ester N-[4'-[[8-acetyl-4-oxo-2-propyl-1,3,8-triazaspiro[4.5]dec-1-en-3 -yl]methyl][3'-methyl-(1,1'-biphenyl-2-ylsulfonyl )]]-carbamic acid, n-butyl ester N-4'-[[4-oxo-2-propyl-8-oxa- 1,3-diazaspiro[4.5]dec-1-en-3 -yl]methyl](1,1'-biphenyl-2-ylsulfonyl)]-carbamic acid, phenethyl ester N-[4'-[[4-oxo-2-propyl-8-oxa-1,3-diazaspiro[4.5]dec-1-en-3 -yl]methyl][(3'-fluoro-(1,1'-biphenyl-2-ylsulfonyl)]]-carbamic acid, phenethyl ester N-[4'-[[4-oxo-2-propyl-8-oxa-1,3-diazaspiro[4.5]dec-1-en-3 -yl]methyl](1,1'-biphenyl-2-ylsulfonyl)]-carbamic acid, phenethyl ester N-[4'-[[4-oxo-2-propyl-1,3-diazaspiro[4.4]non-1-en-3 -yl]methyl][(3'-chloro-(1,1'-biphenyl-2-ylsulfonyl)]]-carbamic acid, n-butyl ester N-[4'-[[4-oxo-2-propyl-8-oxa-1,3-diazaspiro[4.5]dec-1-en-3 -yl]methyl][(3'-methyl-(1,1'-biphenyl-2-ylsulfonyl)]]-carbamic acid, phenethyl ester N-[4'-[[4-oxo-2-propyl-1,3-diazaspiro[4.4]non-1-en-3-yl] methyl](1,1' -biphenyl-2-ylsulfonyl)]-carbamic acid, 2-methylpropyl ester N-[4'-[[4-oxo-2-propyl-1,3-diazaspiro[4.4]non-1-en-3-yl] methyl][3' -methyl(1,1'-biphenyl-2-ylsulfonyl)]]-carbamic acid, n-butyl ester N-[4'-[[4-oxo-2-propyl-1,3-diazaspiro[4.4]non-1-en-3 -yl]methyl][4propyl(1,1'-biphenyl-2-ylsulfonyl)]]-carbamic acid, n-butyl ester Note that throughout the text when an alkyl substituent is mentioned, the normal alkyl structure is meant (e.g., butyl is n-butyl) unless otherwise specified. However, in the definition of radicals above (e.g., $R^6$), both branched and straight chains are included in the scope of alkyl, alkenyl and alkynyl.

The term aryl, as used herein, is meant to include phenyl optionally substituted with one to three substituents selected from the group consisting of —OH, —SH, $C_1$–$C_4$-alkyl, $C_1$–$C_4$-alkoxy, —CF$_3$, halo, —NO$_2$, —CO$_2$H, —CO$_2$CH$_3$, —CO$_2$-benzyl, —NH$_2$, —NH($C_1$–$C_4$-alkyl), —N ($C_1$–$C_4$-alkyl)$_2$.

The term heteroaryl, as used herein, is meant to include unsubstituted, monosubstituted or disubstituted 5- to 10-membered mono- or bicyclic aromatic rings which can optionally contain from 1 to 3 heteroatoms selected from the group consisting of O, N, and S. Included in the definition of the group heteroaryl, but not limited to, are the following: pyridyl, pyridazinyl, pyrimidinyl, pyrazinyl, 1,3,5-triazinyl, furyl, thiophenyl, imidazolyl, oxazolyl, thiazolyl, benzofuranyl, benzothiophenyl, benzhnidazolyl, benzoxazolyl, benzothiazolyl, indolin-2-onyl, indolinyl, indolyl, pyrrolyl, quinonlinyl mad isoquinolinyl. Particularly preferred are 2-, 3-, or 4-pyridyl; 2- or 3-furyl; 2- or 3-thiphenyl; 2-, 3-, or 4-quinolinyl; or 1-, 3-, or 4-isoquinolinyl optionally substituted with one to three substituents selected from the group consisting of —OH, —SH, $C_1$–$C_4$-alkyl, $C_1$–$C_4$-alkoxy, —CF3, halo, —NO$_2$, —CO$_2$H, —CO$_2$CH$_3$, —CO$_2$-benzyl, —NH$_2$, —NH($C_1$–$C_4$-alkyl), —N($C_1$–$C_4$-alkyl)$_2$.

Pharmaceutically suitable salts include both the metallic (inorganic) salts and organic salts; a list of which is given in Remington's Pharmaceutical Sciences, 17th Edition, p. 1418 (1985). It is well known to one skilled in the art that an appropriate salt form is chosen based on physical and chemical stability, flowability, hydroscopicity, and solubility. Preferred salts of this invention for reasons cited above include potassium, sodium, calcium, and ammonium salts.

DETAILED DESCRIPTION

Synthesis

The compounds of formula (I) may be prepared using the reactions and techniques described in this section. The reactions are performed in solvent suitable to the reagents and materials employed and suitable for the transformation being effected. It is understood by those skilled in the an of organic synthesis that the functionality present on the imidazole and other portions of the molecule must be consistent with the chemical transformations proposed. This will frequently necessitate judgment as to the order of synthetic steps, protecting groups required, deprotection conditions and activation of a benzylic position to enable attachment to nitrogen on the imidazole nucleus. Throughout the following section, not all compounds of formula (I) falling into a given class may necessarily be prepared by all the methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used. The compounds of this application that have a chiral center may be resolved into the pure or partially pure optical isomers by any of the appropriate procedures known to those skilled in the art.

The compounds of the present invention can be prepared by reaction of a sulfonamide of formula (2) with an acylating reagent such as an acyl halide or acyl imidazole, or an alkyl chroroformate, or a carbamoylating reagent such as an isocyanate, (Scheme 1). Alcohol exchange can also be performed on compounds of formula (4) by heating with excess of the desired alcohol to give new compounds within the present invention. The sulfonamides 2 can be prepared as described in European Application EP 479,479, which is hereby incorporated by reference, and as shown in Scheme 2.

SCHEME 1

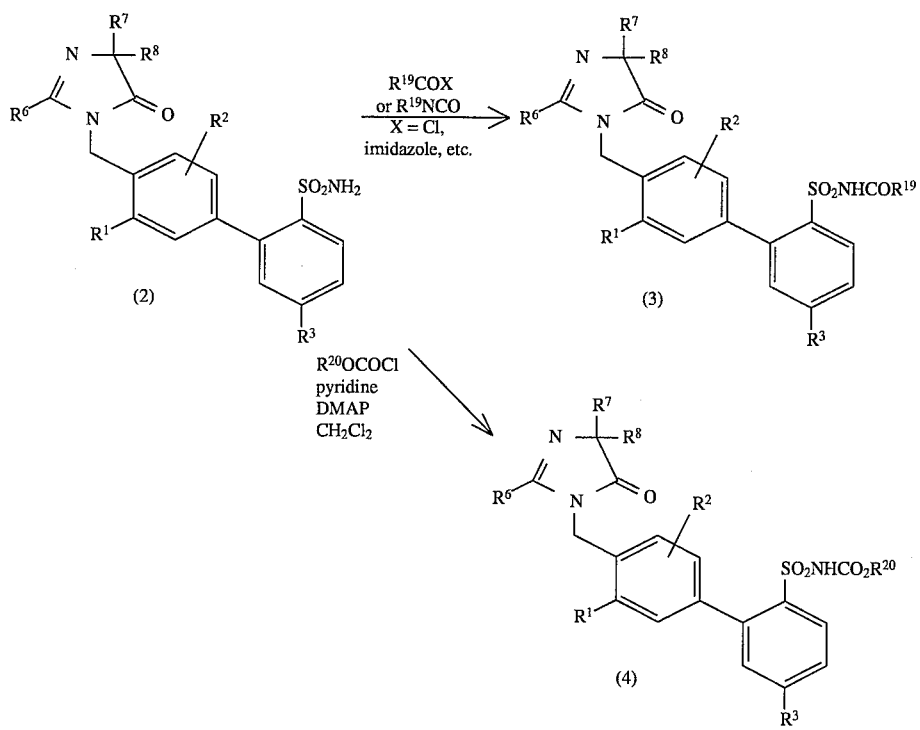

The alkylation produces a mixture of the two regioisomers using ether sodium hydride or potassium carbonate as base. The $N^1$ regioisomer is the major and the $N^3$ is the minor products. These two isomers can be separated and purified using conventional separation techniques such as chromatography or crystallization. In those cases where separation of regioisomers is difficult by conventional techniques, the mixture can be transformed into suitable derivatives that can be separated by usual separation methods. They possess distinct physical and biological properties.

SCHEME 2

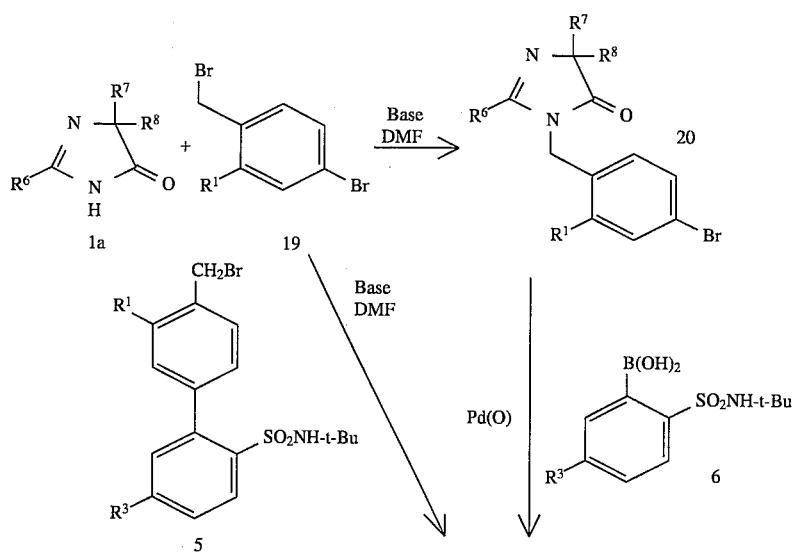

-continued
SCHEME 2

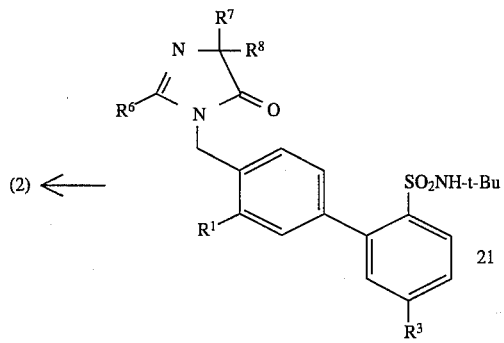

The biphenyl intermediates of formula (5) can be prepared as described in European Patent Application EP 479,479 and references therein, or as shown in Scheme 3. The boronic acid 6 may be prepared by lithiation of sulfonamide 7, followed by treatment with triisopropyl borate and hydrolysis as shown in Scheme 3.

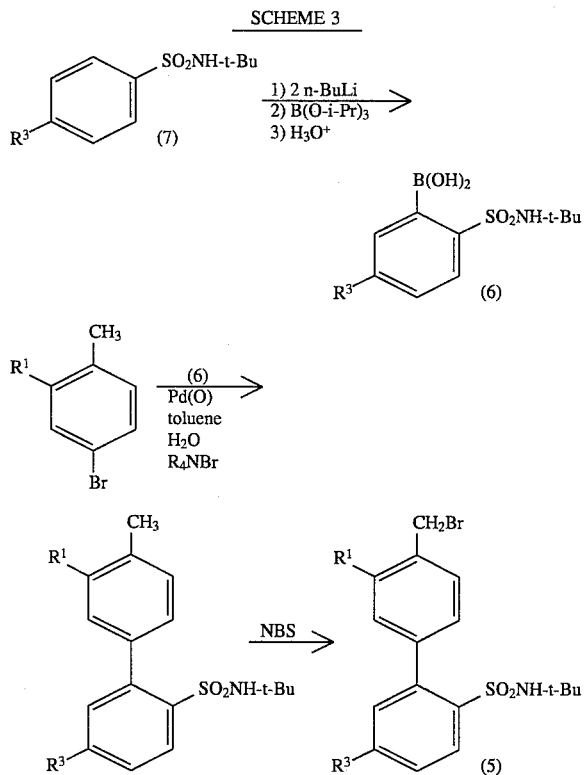

The starting imidazolinones are readily available by any number of standard methods. For example, imidazolinone of formula (1) can be prepared as shown in Scheme 4. The amino nitrile 3 is readily obtainable from aldehydes and ketones via the Strecker Synthesis and various modifications thereof ($R^7=R^8=CF_3$, Y. V. Zeifman, N. P. Gambaryan, I. L. Knunyants, *Dokl. Acad. Nauk. S.S.S.R.*, 153, 1334, 1963). Treatment of the amino nitrite with triethyl amine and one equivalent of the appropriate acyl or aroyl chloride 8 in methylene chloride at room temperature overnight, gives the corresponding amidonitrile 9. Alternatively, the nitrite can be made following the procedure described in German patent disclosure DE3704100A1. The nitrile can be hydrolyzed to the diamide 10 using standard procedures such as treatment with hydrochloric acid followed by ammonium hydroxide. Treatment of the diamide with 1 sodium hydroxide as described in E. Mohr, *J. Pract. Chem.*, 81, 49, (1910), gives the imidazolinone 1.

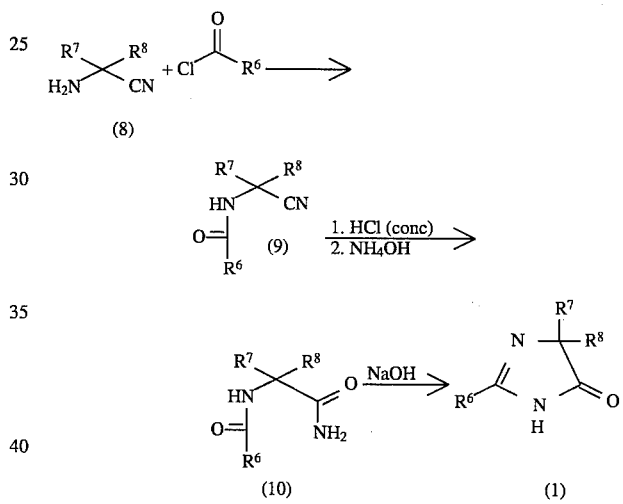

Alternatively, imidazolinones of formula(1) can also be prepared as shown in Scheme 5. Treatment of the amino acid 11 with tert-butyl pyrocarbonate 12 with two or more equivalents of base gives the BOC (tert-butyloxycarbonyl) protected amino acid 13, M. Bodanszky and A. Bodanszky, *The Practice of Peptide Chemistry*, 1984. The protected amino amide 14 can be synthesized from the active ester followed by treatment with ammonia. Deprotection using HCl gas gives the amino amide hydrochloride 11a. Treatment with two or more equivalents of base and the appropriate acyl or aroyl chloride gives the diamide 10 which can be cyclized by treatment with 1N sodium hydroxide as described above. Likewise, compound 10 may be obtained by reacting amino acid with the requisite acid chloride by either a Schotten-Baumann procedure, or simply stirring in a solvent such as methylene chloride in the presence of base such as sodium bicarbonate, pyridine or triethyl amine followed by coupling reaction with ammonia via a variety of amide or peptide forming reactions such as DCC coupling, azide coupling, mixed anhydride synthesis or any other coupling procedure familiar to one skilled in the art.

The use of 1-amino-1-cycloalkylcarboxylic acids in the above procedure provides the imidazolinone starting materials for the preparation of the spiro-substituted imidazolinones of formula (I).

SCHEME 5

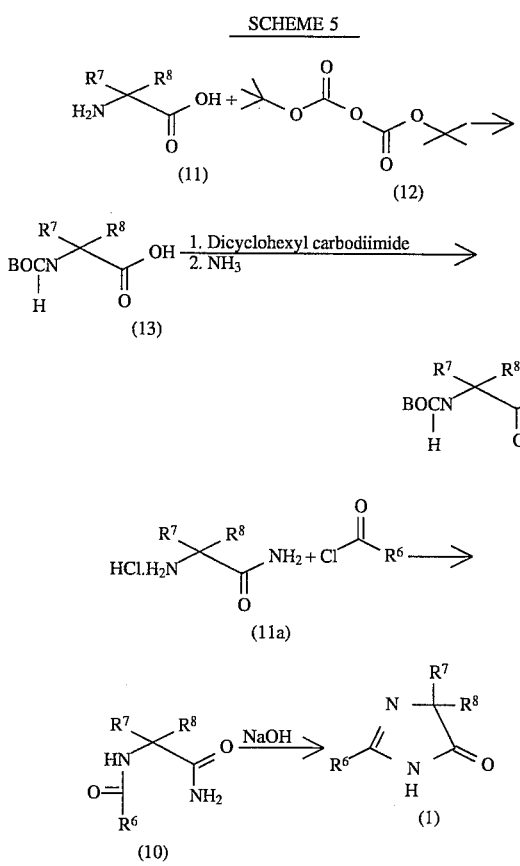

Imidazolinones of formula (1) can also be prepared following the procedure described in Japanese Patent disclosure JP 58055467, and the procedure by H. Lehr, J. Am. Chem. Soc., 75, 3640, 1953 and references therein.

Imidazolinones of formula (1) wherein $R^7$ an $R^8$ are both phenyl can be prepared as shown in Scheme 6 by reaction of benzil 15 with alkyl or aryl amidine hydrochloride 16. A. W. Cox, Org. Syn., 1, 5, R. T. Boere, R. T. Oakley, R. W. Reed, J. Organomet. Chem., 331, 161 (1987) in the presence of base such as 1N sodium hydroxide, G. Rio and A. Rajon, Bull. Soc. Chim. France, 543 (1958) and references therein.

SCHEME 6

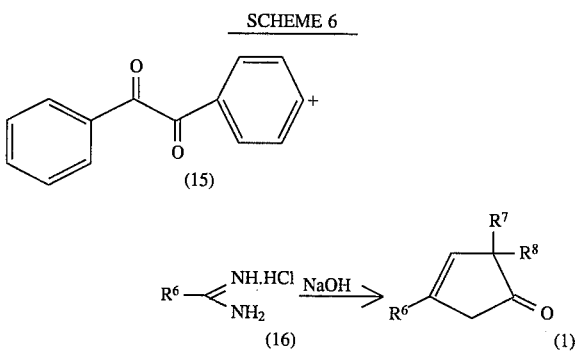

The imidazoline thiones of formula (18) can be prepared by treatment of the requisite alkylated imidazolinone 17 with Lawesson's reagent or phosphorus pentasulfide as described in M. P. Cava and M. I. Levinson, Tetrahedron, 41, 5061, 1985 (Scheme 7).

SCHEME 7

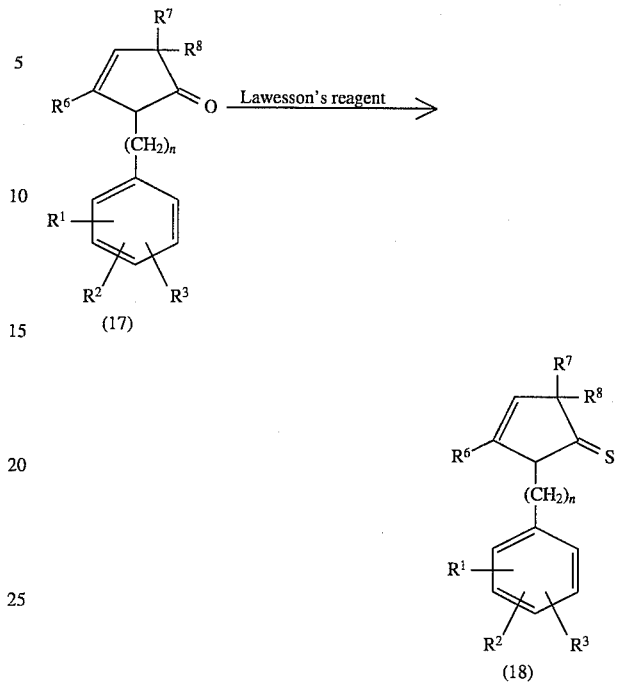

The compounds of this invention and their preparation can be understood further by the following examples which do not constitute a limitation of the invention. In these examples, unless otherwise indicated, all temperatures are in degrees centigrade and parts and percentages are by weight.

EXAMPLE 1

N-((4'-oxo-2-propyl-8-thia-1,3-diazaspiro-((4.5))dec-1-en-3-yl-methyl))((1,1'-biphenyl))-2-ylsulfonyl))-benzamide PART A: Preparation of 4-amino-4-cyanotetrahydrothiopyrane Sodium cyanide (2.11 g, 43 mmol) was dissolved in water (40 mL). Ammonium chloride (2.53 g, 47.3 mmol) was added followed by a solution of tetrahydrothiopyran-4-one (5.0 g, 43 mmol) in methanol (40 mL). The mixture was stirred at room temperature under $N_2$ overnight. The mixture was diluted with $H_2O$ and extracted with methylene chloride. The combined organic layer was washed with brine, dried over $MgSO_4$ and concentrated. The residue was chromatographed on silica gel eluting with hexane-ethyl acetate (1:1) to give 5.28 g of white solid (86%). MS m/e 143.0 (M+H)+; $^1$HNMR (CDCl$_3$/FMS) δ1.60–2.00 (m, 4H, CH$_2$), 2.25 (d, 2H, CH$_2$), 2.62–3.00 (m, 4H, CH$_2$ and NH$_2$); IR (KBr, cm$^{-1}$) 2218.6 (s, CN), 3371.3 3302.5 (d, NH$_2$).

PART B: Preparation of 4-N-butyramido-4-cyanotetrahydro-thiopyrane

Butyryl chloride (5.8 mL, 40.8 mmol) was added dropwise to a cooled mixture of 4-amino-4-cyano-tetrahydrothiopyrane (5.28 g, 37.1 mmol) and triethyl amine (5 mL) in methylene chloride (150 mL). The mixture was stirred for 3 h at room temperature after which it was poured into 1N HCl (50 mL). The organic layer was washed with 1N HCl (2×50 mL), 1N NaOH (2×50 mL), dried (MgSO$_4$) and concentrated. The residue was triturated with hexane to give a white solid (7.50 g, 95%). MS m/e 213, (M+H)+, $^1$HNMR (CDCl$_3$/TMS) δ0.98 (t, 3H, CH$_3$), 1.68 (m, 2H, CH$_2$), 1.96 (m, 2H, CH$_2$), 2.20 (t, 2H, CH$_2$), 2.70 (m, 4H, CH$_2$), 3.01 (m, 2H, CH$_2$), 5.50 (s, 1H, NH).

PART C: Preparation of 4-aminocarbonyl-4-N-butyramido-tetrahydrothiopyrane

4-N-butyramido-4-cyanotetrahydro-thiopyrane (7.5 g, 35.3 mmol) was dissolved in concentrated hydrochloric acid (50 mL) at 0° C. Cold water (175 mL) was added immediately followed by treatment with concentrated ammonium hydroxide to pH 5–6. The mixture was extracted successively with methylene chloride. The organic layer was combined, washed with brine, dried over MgSO$_4$ and concentrated to give white solid (7.0 g, 86%). MS m/e 231 (M+H)+, $^1$HNMR (DMSO-d6/FMS)δ0.86 (t, 3H, CH3), 1.50 (s, 2H, CH$_2$), 1.90 (t, 2H, CH$_2$), 2.18 (t, 2H, CH$_2$), 2.20–2.47 (m, 4H, CH$_2$), 2.76 (t, 2H, CH$_2$), 6.90 (t, 2H, NH$_2$), 7.68 (s, 1H, NH).

PART D: Preparation of 4-oxo-2-propyl-8-thia-1,3-diazaspiro-(4.5)dec-1-ene

4-Aminocarbonyl-4-N-butyramido-tetrahydrothiopyrane (7.0 g, 30.4 mmol) was heated with 1N sodium hydroxide (50 mL) for 30 minutes. The mixture was cooled to room temperature and some solid material was filtered off. The filtrate was neutralized with aqueous HCl and the white precipitate formed was filtered and dried (2.63 g). The aqueous layer was extracted with methylene chloride. The combined organic layer was washed with brine, dried and concentrated to a white solid (1.35 g). A total of 3.98 g of product was isolated (62%). MS m/e 213 (M+H)+, $^1$HNMR (CDCl$_3$/TMS)δ1.00 (t, 3H, CH$_3$), 1.60–1.80 (m, 4H, CH$_2$), 2.05 (m, 2H, CH$_2$), 2.44 (t, 2H, CH$_2$), 2.75 (m, 2H, CH$_2$), 3.02 (t, 2H, CH$_2$), 8.30 (s, 1H, NH).

PART E: Preparation of N-[(4'-[((4-oxo-2-propyl-8-thia-1,3 -diazaspiro-[(4.5)]dec-1-en-3-yl-methyl)1-N-tert-butyl [(1,1'-biphenyl)]-2-sulfonamide 4-Oxo-2-propyl-8-thia- 1,3-diazaspiro-(4.5)dec-1-ene(0.83 g, 3.9 mmol) was dissolved in dimethyl formamide (20 mL). Sodium hydride (0.18 g of 80% dispersion in mineral oil) was added portionwise. The mixture was allowed to stir at room temperature for 15 minutes. 4'-bromomethyl-N-tert-butyl (1,1'-biphenyl)-2-sulfonamide (1.5 g, 3.9 mmol) was added. The mixture was stirred at room temperature under N$_2$ for 24 h. The solvent was removed in vacuo. The residue was dissolved in ethyl acetate and washed with water and brine. It was then dried over MgSO$_4$, concentrated and chromatographed on silica gel eluting with hexane-ethyl acetate (1:1) to yield 1.65 g of white solid (82%). MS m/e 514.2 (M+H)+, $^1$HNMR(CDCl$_3$/TMS)δ0.98 (t, 3H, CH$_3$), 0.99 (s, 9H, CH$_3$), 1.74 (m, 4H, CH$_2$), 2.10 (m, 2H, CH$_2$), 2.34 (t, 2H, CH$_2$), 2.79 (m, 2H, CH$_2$), 3.09 (t, 2H, CH$_2$), 3.45 (s, 1H, NH), 4.73 (s, 2H, CH$_2$Ar), 7.25 (m, 3H, ArH), 7.50 (m, 4H, ArH), 8.18 (d, 1H, ArH).

PART F: Preparation of N-((4'-(((4-oxo-2-propyl-8-thia-1,3 -diazaspiro-((4.5))dec-1-en-3-yl-methyl))((1,1'-biphenyl))-2-sulfonamide N-((4'-(((4-oxo-2-propyl-8-thia-1,3-diazaspiro-((4.5))dec-1-en-3 -yl-methyl))-N-tert-butyl((1,1'-biphenyl))-2-sulfonamide (1.56 g, 3.0 mmol) was refluxed with trifluoroacetic acid (10 mL) under N$_2$ for 2 h. The solvent was removed in vacuo and the residue was dissolved in methylene chloride. The organic solution was washed with aqueous NaHCO$_3$ and brine. It was filtered through phase transfer paper and concentrated to an off-white solid (1.31 g, 95%). MS m/e 458.0 (M+H)+, $^1$HNMR(CDCl$_3$/TMS)δ0.97 (t, 3H, CH$_3$), 1.60–1.82 (m, 4H, CH$_2$), 2.10 (m, 2H, CH$_2$), 2.36 (t, 2H, CH$_2$), 2.78 (m, 2H, CH$_2$), 3.09 (t, 2H, CH$_2$), 4.21 (s, 2H, NH$_2$), 4.73 (s, 2H, CH$_2$Ar), 7.20 (d, 2H, ArH), 7.30 (d,1H, ArH), 7.42–7.63 (m, 4H, ArH), 8.17 (d, 1H, ArH).

PART G: Preparation of N-((4'-(((4-oxo-2-propyl-8-thia-1,3 -diazaspiro-(4.5))dec-1-en-3-yl-methyl))((1,1'-biphenyl))-2-ylsulfonyl))-benzamide 1,1'-Carbonyl diimidazole (1.26 g, 7.8 mmol) and benzoic acid (0.96-g, 7.8 mmol) was refluxed with tetrahydrofurane (30 mL) under N$_2$ for 2 h. The mixture was cooled to room temperature, and a solution of N-((4'-(((4-oxo-2 -propyl-8-thia-1,3-diazaspiro-((4.5))dec-1-en-3-yl-methyl))((1,1'-biphenyl))-2-sulfonamide (1.20 g. 2.6 mmol) and 1,8-diazabicyclo[5.4.0]undec-7-ene (1.2 mL, 7.8 mmol) in THF (30 mL) was added. The reaction mixture was then refluxed for 1.5 h. The mixture was cooled and poured into 20 mL of 25% aqueous citric acid. It was extracted with ethyl acetate. The combined organic solution was washed with brine, dried over MgSO$_4$ and concentrated. The residue was chromatographed on silica gel eluting with 5% methanol in methylene chloride to yield 1.3 g of the desired product (91%). M.P. 105°–108° C., MS m/e 561 (M+H)+, $^1$HNMR(CDCl$_3$/TMS)δ0.98 (t, 3H, CH$_3$), 1.60–1.80 (m, 4H, CH$_2$), 2.08 (t, 2H, CH$_2$), 2.34 (t, 2H, CH$_2$), 2.78 (m, 2H, CH$_2$), 3.08 (t, 2H, CH$_2$), 4.65 (s, 2H, CH$_2$Ar), 6.99 (d, 2H, ArH), 7.23 (d, 1H, ArH), 7.42 (m, 4H, ArH), 7.60 (m, 4H, ArH), 8.40 (d, 1H, ArH).

EXAMPLE 2

N-((4'-(((4-oxo-2-propyl-1,3-diazaspiro((4.4) )non-1-en-3-yl)methyl))((1,1'-ylsulfonyl))-benzamide PART A: Preparation of 4-oxo-2-propyl-1,3-diazaspiro-(4.4)non-1-ene 1-Amino-1-cyclopentane carboxylic acid methyl ester (10.1 g, 70.6 mmol), ethyl butanimidate hydrochloride (12.7 g, 84.7 mmol) and triethyl amine (17 mL) was refluxed in benzene (50 mL) under N$_2$ overnight. The solvent was removed in vacuo and the residue was dissolved in methylene chloride, washed with water and brine, and concentrated. The crude product mixture was chromatographed on silica gel eluting with ethyl acetate to give 8.47 g of colorless oil (67%). MS m/e 181.1. (M+H)+, $^1$HNMR(CDCl$_3$/TMS) δ1.00 (t, 3H, CH$_3$), 1.50–2.20 (m, 10H, CH$_2$), 2.41 (t, 2H, CH$_2$), 9.09 (br.s, 1H, NH).

PART B: N-((4'-(((4-oxo-2-propyl-1,3-diazaspiro-((4.4))non-1-en-3 -yl)methyl))((1,1'-biphenyl-2-ylsulfonyl))-benamide The titled compound was prepared from 4-oxo-2-propyl-1,3-diazaspiro-(4.4)non-1-ene and 4'-bromomethyl-N-tert-butyl(1,1'-biphenyl)-2-sulfonamide according to the procedures described in Pan E, F and G of Example 1. M.P. 118°–125° C., MS m/e 529 (M+H)+, $^1$HNMR(DMSO-d6/TMS)δ0.89 (t, 3H, CH$_3$), 1.50–1.92 (m, 10H, CH$_2$), 2.34 (t, 2H, CH$_2$), 4.68 (s, 2H, CH$_2$Ar), 7.00 (d, 2H, ArH), 7.10–7.62 (m, 10H, ArH), 8.10 (d, 1H, ArH).

Compounds 1-625 in Table 1 can be prepared by the procedures described in Examples 1 and 2 employing the appropriately substituted imidazolines and benzyl halides or mesylates.

TABLE 1

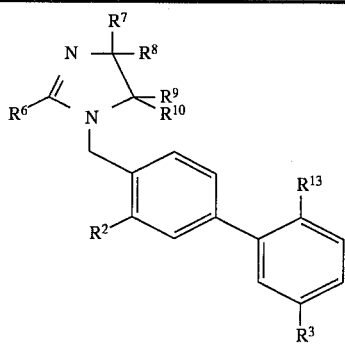

| Ex. | R⁶ | R⁷ | R⁸ | R⁹, R¹⁰ | R¹³ | R², R³ | MS(M + H)⁺ |
|---|---|---|---|---|---|---|---|
| 1 | n-Pr | —(CH$_2$)S(CH$_2$)$_2$— | | O | —SO$_2$NHCOC$_6$H$_5$ | H,H | 561 |
| 2 | n-Pr | —(CH$_2$)$_4$— | | O | —SO$_2$NHCOC$_6$H$_5$ | H,H | 529 |
| 3 | n-Pr | —(CH$_2$)$_4$— | | O | —SO$_2$NHCO(n-C$_4$H$_9$) | H,H | |
| 4 | n-Bu | —(CH$_2$)$_4$— | | O | —SO$_2$NHCOC$_6$H$_5$ | H,H | 543 |
| 5 | n-Pr | CH$_3$ | CH$_3$ | O | —SO$_2$NHCOC$_6$H$_5$ | H,H | 504 |
| 6 | n-Pr | CH$_3$ | CH$_3$ | O | —CONHSO$_2$CH$_2$C$_6$H$_5$ | H,H | |
| 7 | n-Pr | CH$_3$ | CH$_3$ | O | —SO$_2$NHCO(n-C$_5$H$_{11}$) | H,H | |
| 8 | n-Pr | CH$_3$ | CH$_3$ | O | —SO$_2$NHCO(cy-C$_3$H$_5$) | H,H | |
| 9 | n-Pr | CH$_3$ | CH$_3$ | O | —SO$_2$NHCOCH$_2$C$_6$H$_5$ | H,H | |
| 10 | n-Pr | CH$_3$ | CH$_3$ | O | —CH$_2$CO$_2$H | H,H | |
| 11 | n-Pr | CH$_3$ | CH$_3$ | O | —C(CF$_3$)$_2$OH | H,H | |
| 12 | n-Pr | CH$_3$ | CH$_3$ | O | —CONHNHSO$_2$CF$_3$ | H,H | |
| 13 | n-Pr | CH$_3$ | CH$_3$ | O | —CONHOCH$_3$ | H,H | |
| 14 | n-Pr | CH$_3$ | CH$_3$ | O | —CONHSO$_2$C$_6$H$_5$ | H,H | |
| 15 | n-Pr | CH$_3$ | CH$_3$ | O | —PO$_3$H$_2$ | H,H | |
| 16 | n-Pr | CH$_3$ | CH$_3$ | O | —SO$_2$NHCOC$_6$H$_5$ | CH$_3$,H | |
| 17 | n-Pr | CH$_3$ | CH$_3$ | O | —SO$_2$NHCO(n-C$_5$H$_{11}$) | CH$_3$,H | |
| 18 | n-Pr | CH$_3$ | CH$_3$ | O | —SO$_2$NHCO(cy-C$_3$H$_5$) | CH$_3$,H | |
| 19 | n-Pr | CH$_3$ | CH$_3$ | O | —SO$_2$NHCOCH$_2$C$_6$H$_5$ | CH$_3$,H | |
| 20 | n-Pr | CH$_3$ | CH$_3$ | O | —SO$_3$H | CH$_3$,H | |
| 21 | n-Pr | CH$_3$ | CH$_3$ | O | —SO$_2$HCONH(n-Bu) | CH$_3$,H | |
| 22 | n-Pr | CH$_3$ | CH$_3$ | O | —SO$_2$NH(C$_5$NH$_4$) | CH$_3$,H | |
| 23 | n-Pr | CH$_3$ | CH$_3$ | O | —SO$_2$NHCONH(n-C$_5$H$_{11}$) | CH$_3$,H | |
| 24 | n-Pr | CH$_3$ | CH$_3$ | O | —NHSO$_2$NHCO(i-C$_5$H$_{11}$) | CH$_3$,H | |
| 25 | n-Pr | CH$_3$ | CH$_3$ | O | —NHSO$_2$NHCO(cy-C$_3$H$_5$) | CH$_3$,H | |
| 26 | n-Pr | CH$_3$ | CH$_3$ | O | —NHSO$_2$NHCOCH$_2$C$_6$H$_5$ | CH$_3$,H | |
| 27 | n-Pr | CH$_3$ | CH$_3$ | O | —SO$_2$NHCOC$_6$H$_5$ | Cl,H | |
| 28 | n-Pr | CH$_3$ | CH$_3$ | O | —SO$_2$NHCO(n-C$_5$H$_{11}$) | Cl,H | |
| 29 | n-Pr | CH$_3$ | CH$_3$ | O | —SO$_2$NHCO(cy-C$_3$H$_5$) | Cl,H | |
| 30 | n-Pr | CH$_3$ | CH$_3$ | O | —SO$_2$NHCOCH$_2$C$_6$H$_5$ | Cl,H | |
| 31 | n-Pr | CH$_3$ | CH$_3$ | O | —OPO$_3$H$_2$ | Cl,H | |
| 32 | n-Pr | CH$_3$ | CH$_3$ | O | —PO(OH)CH$_2$C$_6$H$_5$ | Cl,H | |
| 33 | n-Pr | CH$_3$ | CH$_3$ | O | —OSO$_3$H | Cl,H | |
| 34 | n-Pr | CH$_3$ | CH$_3$ | O | —NHPO$_3$H$_2$ | Cl,H | |
| 35 | n-Pr | CH$_3$ | CH$_3$ | O | —SO$_2$NH$_2$ | Cl,H | |
| 36 | n-Pr | CH$_3$ | CH$_3$ | O | —SO$_2$NHC$_2$H$_5$ | Cl,H | |
| 37 | n-Pr | CH$_3$ | CH$_3$ | O | —SO$_2$NHC$_{10}$H$_7$ | Cl,H | |
| 38 | n-Pr | CH$_3$ | CH$_3$ | O | —SO$_2$NHCOC$_6$H$_5$ | F,H | |
| 39 | n-Pr | CH$_3$ | CH$_3$ | O | —SO$_2$NHCO(n-C$_5$H$_{11}$) | F,H | |
| 40 | n-Pr | CH$_3$ | CH$_3$ | O | —SO$_2$NHCO(cy-C$_3$H$_5$) | F,H | |
| 41 | n-Pr | CH$_3$ | CH$_3$ | O | —SO$_2$NHCOCH$_2$C$_6$H$_5$ | F,H | |
| 42 | n-Pr | CH$_3$ | CH$_3$ | O | —NHSO$_2$NHCO(n-Bu) | F,H | |
| 43 | n-Pr | CH$_3$ | CH$_3$ | O | —SO$_2$NHCONH(n-Bu) | F,H | |
| 44 | n-Pr | CH$_3$ | CH$_3$ | O | —SO$_2$NHCO(i-Bu) | F,H | |
| 45 | n-Pr | CH$_3$ | CH$_3$ | O | —SO$_2$NHCO(4-HOC$_6$H$_5$) | F,H | |
| 46 | n-Pr | CH$_3$ | CH$_3$ | O | —SO$_2$NHCOCH$_2$C$_6$H$_5$ | F,H | |
| 47 | n-Pr | CH$_3$ | CH$_3$ | O | —SO$_2$NHCO(4-C$_5$NH$_4$) | F,H | |
| 48 | n-Pr | CH$_3$ | CH$_3$ | O | —SO$_2$NHCONHCH$_2$C$_6$H$_5$ | F,H | |
| 49 | n-Pr | CH$_3$ | CH$_3$ | O | —SO$_2$NHCOC$_6$H$_5$ | H,n-Pr | |
| 50 | n-Pr | CH$_3$ | CH$_3$ | O | —SO$_2$NHCO(n-C$_6$H$_{11}$) | H,n-Pr | |
| 51 | n-Pr | CH$_3$ | CH$_3$ | O | —SO$_2$NHCO(cy-C$_3$H$_5$) | H,n-Pr | |
| 52 | n-Pr | CH$_3$ | CH$_3$ | O | —SO$_2$NHCOCH$_2$C$_6$H$_5$ | H,n-Pr | |
| 53 | n-Pr | CH$_3$ | CH$_3$ | O | —CH$_2$CO$_2$H | H,n-Pr | |
| 54 | n-Pr | CH$_3$ | CH$_3$ | O | —C(CF$_3$)$_2$OH | H,n-Pr | |
| 55 | n-Pr | CH$_3$ | CH$_3$ | O | —CONHNHSO$_2$CF$_3$ | H,n-Pr | |
| 56 | n-Pr | CH$_3$ | CH$_3$ | O | —CONHOH | H,n-Pr | |
| 57 | n-Pr | CH$_3$ | CH$_3$ | O | —CONHOCH$_3$ | H,n-Pr | |
| 58 | n-Pr | CH$_3$ | CH$_3$ | O | —CONHOCH$_2$C$_6$C$_5$ | H,n-Pr | |
| 59 | n-Pr | CH$_3$ | CH$_3$ | O | —SO$_2$NHCOC$_6$H$_5$ | Cl,n-Pr | |
| 60 | n-Pr | CH$_3$ | CH$_3$ | O | —SO$_2$NHCO(n-C$_5$H$_{11}$) | Cl,n-Pr | |
| 61 | n-Pr | CH$_3$ | CH$_3$ | O | —SO$_2$NHCO(cy-C$_3$H$_5$) | F,n-Pr | |

TABLE 1-continued

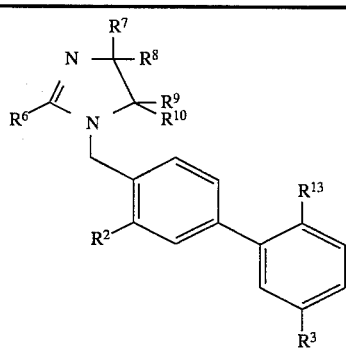

| Ex. | R⁶ | R⁷ | R⁸ | R⁹, R¹⁰ | R¹³ | R², R³ | MS(M + H)⁺ |
|---|---|---|---|---|---|---|---|
| 62 | n-Pr | CH₃ | CH₃ | O | —SO₂NHCOCH₂C₆H₅ | F,n-Pr | |
| 63 | n-Pr | CH₃ | CH₃ | O | —CONHSO₂(4-ClC₆H₄) | Cl,n-Pr | |
| 64 | n-Pr | CH₃ | CH₃ | O | —CONHSO₂C₂F₅ | F,n-Pr | |
| 65 | n-Pr | CH₃ | CH₃ | O | —CONHSO₂C₂H₄OH | Cl,n-Pr | |
| 66 | n-Pr | CH₃ | CH₃ | O | —CONHSO₂C₂H₄CO₂H | F,n-Pr | |
| 67 | n-Pr | CH₃ | CH₃ | O | —CONHSO₂C₂H₄NH₂ | F,n-Pr | |
| 68 | n-Pr | CH₃ | CH₃ | O | —CONHSO₂NH₂ | Cl,n-Pr | |
| 69 | n-Bu | CH₃ | CH₃ | O | —SO₂NHCOC₆H₅ | H,H | |
| 70 | n-Bu | CH₃ | CH₃ | O | —SO₂NHCO(n-C₅H₁₁) | H,H | |
| 71 | n-Bu | CH₃ | CH₃ | O | —SO₂NHCO(cy-C₃H₅) | H,H | |
| 72 | n-Bu | CH₃ | CH₃ | O | —SO₂NHCOCH₂C₆H₅ | H,H | |
| 73 | n-Bu | CH₃ | CH₃ | O | —CONHSO₂NHC₂H₅ | H,H | |
| 74 | n-Bu | CH₃ | CH₃ | O | —CONHSO₂NHC₆H₅ | H,H | |
| 75 | n-Bu | CH₃ | CH₃ | O | —CONHSO₂NHCH₂C₆H₅ | H,H | |
| 76 | n-Bu | CH₃ | CH₃ | O | —CONHSO₂NH(4-C₅NH₄) | H,H | |
| 77 | n-Bu | CH₃ | CH₃ | O | —C(OH)CH₃PO₃H₂ | H,H | |
| 78 | n-Bu | CH₃ | CH₃ | O | —C(OH)HPO₃H₂ | H,H | |
| 79 | n-Bu | CH₃ | CH₃ | O | —SO₂NHCOC₆H₅ | CH₃,H | |
| 80 | n-Bu | CH₃ | CH₃ | O | —SO₂NHCO(n-C₅H₁₁) | CH₃,H | |
| 81 | n-Bu | CH₃ | CH₃ | O | —SO₂NHCO(cy-C₃H₅) | CH₃,H | |
| 82 | n-Bu | CH₃ | CH₃ | O | —SO₂NHCOCH₂C₆H₅ | CH₃,H | |
| 83 | n-Bu | CH₃ | CH₃ | O | —NHCONHSO₂C₂H₅ | CH₃,H | |
| 84 | n-Bu | CH₃ | CH₃ | O | —NHCONHSO₂(i-Bu) | CH₃,H | |
| 85 | n-Bu | CH₃ | CH₃ | O | —NHCONHSO₂(n-C₅H₁₁) | CH₃,H | |
| 86 | n-Bu | CH₃ | CH₃ | O | —SO₂NHCONH(n-C₅H₁₁) | CH₃,H | |
| 87 | n-Bu | CH₃ | CH₃ | O | —SO₂NHCO(i-C₅H₁₁) | CH₃,H | |
| 88 | n-Bu | CH₃ | CH₃ | O | —SO₂NHCO(cy-C₃H₅) | CH₃,H | |
| 89 | n-Bu | CH₃ | CH₃ | O | —SO₂NHCOCH₂C₆H₅ | CH₃,H | |
| 90 | n-Bu | CH₃ | CH₃ | O | —SO₂NHCOC₆H₅C₆H₅ | Cl,H | |
| 91 | n-Bu | CH₃ | CH₃ | O | —SO₂NHCO(n-C₅H₁₁) | Cl,H | |
| 92 | n-Bu | CH₃ | CH₃ | O | —SO₂NHCO(cy-C₃H₅) | Cl,H | |
| 93 | n-Bu | CH₃ | CH₃ | O | —SO₂NHCOCH₂C₆H₅ | Cl,H | |
| 94 | n-Bu | CH₃ | CH₃ | O | —NHPO₃H₂ | Cl,H | |
| 95 | n-Bu | CH₃ | CH₃ | O | —NHSO₂NHCO(cy-C₃H₅) | Cl,H | |
| 96 | n-Bu | CH₃ | CH₃ | O | —SO₂NHCONH(i-Bu) | Cl,H | |
| 97 | n-Bu | CH₃ | CH₃ | O | —PO(OH)(n-C₅H₁₁) | Cl,H | |
| 98 | n-Bu | CH₃ | CH₃ | O | —PO(OH)(i-C₅H₁₁) | Cl,H | |
| 99 | n-Bu | CH₃ | CH₃ | O | —PO(OH)C₃H₇ | Cl,H | |
| 100 | n-Bu | CH₃ | CH₃ | O | —SO₂NHCH₂C₆H₅ | Cl,H | |
| 101 | n-Bu | CH₃ | CH₃ | O | —SO₂NH₂C₆H₅ | F,H | |
| 102 | n-Bu | CH₃ | CH₃ | O | —SO₂NHCO(n-C₅H₁₁) | F,H | |
| 103 | n-Bu | CH₃ | CH₃ | O | —SO₂NHCO(cy-C₃H₅) | F,H | |
| 104 | n-Bu | CH₃ | CH₃ | O | —SO₂NHCOCH₂C₆H₅ | F,H | |
| 105 | n-Bu | CH₃ | CH₃ | O | —SO₂NH(n-Bu) | F,H | |
| 106 | n-Bu | CH₃ | CH₃ | O | —SO₂NH(i-Bu) | F,H | |
| 107 | n-Bu | CH₃ | CH₃ | O | —SO₂NHCONH(i-Bu) | F,H | |
| 108 | n-Bu | CH₃ | CH₃ | O | —SO₂NH(n-C₅H₁₁) | F,H | |
| 109 | n-Bu | CH₃ | CH₃ | O | —SO₂NH(i-C₅H₁₁) | F,H | |
| 110 | n-Bu | CH₃ | CH₃ | O | —NHSO₂NHCO(cy-C₃H₅) | F,H | |
| 111 | n-Bu | CH₃ | CH₃ | O | —SO₂NHCOCH₂C₆H₅ | F,H | |
| 112 | n-Bu | CH₃ | CH₃ | O | —SO₂NHCOC₆H₅ | H,n-Pr | |
| 113 | n-Bu | CH₃ | CH₃ | O | —SO₂NHCO(n-C₅H₁₁) | H,n-Pr | |
| 114 | n-Bu | CH₃ | CH₃ | O | —SO₂NHCO(cy-C₃H₅) | H,n-Pr | |
| 115 | n-Bu | CH₃ | CH₃ | O | —SO₂NHCOCH₂C₆H₅ | H,n-Pr | |
| 116 | n-Bu | CH₃ | CH₃ | O | —SO₂NHCO(n-Bu) | H,n-Pr | |
| 117 | n-Bu | CH₃ | CH₃ | O | —SO₂NHCONH(n-Bu) | H,n-Pr | |
| 118 | n-Bu | CH₃ | CH₃ | O | —SO₂NHCONH(i-Bu) | H,n-Pr | |
| 119 | n-Bu | CH₃ | CH₃ | O | —SO₂NH(n-C₅H₁₁) | H,n-Pr | |
| 120 | n-Bu | CH₃ | CH₃ | O | —SO₂NH(i-C₅H₁₁) | H,n-Pr | |
| 121 | n-Bu | CH₃ | CH₃ | O | —SO₂NH(cy-C₃H₅) | H,n-Pr | |
| 122 | n-Bu | CH₃ | CH₃ | O | —SO₂NHCH₂C₆H₅ | H,n-Pr | |

TABLE 1-continued

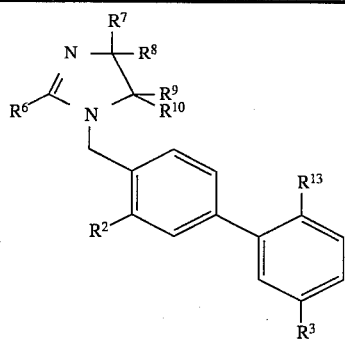

| Ex. | R6 | R7 | R8 | R9, R10 | R13 | R2, R3 | MS(M + H)+ |
|---|---|---|---|---|---|---|---|
| 123 | n-Bu | CH3 | CH3 | O | —SO2NHCOC6H5 | Cl,n-Pr | |
| 124 | n-Bu | CH3 | CH3 | O | —SO2NHCO(n-C5H11) | Cl,n-Pr | |
| 125 | n-Bu | CH3 | CH3 | O | —SO2NHCO(cy-C3H5) | F,n-Pr | |
| 126 | n-Bu | CH3 | CH3 | O | —SO2NHCOCH2C6H5 | F,n-Pr | |
| 127 | n-Bu | CH3 | CH3 | O | —SO2NH(n-Bu) | Cl,n-Pr | |
| 128 | n-Bu | CH3 | CH3 | O | —SO2NH(i-Bu) | F,-Pr | |
| 129 | n-Bu | CH3 | CH3 | O | —CONHSO2(n-C5H11) | Cl,n-Pr | |
| 130 | n-Bu | CH3 | CH3 | O | —CONHSO2(i-C5H11) | F,-Pr | |
| 131 | n-Bu | CH3 | CH3 | O | —CONHSO2(cy-C3H5) | F,n-Pr | |
| 132 | n-Bu | CH3 | CH3 | O | —CONHSO2CH2C6H5 | Cl,n-Pr | |
| 133 | Ph | CH3 | CH3 | O | —SO2NHCOC6H5 | H,H | |
| 134 | Ph | CH3 | CH3 | O | —SO2NHCO(n-C5H11) | H,H | |
| 135 | Ph | CH3 | CH3 | O | —SO2NHCO(cy-C3H5) | H,H | |
| 136 | p-F—Ph | CH3 | CH3 | O | —SO2NHCOCH2C6H5 | H,H | |
| 137 | p-F—Ph | CH3 | CH3 | O | —SO2NHCO(n-Bu) | H,H | |
| 138 | Ph | CH3 | CH3 | O | —SO2NHCO(i-Bu) | H,H | |
| 139 | iPr | CH3 | CH3 | O | —SO2NHCO(n-C5H11) | H,H | |
| 140 | Ph | CH3 | CH3 | O | —SO2NHCO(i-C5H11) | H,H | |
| 141 | Ph | CH3 | CH3 | O | —SO2NHCO(cy-C3H5) | H,H | |
| 142 | Ph | CH3 | CH3 | O | —SO2NHCOCH2C6H5 | H,H | |
| 143 | n-Pr | —(CH2)4— | | O | —CONHSO2CH2C6H5 | H,H | |
| 144 | n-Pr | —(CH2)4— | | O | —SO2NHCO(n-C5H11) | H,H | |
| 145 | n-Pr | —(CH2)4— | | O | —SO2NHCO(cy-C3H5) | H,H | |
| 146 | n-Pr | —(CH2)4— | | O | —SO2NHCOCH2C6H5 | H,H | |
| 147 | n-Pr | —(CH2)4— | | O | —CH2CO2H | H,H | |
| 148 | n-Pr | —(CH2)4— | | O | —C(CF3)2OH | H,H | |
| 149 | n-Pr | —(CH2)4— | | O | —CONIMSO2CF3 | H,H | |
| 150 | n-Pr | —(CH2)4— | | O | —CONHOCH2C6H5 | H,H | |
| 151 | n-Pr | —(CH2)4— | | O | —CONHOCH3 | H,H | |
| 152 | n-Pr | —(CH2)4— | | O | —SO2NHCOC6H5 | CH3,H | |
| 153 | n-Pr | —(CH2)4— | | O | —SO2NHCO(n-C5H11) | CH3,H | |
| 154 | n-Pr | —(CH2)4— | | O | —SO2NHCO(cy-C3H5) | CH3,H | |
| 155 | n-Pr | —(CH2)4— | | O | —SO2NHCOCH2C6H5 | CH3,H | |
| 156 | n-Pr | —(CH2)4— | | O | —SO2NHCO(n-Bu) | CH3,H | |
| 157 | n-Pr | —(CH2)4— | | O | —SO2NHCONH(n-Bu) | CH3,H | |
| 158 | n-Pr | —(CH2)4— | | O | —CONHSO2(i-Bu) | CH3,H | |
| 159 | n-Pr | —(CH2)4— | | O | —CONHSO2(n-C5H11) | CH3,H | |
| 160 | n-Pr | —(CH2)4— | | O | —CONHSO2(i-C5H11) | CH3,H | |
| 161 | n-Pr | —(CH2)4— | | O | —CONHSO2(cy-C5H5) | CH3,H | |
| 162 | n-Pr | —(CH2)4— | | O | —CONHSO2CH2C6H5 | CH3,H | |
| 163 | n-Pr | —(CH2)4— | | O | —SO2NHCOC6H5 | Cl,H | |
| 164 | n-Pr | —(CH2)4— | | O | —SO2NHCO(n-C5H11) | Cl,H | |
| 165 | n-Pr | —(CH2)4— | | O | —SO2NHCO(cy-C5H5) | Cl,H | |
| 166 | n-Pr | —(CH2)4— | | O | —SO2NHCOCH2C6H5 | Cl,H | |
| 167 | n-Pr | —(CH2)4— | | O | —CONHSO2NH(n-Bu) | Cl,H | |
| 168 | n-Pr | —(CH2)4— | | O | —SO2NHCONH(n-Bu) | Cl,H | |
| 169 | n-Pr | —(CH2)4— | | O | —NHCONHSO2(i-Bu) | Cl,H | |
| 170 | n-Pr | —(CH2)4— | | O | —NHCONHSO2(n-C5H11) | Cl,H | |
| 171 | n-Pr | —(CH2)4— | | O | —NHCONHSO2(i-C5H11) | Cl,H | |
| 172 | n-Pr | —(CH2)4— | | O | —NHCONHSO2(cy-C5H5) | Cl,H | |
| 173 | n-Pr | —(CH2)4— | | O | —NHCONHSO2CH2C6H5 | Cl,H | |
| 174 | n-Pr | —(CH2)4— | | O | —OP3H2 | F,H | |
| 175 | n-Pr | —(CH2)4— | | O | —OSO3H | F,H | |
| 176 | n-Pr | —(CH2)4— | | O | —SO2NHCO(cy-C3H5) | F,H | |
| 177 | n-Pr | —(CH2)4— | | O | —SO2NHCOCH2C6H5 | F,H | |
| 178 | n-Pr | —(CH2)4— | | O | —SO2NHCO(n-Bu) | F,H | |
| 179 | n-Pr | —(CH2)4— | | O | —SO2NHCONH(n-Bu) | F,H | |
| 180 | n-Pr | —(CH2)4— | | O | —SO2NHCO(i-Bu) | F,H | |
| 181 | n-Pr | —(CH2)4— | | O | —SO2NHCO(n-C5H11) | F,H | |
| 182 | n-Pr | —(CH2)4— | | O | —SO2NHCONH(i-C5H11) | F,H | |
| 183 | n-Pr | —(CH2)4— | | O | —SO2NHCONH(cy-C3H5) | F,H | |

TABLE 1-continued

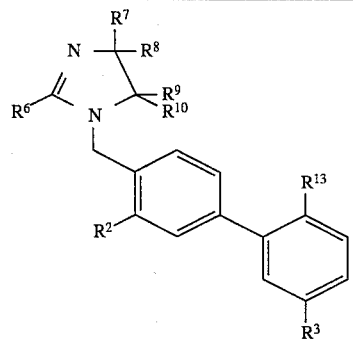

| Ex. | $R^6$ | $R^7$ | $R^8$ | $R^9, R^{10}$ | $R^{13}$ | $R^2, R^3$ | MS(M + H)+ |
|---|---|---|---|---|---|---|---|
| 184 | n-Pr | $-(CH_2)_4-$ | | O | $-SO_2NHCH_2C_6H_5$ | F,H | |
| 185 | n-Pr | $-(CH_2)_4-$ | | O | $-SO_2NHCOC_6H_5$ | H,n-Pr | |
| 186 | n-Pr | $-(CH_2)_4-$ | | O | $-SO_2NHCO(n-C_5H_{11})$ | H,n-Pr | |
| 187 | n-Pr | $-(CH_2)_4-$ | | O | $-SO_2NHCO(cy-C_3H_5)$ | H,n-Pr | |
| 188 | n-Pr | $-(CH_2)_4-$ | | O | $-SO_2NHCOCH_2C_6H_5$ | H,n-Pr | |
| 189 | n-Pr | $-(CH_2)_4-$ | | O | $-SO_2NHCO(n-Bu)$ | H,n-Pr | |
| 190 | n-Pr | $-(CH_2)_4-$ | | O | $-SO_2NHCONH(n-Bu)$ | H,n-Pr | |
| 191 | n-Pr | $-(CH_2)_4-$ | | O | $-SO_2NHCO(i-Bu)$ | H,n-Pr | |
| 192 | n-Pr | $-(CH_2)_4-$ | | O | $-SO_2NH(n-C_5H_{11})$ | H,n-Pr | |
| 193 | n-Pr | $-(CH_2)_4-$ | | O | $-SO_2NH(i-C_5H_{11})$ | H,n-Pr | |
| 194 | n-Pr | $-(CH_2)_4-$ | | O | $-SO_2NH(cy-C_3H_5)$ | H,n-Pr | |
| 195 | n-Pr | $-(CH_2)_4-$ | | O | $-SO_2NHCH_2C_6H_5$ | H,n-Pr | |
| 196 | n-Pr | $-(CH_2)_4-$ | | O | $-SO_2NHCOC_6H_5$ | Cl,n-Pr | |
| 197 | n-Pr | $-(CH_2)_4-$ | | O | $-SO_2NHCO(n-C_5H_{11})$ | Cl,n-Pr | |
| 198 | n-Pr | $-(CH_2)_4-$ | | O | $-SO_2NHCO(cy-C_3H_5)$ | F,n-Pr | |
| 199 | n-Pr | $-(CH_2)_4-$ | | O | $-SO_2NHCOCH_2C_6H_5$ | F,n-Pr | |
| 200 | n-Pr | $-(CH_2)_4-$ | | O | $-SO_2NHCO(n-Bu)$ | Cl,n-Pr | |
| 201 | n-Pr | $-(CH_2)_4-$ | | O | $-SO_2NHCOC_2H_5$ | F,n-Pr | |
| 202 | n-Pr | $-(CH_2)_4-$ | | O | $-SO_2NHCOCH_3$ | Cl,n-Pr | |
| 203 | n-Pr | $-(CH_2)_4-$ | | O | $-SO_2NHCO(i-C_5H_{11})$ | F,n-Pr | |
| 204 | n-Pr | $-(CH_2)_4-$ | | O | $-CH_2CO_2H$ | F,n-Pr | |
| 205 | n-Pr | $-(CH_2)_4-$ | | O | $-CONHNHSO_2CF_3$ | Cl,n-Pr | |
| 206 | n-Bu | $-(CH_2)_4-$ | | O | $-CONHSO_2(n-C_5H_{11})$ | H,H | |
| 207 | n-Bu | $-(CH_2)_4-$ | | O | $-SO_2NHCO(cy-C_3H_5)$ | H,H | |
| 208 | n-Bu | $-(CH_2)_4-$ | | O | $-SO_2NHCOCH_2C_6H_5$ | H,H | |
| 209 | n-Bu | $-(CH_2)_4-$ | | O | $-CONHSO_2(n-Bu)$ | H,H | |
| 210 | n-Bu | $-(CH_2)_4-$ | | O | $-CONHSO_2(i-Bu)$ | H,H | |
| 211 | n-Bu | $-(CH_2)_4-$ | | O | $-CONHSO_2(n-C_5H_{11})$ | H,H | |
| 212 | n-Bu | $-(CH_2)_4-$ | | O | $-CONHSO_2(i-C_5H_{11})$ | H,H | |
| 213 | n-Bu | $-(CH_2)_4-$ | | O | $-COHSO_2(cy-C_3H_5)$ | H,H | |
| 214 | n-Bu | $-(CH_2)_4-$ | | O | $-SO_2NHCOCH_2C_6H_5$ | H,H | |
| 215 | n-Bu | $-(CH_2)_4-$ | | O | $-SO_2NHCOC_6H_5$ | $CH_3$,H | |
| 216 | n-Bu | $-(CH_2)_4-$ | | O | $-SO_2NHCO(n-C_5H_{11})$ | $CH_3$,H | |
| 217 | n-Bu | $-(CH_2)_4-$ | | O | $-SO_2NHCO(cy-C_3H_5)$ | $CH_3$,H | |
| 218 | n-Bu | $-(CH_2)_4-$ | | O | $-SO_2NHCOCH_2C_6H_5$ | $CH_3$,H | |
| 219 | n-Bu | $-(CH_2)_4-$ | | O | $-NHCONHSO_2(n-Bu)$ | $CH_3$,H | |
| 220 | n-Bu | $-(CH_2)_4-$ | | O | $-NHCONHSO_2(i-Bu)$ | $CH_3$,H | |
| 221 | n-Bu | $-(CH_2)_4-$ | | O | $-SO_2NHCONH(i-Bu)$ | $CH_3$,H | |
| 222 | n-Bu | $-(CH_2)_4-$ | | O | $-SO_2NH(n-C_5H_{11})$ | $CH_3$,H | |
| 223 | n-Bu | $-(CH_2)_4-$ | | O | $-SO_2NH(i-C_5H_{11})$ | $CH_3$,H | |
| 224 | n-Bu | $-(CH_2)_4-$ | | O | $-SO_2NH_2(cy-C_3H_5)$ | $CH_3$,H | |
| 225 | n-Bu | $-(CH_2)_4-$ | | O | $-SO_2NHCH_2C_6H_5$ | $CH_3$,H | |
| 226 | n-Bu | $-(CH_2)_4-$ | | O | $-SO_2NHCOC_6H_5$ | Cl,H | |
| 227 | n-Bu | $-(CH_2)_4-$ | | O | $-SO_2NHCO(n-C_5H_{11})$ | Cl,H | |
| 228 | n-Bu | $-(CH_2)_4-$ | | O | $-SO_2NHCO(cy-C_3H_5)$ | Cl,H | |
| 229 | n-Bu | $-(CH_2)_4-$ | | O | $-SO_2NHCOH_2C_6H_5$ | Cl,H | |
| 230 | n-Bu | $-(CH_2)_4-$ | | O | $-NHSO_2HCO(n-Bu)$ | Cl,H | |
| 231 | n-Bu | $-(CH_2)_4-$ | | O | $-SO_2NHCONH(n-Bu)$ | Cl,H | |
| 232 | n-Bu | $-(CH_2)_4-$ | | O | $-NHSO_2NHCO(i-Bu)$ | Cl,H | |
| 233 | n-Bu | $-(CH_2)_4-$ | | O | $-NHSO_2NHCO(n-C_5H_{11})$ | Cl,H | |
| 234 | n-Bu | $-(CH_2)_4-$ | | O | $-NHSO_2NHCO(i-C_5H_{11})$ | Cl,H | |
| 235 | n-Bu | $-(CH_2)_4-$ | | O | $-CH_2(5-Tetrazoyl)$ | Cl,H | |
| 236 | n-Bu | $-(CH_2)_4-$ | | O | $-CONH(5-Tetrazoyl)$ | Cl,H | |
| 237 | n-Bu | $-(CH_2)_4-$ | | O | $-SO_2NHCOC_6H_5$ | F,H | |
| 238 | n-Bu | $-(CH_2)_4-$ | | O | $-SO_2NHCO(n-C_5H_{11})$ | F,H | |
| 239 | n-Bu | $-(CH_2)_4-$ | | O | $-SO_2NHCO(cy-C_3H_5)$ | F,H | |
| 240 | n-Bu | $-(CH_2)_4-$ | | O | $-SO_2NHCOCH_2C_6H_5$ | F,H | |
| 241 | n-Bu | $-(CH_2)_4-$ | | O | $-NHSO_2NHCO(n-Bu)$ | F,H | |
| 242 | n-Bu | $-(CH_2)_4-$ | | O | $-SO_2NHCONH(n-Bu)$ | F,H | |
| 243 | n-Bu | $-(CH_2)_4-$ | | O | $-SO_2NHCO(i-Bu)$ | F,H | |
| 244 | n-Bu | $-(CH_2)_4-$ | | O | $-SO_2NH(n-C_5H_{11})$ | F,H | |

TABLE 1-continued

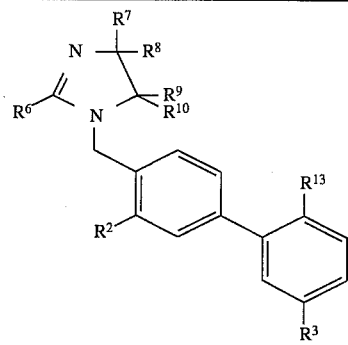

| Ex. | $R^6$ | $R^7$ | $R^8$ | $R^9, R^{10}$ | $R^{13}$ | $R^2, R^3$ | MS(M + H)$^+$ |
|---|---|---|---|---|---|---|---|
| 245 | n-Bu | $-(CH_2)_4-$ | | O | $-SO_2NH(i-C_5H_{11})$ | F,H | |
| 246 | n-Bu | $-(CH_2)_4-$ | | O | $-SO_2NH(cy-C_3H_5)$ | F,H | |
| 247 | n-Bu | $-(CH_2)_4-$ | | O | $-SO_2NHCH_2C_6H_5$ | F,H | |
| 248 | n-Bu | $-(CH_2)_4-$ | | O | $-SO_2NHCOC_6H_5$ | H,n-Pr | |
| 249 | n-Bu | $-(CH_2)_4-$ | | O | $-SO_2NHCO(n-C_5H_{11})$ | H,n-Pr | |
| 250 | n-Bu | $-(CH_2)_4-$ | | O | $-SO_2NHCO(cy-C_3H_5)$ | H,n-Pr | |
| 251 | n-Bu | $-(CH_2)_4-$ | | O | $-SO_2NHCOCH_2C_6H_5$ | H,n-Pr | |
| 252 | n-Bu | $-(CH_2)_4-$ | | O | $-CONHSO_2NHC_2H_4Cl$ | H,n-Pr | |
| 253 | n-Bu | $-(CH_2)_4-$ | | O | $-CONHSO_2(i-Bu)$ | H,n-Pr | |
| 254 | n-Bu | $-(CH_2)_4-$ | | O | $-CONHSO_2(n-C_5H_{11})$ | H,n-Pr | |
| 255 | n-Bu | $-(CH_2)_4-$ | | O | $-CONHSO_2(i-C_5H_{11})$ | H,n-Pr | |
| 256 | n-Bu | $-(CH_2)_4-$ | | O | $-CONHSO_2(cy-C_3H_5)$ | H,n-Pr | |
| 257 | n-Bu | $-(CH_2)_4-$ | | O | $-CONHSO_2CH_2C_6H_5$ | H,n-Pr | |
| 258 | n-Bu | $-(CH_2)_4-$ | | O | $-SO_2NHCOC_6H_5$ | Cl,n-Pr | |
| 259 | n-Bu | $-(CH_2)_4-$ | | O | $-SO_2NHCO(n-C_5H_{11})$ | Cl,n-Pr | |
| 260 | n-Bu | $-(CH_2)_4-$ | | O | $-SO_2NHCO(cy-C_3H_5)$ | F,n-Pr | |
| 261 | n-Bu | $-(CH_2)_4-$ | | O | $-SO_2NHCOCH_2C_6H_5$ | F,n-Pr | |
| 262 | n-Bu | $-(CH_2)_4-$ | | O | $-NHSO_2NHCO(n-Bu)$ | Cl,n-Pr | |
| 263 | n-Bu | $-(CH_2)_4-$ | | O | $-NHSO_2NHCO(i-Bu)$ | F,n-Pr | |
| 264 | n-Bu | $-(CH_2)_4-$ | | O | $-NHSO_2NHCO(n-C_5H_{11})$ | Cl,n-Pr | |
| 265 | n-Bu | $-(CH_2)_4-$ | | O | $-NHSO_2NHCO(i-C_5H_{11})$ | F,n-Pr | |
| 266 | n-Bu | $-(CH_2)_4-$ | | O | $-SO_2NHCO(i-C_5H_{11})$ | F,n-Pr | |
| 267 | n-Bu | $-(CH_2)_4-$ | | O | $-NHSO_2NHCO(cy-C_3H_5)$ | F,n-Pr | |
| 268 | n-Bu | $-(CH_2)_4-$ | | O | $-NHSO_2NHCOCH_2C_6H_5$ | Cl,n-Pr | |
| 269 | n-Bu | $-(CH_2)_5-$ | | O | $-CONHSO_2CH_2C_6H_5$ | H,H | |
| 270 | n-Pr | $-(CH_2)_5-$ | | O | $-SO_2NHCOC_6H_5$ | H,H | |
| 271 | n-Pr | $-(CH_2)_5-$ | | O | $-SO_2NHCO(n-C_5H_{11})$ | H,H | |
| 272 | n-Pr | $-(CH_2)_5-$ | | O | $-SO_2NHCO(cy-C_3H_5)$ | H,H | |
| 273 | n-Pr | $-(CH_2)_5-$ | | O | $-SO_2NHCOCH_2C_6H_5$ | H,H | |
| 274 | n-Pr | $-(CH_2)_5-$ | | O | $-SO_2NHCOC_6H_5$ | $CH_3$,H | |
| 275 | n-Pr | $-(CH_2)_5-$ | | O | $-SO_2NHCO(n-C_5H_{11})$ | $CH_3$,H | |
| 276 | n-Pr | $-(CH_2)_5-$ | | O | $-SO_2NHCO(cy-C_3H_5)$ | $CH_3$,H | |
| 277 | n-Pr | $-(CH_2)_5-$ | | O | $-SO_2NHCOCH_2C_6H_5$ | $CH_3$,H | |
| 278 | n-Pr | $-(CH_2)_5-$ | | O | $-NHSO_2NHCO(n-Bu)$ | $CH_3$,H | |
| 279 | n-Pr | $-(CH_2)_5-$ | | O | $-SO_2NHCONH(n-Bu)$ | $CH_3$,H | |
| 280 | n-Pr | $-(CH_2)_5-$ | | O | $-NHSO_2NHCO(i-Bu)$ | $CH_3$,H | |
| 281 | n-Pr | $-(CH_2)_5-$ | | O | $-NHSO_2NHCO(n-C_5H_{11})$ | $CH_3$,H | |
| 282 | n-Pr | $-(CH_2)_5-$ | | O | $-NHSO_2NHCO(i-C_5H_{11})$ | $CH_3$,H | |
| 283 | n-Pr | $-(CH_2)_5-$ | | O | $-NHSO_2NHCO(cy-C_3H_5)$ | $CH_3$,H | |
| 284 | n-Pr | $-(CH_2)_5-$ | | O | $-NHSO_2NHCOCH_2C_6H_5$ | $CH_3$,H | |
| 285 | n-Pr | $-(CH_2)_5-$ | | O | $-SO_2NHCOC_6H_5$ | Cl,H | |
| 286 | n-Pr | $-(CH_2)_5-$ | | O | $-SO_2NHCO(n-C_5H_{11})$ | Cl,H | |
| 287 | n-Pr | $-(CH_2)_5-$ | | O | $-SO_2NHCO(cy-C_3H_5)$ | Cl,H | |
| 288 | n-Pr | $-(CH_2)_5-$ | | O | $-SO_2NHCOCH_2C_6H_5$ | Cl,H | |
| 289 | n-Pr | $-(CH_2)_5-$ | | O | $-NHSO_2NHCO(n-Bu)$ | Cl,H | |
| 290 | n-Pr | $-(CH_2)_5-$ | | O | $-NHSO_2NHCO(n-Bu)$ | Cl,H | |
| 291 | n-Pr | $-(CH_2)_5-$ | | O | $-SO_2NHCONH(i-Bu)$ | Cl,H | |
| 292 | n-Pr | $-(CH_2)_5-$ | | O | $-SO_2NHCO(n-C_5H_{11})$ | Cl,H | |
| 293 | n-Pr | $-(CH_2)_5-$ | | O | $-NHSO_2NHCO(i-C_5H_{11})$ | Cl,H | |
| 294 | n-Pr | $-(CH_2)_5-$ | | O | $-SO_2NH(cy-C_3H_5)$ | Cl,H | |
| 295 | n-Pr | $-(CH_2)_5-$ | | O | $-SO_2NHCH_2C_6H_5$ | Cl,H | |
| 296 | n-Pr | $-(CH_2)_5-$ | | O | $-SO_2NHCOC_6H_5$ | F,H | |
| 297 | n-Pr | $-(CH_2)_5-$ | | O | $-SO_2NHCO(n-C_5H_{11})$ | F,H | |
| 298 | n-Pr | $-(CH_2)_5-$ | | O | $-SO_2NHCO(cy-C_3H_5)$ | F,H | |
| 299 | n-Pr | $-(CH_2)_5-$ | | O | $-SO_2NHCOCH_2C_6H_5$ | F,H | |
| 300 | n-Pr | $-(CH_2)_5-$ | | O | $-SO_2NHCO(n-Bu)$ | F,H | |
| 301 | n-Pr | $-(CH_2)_5-$ | | O | $-SO_2NHCONH(n-Bu)$ | F,H | |
| 302 | n-Pr | $-(CH_2)_5-$ | | O | $-NHSO_2NHCO(i-Bu)$ | F,H | |
| 303 | n-Pr | $-(CH_2)_5-$ | | O | $-NHSO_2NHCO(n-C_5H_{11})$ | F,H | |
| 304 | n-Pr | $-(CH_2)_5-$ | | O | $-NHSO_2NHCO(i-C_5H_{11})$ | F,H | |
| 305 | n-Pr | $-(CH_2)_5-$ | | O | $-NHSO_2NHCO(cy-C_3H_5)$ | F,H | |

TABLE 1-continued

| Ex. | R⁶ | R⁷ | R⁸ | R⁹, R¹⁰ | R¹³ | R², R³ | MS(M + H)⁺ |
|---|---|---|---|---|---|---|---|
| 306 | n-Pr | —(CH₂)₅— | | O | —NHSO₂NHCOCH₂C₆H₅ | F,H | |
| 307 | n-Pr | —(CH₂)₅— | | O | —SO₂NHCOC₆H₅ | H,n-Pr | |
| 308 | n-Pr | —(CH₂)₅— | | O | —SO₂NHCO(n-C₅H₁₁) | H,n-Pr | |
| 309 | n-Pr | —(CH₂)₅— | | O | —SO₂NHCO(cy-C₃H₅) | H,n-Pr | |
| 310 | n-Pr | —(CH₂)₅— | | O | —SO₂NHCOCH₂C₆H₅ | H,n-Pr | |
| 311 | n-Pr | —(CH₂)₅— | | O | —NHSO₂NHCO(n-Bu) | H,n-Pr | |
| 312 | n-Pr | —(CH₂)₅— | | O | —SO₂NHCONH(n-Bu) | H,n-Pr | |
| 313 | n-Pr | —(CH₂)₅— | | O | —NHSO₂NHCO(i-Bu) | H,n-Pr | |
| 314 | n-Pr | —(CH₂)₅— | | O | —NHSO₂NHCO(n-C₅H₁₁) | H,n-Pr | |
| 315 | n-Pr | —(CH₂)₅— | | O | —NHSO₂NHCO(i-C₅H₁₁) | H,n-Pr | |
| 316 | n-Pr | —(CH₂)₅— | | O | —NHSO₂NHCO(cy-C₃H₅) | H,n-Pr | |
| 317 | n-Pr | —(CH₂)₅— | | O | —NHSO₂NHCOCH₂C₆H₅ | H,n-Pr | |
| 318 | n-Pr | —(CH₂)₅— | | O | —SO₂NHCOC₆H₅ | Cl,n-Pr | |
| 319 | n-Pr | —(CH₂)₅— | | O | —SO₂NHCO(n-C₅H₁₁) | Cl,n-Pr | |
| 320 | n-Pr | —(CH₂)₅— | | O | —SO₂NHCO(cy-C₃H₅) | F,n-Pr | |
| 321 | n-Pr | —(CH₂)₅— | | O | —SO₂NHCOCH₂C₆H₅ | F,n-Pr | |
| 322 | n-Pr | —(CH₂)₅— | | O | —NHSO₂NHCO(n-Bu) | Cl,n-Pr | |
| 323 | n-Pr | —(CH₂)₅— | | O | —SO₂NHCONH(n-Bu) | Cl,n-Pr | |
| 324 | n-Pr | —(CH₂)₅— | | O | —NHSO₂NHCO(i-Bu) | F,n-Pr | |
| 325 | n-Pr | —(CH₂)₅— | | O | —NHSO₂NHCO(n-C₅H₁₁) | Cl,n-Pr | |
| 326 | n-Pr | —(CH₂)₅— | | O | —NHSO₂NHCO(i-C₅H₁₁) | F,n-Pr | |
| 327 | n-Pr | —(CH₂)₅— | | O | —NHSO₂NHCO(cy-C₃H₅) | F,n-Pr | |
| 328 | n-Pr | —(CH₂)₅— | | O | —NHSO₂NHCOCH₂C₆H₅ | Cl,n-Pr | |
| 329 | n-Bu | —(CH₂)₅— | | O | —SO₂NHCOC₆H₅ | H,H | |
| 330 | n-Bu | —(CH₂)₅— | | O | —SO₂NHCO(n-C₅H₁₁) | H,H | |
| 331 | n-Bu | —(CH₂)₅— | | O | —SO₂NHCO(cy-C₃H₅) | H,H | |
| 332 | n-Bu | —(CH₂)₅— | | O | —SO₂NHCOCH₂C₆H₅ | H,H | |
| 333 | n-Bu | —(CH₂)₅— | | O | —NHSO₂NHCO(n-Bu) | H,H | |
| 334 | n-Bu | —(CH₂)₅— | | O | —NHSO₂NHCO(i-Bu) | H,H | |
| 335 | n-Bu | —(CH₂)₅— | | O | —NHSO₂NHCO(n-C₅H₁₁) | H,H | |
| 336 | n-Bu | —(CH₂)₅— | | O | —NHSO₂NHCO(i-C₅H₁₁) | H,H | |
| 337 | n-Bu | —(CH₂)₅— | | O | —NHSO₂NHCO(cy-C₃H₅) | H,H | |
| 338 | n-Bu | —(CH₂)₅— | | O | —NHSO₂NHCOCH₂C₆H₅ | H,H | |
| 339 | n-Bu | —(CH₂)₅— | | O | —SO₂NHCOC₆H₅ | CH₃,H | |
| 340 | n-Bu | —(CH₂)₅— | | O | —SO₂NHCO(n-C₅H₁₁) | CH₃,H | |
| 341 | n-Bu | —(CH₂)₅— | | O | —SO₂NHCO(cy-C₃H₅) | CH₃,H | |
| 342 | n-Bu | —(CH₂)₅— | | O | —SO₂NHCOCH₂C₆H₅ | CH₃,H | |
| 343 | n-Bu | —(CH₂)₅— | | O | —NHSO₂NHCO(n-Bu) | CH₃,H | |
| 344 | n-Bu | —(CH₂)₅— | | O | —SO₂NHCONH(n-Bu) | CH₃,H | |
| 345 | n-Bu | —(CH₂)₅— | | O | —NHSO₂NHCO(i-Bu) | CH₃,H | |
| 346 | n-Bu | —(CH₂)₅— | | O | —NHSO₂NHCO(n-C₅H₁₁) | CH₃,H | |
| 347 | n-Bu | —(CH₂)₅— | | O | —NHSO₂NHCO(i-C₅H₁₁) | CH₃,H | |
| 348 | n-Bu | —(CH₂)₅— | | O | —NHSO₂NHCO(cy-C₃H₅) | CH₃,H | |
| 349 | n-Bu | —(CH₂)₅— | | O | —NHSO₂NHCOCH₂C₆H₅ | CH₃,H | |
| 350 | n-Bu | —(CH₂)₅— | | O | —SO₂NHCOC₆H₅ | Cl,H | |
| 351 | n-Bu | —(CH₂)₅— | | O | —SO₂NHCO(N-C₅H₁₁) | Cl,H | |
| 352 | n-Bu | —(CH₂)₅— | | O | —SO₂NHCO(cy-C₃H₅) | Cl,H | |
| 353 | n-Bu | —(CH₂)₅— | | O | —SO₂NHCOCH₂C₆H₅ | Cl,H | |
| 354 | n-Bu | —(CH₂)₅— | | O | —NHSO₂NHCO(n-Bu) | Cl,H | |
| 355 | n-Bu | —(CH₂)₅— | | O | —NHSO₂NHCO(i-Bu) | Cl,H | |
| 356 | n-Bu | —(CH₂)₅— | | O | —NHSO₂NHCO(n-C₅H₁₁) | Cl,H | |
| 357 | n-Bu | —(CH₂)₅— | | O | —SO₂NHCONH(n-C₅H₁₁) | Cl,H | |
| 358 | n-Bu | —(CH₂)₅— | | O | —NHSO₂NHCO(i-C₅H₁₁) | Cl,H | |
| 359 | n-Bu | —(CH₂)₅— | | O | —NHSO₂NHCO(cy-C₃H₅) | Cl,H | |
| 360 | n-Bu | —(CH₂)₅— | | O | —NHSO₂NHCOCH₂C₆H₅ | Cl,H | |
| 361 | n-Bu | —(CH₂)₅— | | O | —SO₂NHCOC₆H₅ | F,H | |
| 362 | n-Bu | —(CH₂)₅— | | O | —SO₂NHCO(n-C₅H₁₁) | F,H | |
| 363 | n-Bu | —(CH₂)₅— | | O | —SO₂NHCO(cy-C₃H₅) | F,H | |
| 364 | n-Bu | —(CH₂)₅— | | O | —SO₂NHCOCH₂C₆H₅ | F,H | |
| 365 | n-Bu | —(CH₂)₅— | | O | —NHSO₂NHCO(n-Bu) | F,H | |
| 366 | n-Bu | —(CH₂)₅— | | O | —NHSO₂NHCO(i-Bu) | F,H | |

TABLE 1-continued

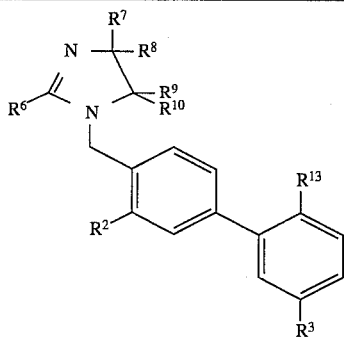

| Ex. | $R^6$ | $R^7$ | $R^8$ | $R^9, R^{10}$ | $R^{13}$ | $R^2, R^3$ | $MS(M+H)^+$ |
|---|---|---|---|---|---|---|---|
| 367 | n-Bu | —(CH$_2$)$_5$— | | O | —NHSO$_2$NHCO(n-C$_5$H$_{11}$) | F,H | |
| 368 | n-Bu | —(CH$_2$)$_5$— | | O | —SO$_2$NHCONH(n-C$_5$H$_{11}$) | F,H | |
| 369 | n-Bu | —(CH$_2$)$_5$— | | O | —NHSO$_2$NHCO(i-C$_5$H$_{11}$) | F,H | |
| 370 | n-Bu | —(CH$_2$)$_5$— | | O | —NHSO$_2$NHCO(cy-C$_3$H$_5$) | F,H | |
| 371 | n-Bu | —(CH$_2$)$_5$— | | O | —NHSO$_2$NHCOCH$_2$C$_6$H$_5$ | F,H | |
| 372 | n-Bu | —(CH$_2$)$_5$— | | O | —SO$_2$NHCOC$_6$H$_5$ | H,n-Pr | |
| 373 | n-Bu | —(CH$_2$)$_5$— | | O | —SO$_2$NHCO(n-C$_5$H$_{11}$) | H,n-Pr | |
| 374 | n-Bu | —(CH$_2$)$_5$— | | O | —SO$_2$NHCO(cy-C$_3$H$_5$) | H,n-Pr | |
| 375 | n-Bu | —(CH$_2$)$_5$— | | O | —SO$_2$NHCOCH$_2$C$_6$H$_5$ | H,-Pr | |
| 376 | n-Bu | —(CH$_2$)$_5$— | | O | —NHSO$_2$NHCO(n-Bu) | H,n-Pr | |
| 377 | n-Bu | —(CH$_2$)$_5$— | | O | —NHSO$_2$NHCO(i-Bu) | H,n-Pr | |
| 378 | n-Bu | —(CH$_2$)$_5$— | | O | —SO$_2$NHCONH(n-C$_5$H$_{11}$) | H,n-Pr | |
| 379 | n-Bu | —(CH$_2$)$_5$— | | O | —NHSO$_2$NHCO(n-C$_5$H$_{11}$) | H,n-Pr | |
| 380 | n-Bu | —(CH$_2$)$_5$— | | O | —NHSO$_2$NHCO(i-C$_5$H$_{11}$) | H,n-Pr | |
| 381 | n-Bu | —(CH$_2$)$_5$— | | O | —NHSO$_2$NHCO(cy-C$_3$H$_5$) | H,n-Pr | |
| 382 | n-Bu | —(CH$_2$)$_5$— | | O | —NHSO$_2$NHCOCH$_2$C$_6$H$_5$ | H,n-Pr | |
| 383 | n-Bu | —(CH$_2$)$_5$— | | O | —SO$_2$NHCOC$_6$H$_5$ | Cl,n-Pr | |
| 384 | n-Bu | —(CH$_2$)$_5$— | | O | —SO$_2$NHCO(n-C$_5$H$_{11}$) | Cl,n-Pr | |
| 385 | n-Bu | —(CH$_2$)$_5$— | | O | —SO$_2$NHCO(cy-C$_3$H$_5$) | F,n-Pr | |
| 386 | n-Bu | —(CH$_2$)$_5$— | | O | —SO$_2$NHCOCH$_2$C$_5$H$_6$ | F,n-Pr | |
| 387 | n-Bu | —(CH$_2$)$_5$— | | O | —NHSO$_2$NHCO(n-Bu) | Cl,n-Pr | |
| 388 | n-Bu | —(CH$_2$)$_5$— | | O | —SO$_2$NHCONH(n-Bu) | Cl,n-Pr | |
| 389 | n-Bu | —(CH$_2$)$_5$— | | O | —SO$_2$NHCONH(i-Bu) | Cl,n-Pr | |
| 390 | n-Bu | —(CH$_2$)$_5$— | | O | —NHSO$_2$NHCO(i-Bu) | F,n-Pr | |
| 391 | n-Bu | —(CH$_2$)$_5$— | | O | —NHSO$_2$NHCO(n-C$_5$H$_{11}$) | Cl,n-Pr | |
| 392 | n-Bu | —(CH$_2$)$_5$— | | O | —NHSO$_2$NHCO(i-C$_5$H$_{11}$) | F,n-Pr | |
| 393 | n-Bu | —(CH$_2$)$_5$— | | O | —NHSO$_2$NHCO(cy-C$_3$H$_5$) | F,n-Pr | |
| 394 | n-Bu | —(CH$_2$)$_5$— | | O | —NHSO$_2$NHCOCH$_2$C$_6$H$_5$ | Cl,n-Pr | |
| 395 | n-Pr | —(CH$_2$)S(CH$_2$)$_2$— | | O | —CONHSO$_2$CH$_2$C$_6$H$_5$ | H,H | |
| 396 | n-Pr | —(CH$_2$)S(CH$_2$)$_2$— | | O | —SO$_2$NHCOC$_6$H$_5$ | H,H | |
| 397 | n-Pr | —(CH$_2$)S(CH$_2$)$_2$— | | O | —SO$_2$NHCO(n-C$_5$H$_{11}$) | H,H | |
| 398 | n-Pr | —(CH$_2$)S(CH$_2$)$_2$— | | O | —SO$_2$NHCO(cy-C$_3$H$_5$) | H,H | |
| 399 | n-Pr | —(CH$_2$)S(CH$_2$)$_2$— | | O | —SO$_2$NHCOCH$_2$C$_6$H$_5$ | H,H | |
| 400 | n-Pr | —(CH$_2$)S(CH$_2$)$_2$— | | O | —NHSO$_2$NHCO(n-Bu) | H,H | |
| 401 | n-Pr | —(CH$_2$)S(CH$_2$)$_2$— | | O | —NHSO$_2$NHCO(i-Bu) | H,H | |
| 402 | n-Pr | —(CH$_2$)S(CH$_2$)$_2$— | | O | —NHSO$_2$NHCO(n-C$_5$H$_{11}$) | H,H | |
| 403 | n-Pr | —(CH$_2$)S(CH$_2$)$_2$— | | O | —NHSO$_2$NHCO(i-C$_5$H$_{11}$) | H,H | |
| 404 | n-Pr | —(CH$_2$)S(CH$_2$)$_2$— | | O | —NHSO$_2$NHCO(cy-C$_3$H$_5$) | H,H | |
| 405 | n-Pr | —(CH$_2$)S(CH$_2$)$_2$— | | O | —NHSO$_2$NHCOCH$_2$C$_6$H$_5$ | H,H | |
| 406 | n-Pr | —(CH$_2$)S(CH$_2$)$_2$— | | O | —SO$_2$NHCOC$_6$H$_5$ | CH$_3$,H | |
| 407 | n-Pr | —(CH$_2$)S(CH$_2$)$_2$— | | O | —SO$_2$NHCO(n-C$_5$H$_{11}$) | CH$_3$,H | |
| 408 | n-Pr | —(CH$_2$)S(CH$_2$)$_2$— | | O | —SO$_2$NHCO(cy-C$_3$H$_5$) | CH$_3$,H | |
| 409 | n-Pr | —(CH$_2$)S(CH$_2$)$_2$— | | O | —SO$_2$NHCOCH$_2$C$_6$H$_5$ | CH$_3$,H | |
| 410 | n-Pr | —(CH$_2$)S(CH$_2$)$_2$— | | O | —NHSO$_2$NHCO(n-Bu) | CH$_3$,H | |
| 411 | n-Pr | —(CH$_2$)S(CH$_2$)$_2$— | | O | —SO$_2$NHCONH(n-Bu) | CH$_3$,H | |
| 412 | n-Pr | —(CH$_2$)S(CH$_2$)$_2$— | | O | —NHSO$_2$NHCO(i-Bu) | CH$_3$,H | |
| 413 | n-Pr | —(CH$_2$)S(CH$_2$)$_2$— | | O | —NHSO$_2$NHCO(n-C$_5$H$_{11}$) | CH$_3$,H | |
| 414 | n-Pr | —(CH$_2$)S(CH$_2$)$_2$— | | O | —NHSO$_2$NHCO(i-C$_5$H$_{11}$) | CH$_3$,H | |
| 415 | n-Pr | —(CH$_2$)S(CH$_2$)$_2$— | | O | —NHSO$_2$NHCO(cy-C$_3$H$_5$) | CH$_3$,H | |
| 416 | n-Pr | —(CH$_2$)S(CH$_2$)$_2$— | | O | —NHSO$_2$NHCOCH$_2$C$_6$H$_5$ | CH$_3$,H | |
| 417 | n-Pr | —(CH$_2$)S(CH$_2$)$_2$— | | O | —SO$_2$NHCOC$_6$H$_5$ | Cl,H | |
| 418 | n-Pr | —(CH$_2$)S(CH$_2$)$_2$— | | O | —SO$_2$NHCO(n-C$_5$H$_{11}$) | Cl,H | |
| 419 | n-Pr | —(CH$_2$)S(CH$_2$)$_2$— | | O | —SO$_2$NHCO(cy-C$_3$H$_5$) | Cl,H | |
| 420 | n-Pr | —(CH$_2$)S(CH$_2$)$_2$— | | O | —SO$_2$NHCOCH$_2$C$_6$H$_5$ | Cl,H | |
| 421 | n-Pr | —(CH$_2$)S(CH$_2$)$_2$— | | O | —NHSO$_2$NHCO(n-Bu) | Cl,H | |
| 422 | n-Pr | —(CH$_2$)S(CH$_2$)$_2$— | | O | —NHSO$_2$NHCO(n-Bu) | Cl,H | |
| 423 | n-Pr | —(CH$_2$)S(CH$_2$)$_2$— | | O | —SO$_2$NHCONH(i-Bu) | Cl,H | |
| 424 | n-Pr | —(CH$_2$)S(CH$_2$)$_2$— | | O | —NHSO$_2$NHCO(n-C$_5$H$_{11}$) | Cl,H | |
| 425 | n-Pr | —(CH$_2$)S(CH$_2$)$_2$— | | O | —NHSO$_2$NHCO(i-C$_5$H$_{11}$) | Cl,H | |
| 426 | n-Pr | —(CH$_2$)S(CH$_2$)$_2$— | | O | —NHSO$_2$NHCO(cy-C$_3$H$_5$) | Cl,H | |
| 427 | n-Pr | —(CH$_2$)S(CH$_2$)$_2$— | | O | —NHSO$_2$NHCOCH$_2$C$_6$H$_5$ | Cl,H | |

TABLE 1-continued

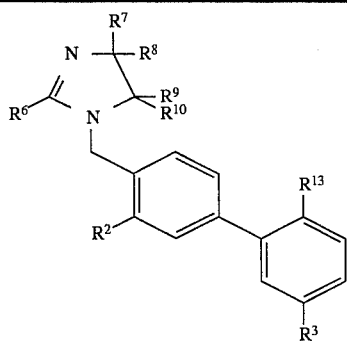

| Ex. | $R^6$ | $R^7$ $R^8$ | $R^9, R^{10}$ | $R^{13}$ | $R^2, R^3$ | MS(M + H)$^+$ |
|---|---|---|---|---|---|---|
| 428 | n-Pr | —(CH$_2$)S(CH$_2$)$_2$— | O | —SO$_2$NHCOC$_6$H$_5$ | F,H | |
| 429 | n-Pr | —(CH$_2$)S(CH$_2$)$_2$— | O | —SO$_2$NHCO(n-C$_5$H$_{11}$) | F,H | |
| 430 | n-Pr | —(CH$_2$)S(CH$_2$)$_2$— | O | —SO$_2$NHCO(cy-C$_3$H$_5$) | F,H | |
| 431 | n-Pr | —(CH$_2$)S(CH$_2$)$_2$— | O | —SO$_2$NHCOCH$_2$C$_6$H$_5$ | F,H | |
| 432 | n-Pr | —(CH$_2$)S(CH$_2$)$_2$— | O | —NHSO$_2$NHCO(n-Bu) | F,H | |
| 433 | n-Pr | —(CH$_2$)S(CH$_2$)$_2$— | O | —SO$_2$NHCONH(n-Bu) | F,H | |
| 434 | n-Pr | —(CH$_2$)S(CH$_2$)$_2$— | O | —NHSO$_2$NHCO(i-Bu) | F,H | |
| 435 | n-Pr | —(CH$_2$)S(CH$_2$)$_2$— | O | —NHSO$_2$NHCO(n-C$_5$H$_{11}$) | F,H | |
| 436 | n-Pr | —(CH$_2$)S(CH$_2$)$_2$— | O | —NHSO$_2$NHCO(i-C$_5$H$_{11}$) | F,H | |
| 437 | n-Pr | —(CH$_2$)S(CH$_2$)$_2$— | O | —NHSO$_2$NHCO(cy-C$_3$H$_5$) | F,H | |
| 438 | n-Pr | —(CH$_2$)S(CH$_2$)$_2$— | O | —NHSO$_2$NHCOCH$_2$C$_6$H$_5$ | F,H | |
| 439 | n-Pr | —(CH$_2$)S(CH$_2$)$_2$— | O | —SO$_2$NHCOC$_6$H$_5$ | H,n-Pr | |
| 440 | n-Pr | —(CH$_2$)S(CH$_2$)$_2$— | O | —SO$_2$NHCO(n-C$_5$H$_{11}$) | H,n-Pr | |
| 441 | n-Pr | —(CH$_2$)S(CH$_2$)$_2$— | O | —SO$_2$NHCO(cy-C$_3$H$_5$) | H,n-Pr | |
| 442 | n-Pr | —(CH$_2$)S(CH$_2$)$_2$— | O | —SO$_2$NHCOCH$_2$C$_6$H$_5$ | H,n-Pr | |
| 443 | n-Pr | —(CH$_2$)S(CH$_2$)$_2$— | O | —NHSO$_2$NHCO(n-Bu) | H,n-Pr | |
| 444 | n-Pr | —(CH$_2$)S(CH$_2$)$_2$— | O | —SO$_2$NHCONH(n-Bu) | H,n-Pr | |
| 445 | n-Pr | —(CH$_2$)S(CH$_2$)$_2$— | O | —NHSO$_2$NHCO(i-Bu) | H,n-Pr | |
| 446 | n-Pr | —(CH$_2$)S(CH$_2$)$_2$— | O | —NHSO$_2$NHCO(n-C$_5$H$_{11}$) | H,n-Pr | |
| 447 | n-Pr | —(CH$_2$)S(CH$_2$)$_2$— | O | —NHSO$_2$NHCO(i-C$_5$H$_{11}$) | H,n-Pr | |
| 448 | n-Pr | —(CH$_2$)S(CH$_2$)$_2$— | O | —NHSO$_2$NHCO(cy-C$_3$H$_5$) | H,n-Pr | |
| 449 | n-Pr | —(CH$_2$)S(CH$_2$)$_2$— | O | —NHSO$_2$NHCOCH$_2$C$_6$H$_5$ | H,n-Pr | |
| 450 | n-Pr | —(CH$_2$)S(CH$_2$)$_2$— | O | —SO$_2$NHCOC$_6$H$_5$ | Cl,n-Pr | |
| 451 | n-Pr | —(CH$_2$)S(CH$_2$)$_2$— | O | —SO$_2$NHCO(n-C$_5$H$_{11}$) | Cl,n-Pr | |
| 452 | n-Pr | —(CH$_2$)S(CH$_2$)$_2$— | O | —SO$_2$NHCO(cy-C$_3$H$_5$) | F,n-Pr | |
| 453 | n-Pr | —(CH$_2$)S(CH$_2$)$_2$— | O | —SO$_2$NHCOCH$_2$C$_6$H$_5$ | F,n-Pr | |
| 454 | n-Pr | —(CH$_2$)S(CH$_2$)$_2$— | O | —NHSO$_2$NHCO(n-Bu) | Cl,n-Pr | |
| 455 | n-Pr | —(CH$_2$)S(CH$_2$)$_2$— | O | —SO$_2$NHCONH(n-Bu) | Cl,n-Pr | |
| 456 | n-Pr | —(CH$_2$)S(CH$_2$)$_2$— | O | —NHSO$_2$NHCO(i-Bu) | F,n-Pr | |
| 457 | n-Pr | —(CH$_2$)S(CH$_2$)$_2$— | O | —NHSO$_2$NHCO(n-C$_5$H$_{11}$) | Cl,n-Pr | |
| 458 | n-Pr | —(CH$_2$)S(CH$_2$)$_2$— | O | —NHSO$_2$NHCO(i-C$_5$H$_{11}$) | F,n-Pr | |
| 459 | n-Pr | —(CH$_2$)S(CH$_2$)$_2$— | O | —NHSO$_2$NHCO(cy-C$_3$H$_5$) | F,n-Pr | |
| 460 | n-Pr | —(CH$_2$)S(CH$_2$)$_2$— | O | —NHSO$_2$NHCOCH$_2$C$_6$H$_5$ | Cl,n-Pr | |
| 461 | n-Bu | —(CH$_2$)S(CH$_2$)$_2$— | O | —SO$_2$NHCOC$_6$H$_5$ | H,H | |
| 462 | n-Bu | —(CH$_2$)S(CH$_2$)$_2$— | O | —SO$_2$NHCO(n-C$_5$H$_{11}$) | H,H | |
| 463 | n-Bu | —(CH$_2$)S(CH$_2$)$_2$— | O | —SO$_2$NHCO(cy-C$_3$H$_5$) | H,H | |
| 464 | n-Bu | —(CH$_2$)S(CH$_2$)$_2$— | O | —SO$_2$NHCOCH$_2$C$_6$H$_5$ | H,H | |
| 465 | n-Bu | —(CH$_2$)S(CH$_2$)$_2$— | O | —NHSO$_2$NHCO(n-Bu) | H,H | |
| 466 | n-Bu | —(CH$_2$)S(CH$_2$)$_2$— | O | —NHSO$_2$NHCO(i-Bu) | H,H | |
| 467 | n-Bu | —(CH$_2$)S(CH$_2$)$_2$— | O | —NHSO$_2$NHCO(n-C$_5$H$_{11}$) | H,H | |
| 468 | n-Bu | —(CH$_2$)S(CH$_2$)$_2$— | O | —NHSO$_2$NHCO(i-C$_5$H$_{11}$) | H,H | |
| 469 | n-Bu | —(CH$_2$)S(CH$_2$)$_2$— | O | —NHSO$_2$NHCO(cy-C$_3$H$_5$) | H,H | |
| 470 | n-Bu | —(CH$_2$)S(CH$_2$)$_2$— | O | —NHSO$_2$NHCOCH$_2$C$_6$H$_5$ | H,H | |
| 471 | n-Bu | —(CH$_2$)S(CH$_2$)$_2$— | O | —SO$_2$NHCOC$_6$H$_5$ | CH$_3$,H | |
| 472 | n-Bu | —(CH$_2$)S(CH$_2$)$_2$— | O | —SO$_2$NHCO(n-C$_5$H$_{11}$) | CH$_3$,H | |
| 473 | n-Bu | —(CH$_2$)S(CH$_2$)$_2$— | O | —SO$_2$NHCO(cy-C$_3$H$_5$) | CH$_3$,H | |
| 474 | n-Bu | —(CH$_2$)S(CH$_2$)$_2$— | O | —SO$_2$NHCOCH$_2$C$_6$H$_5$ | CH$_3$,H | |
| 475 | n-Bu | —(CH$_2$)S(CH$_2$)$_2$— | O | —NHSO$_2$NHCO(n-Bu) | CH$_3$,H | |
| 476 | n-Bu | —(CH$_2$)S(CH$_2$)$_2$— | O | —SO$_2$NHCONH(n-Bu) | CH$_3$,H | |
| 477 | n-Bu | —(CH$_2$)S(CH$_2$)$_2$— | O | —NHSO$_2$NHCO(i-Bu) | CH$_3$,H | |
| 478 | n-Bu | —(CH$_2$)S(CH$_2$)$_2$— | O | —NHSO$_2$NHCO(n-C$_5$H$_{11}$) | CH$_3$,H | |
| 479 | n-Bu | —(CH$_2$)S(CH$_2$)$_2$— | O | —NHSO$_2$NHCO(i-C$_5$H$_{11}$) | CH$_3$,H | |
| 480 | n-Bu | —(CH$_2$)S(CH$_2$)$_2$— | O | —NHSO$_2$NHCO(cy-C$_3$H$_5$) | CH$_3$,H | |
| 481 | n-Bu | —(CH$_2$)S(CH$_2$)$_2$— | O | —NHSO$_2$NHCOCH$_2$C$_6$H$_5$ | CH$_3$,H | |
| 482 | n-Bu | —(CH$_2$)S(CH$_2$)$_2$— | O | —SO$_2$NHCOC$_6$H$_5$ | Cl,H | |
| 483 | n-Bu | —(CH$_2$)S(CH$_2$)$_2$— | O | —SO$_2$NHCO(n-C$_5$H$_{11}$) | Cl,H | |
| 484 | n-Bu | —(CH$_2$)S(CH$_2$)$_2$— | O | —SO$_2$NHCO(cy-C$_3$H$_5$) | Cl,H | |
| 485 | n-Bu | —(CH$_2$)S(CH$_2$)$_2$— | O | —SO$_2$NHCOCH$_2$C$_6$H$_5$ | Cl,H | |
| 486 | n-Bu | —(CH$_2$)S(CH$_2$)$_2$— | O | —NHSO$_2$NHCO(n-Bu) | Cl,H | |
| 487 | n-Bu | —(CH$_2$)S(CH$_2$)$_2$— | O | —NHSO$_2$NHCO(i-Bu) | Cl,H | |
| 488 | n-Bu | —(CH$_2$)S(CH$_2$)$_2$— | O | —NHSO$_2$NHCO(n-C$_5$H$_{11}$) | Cl,H | |

TABLE 1-continued

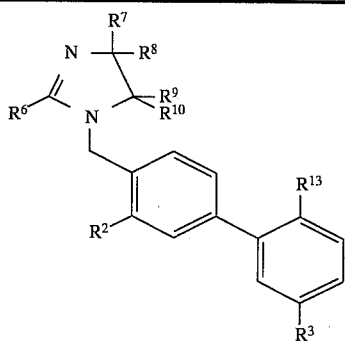

| Ex. | R⁶ | R⁷ | R⁸ | R⁹, R¹⁰ | R¹³ | R², R³ | MS(M + H)⁺ |
|---|---|---|---|---|---|---|---|
| 489 | n-Bu | —(CH$_2$)S(CH$_2$)$_2$— | | O | —SO$_2$NHCONH(n-C$_5$H$_{11}$) | Cl,H | |
| 490 | n-Bu | —(CH$_2$)S(CH$_2$)$_2$— | | O | —NHSO$_2$NHCO(i-C$_5$H$_{11}$) | Cl,H | |
| 491 | n-Bu | —(CH$_2$)S(CH$_2$)$_2$— | | O | —NHSO$_2$NHCO(cy-C$_3$H$_5$) | Cl,H | |
| 492 | n-Bu | —(CH$_2$)S(CH$_2$)$_2$— | | O | —NHSO$_2$NHCOCH$_2$C$_6$H$_5$ | Cl,H | |
| 493 | n-Bu | —(CH$_2$)S(CH$_2$)$_2$— | | O | —SO$_2$NHCOC$_6$H$_5$ | F,H | |
| 494 | n-Bu | —(CH$_2$)S(CH$_2$)$_2$— | | O | —SO$_2$NHCO(n-C$_5$H$_{11}$) | F,H | |
| 495 | n-Bu | —(CH$_2$)S(CH$_2$)$_2$— | | O | —SO$_2$NHCO(cy-C$_3$H$_5$) | F,H | |
| 496 | n-Bu | —(CH$_2$)S(CH$_2$)$_2$— | | O | —SO$_2$NHCOCH$_2$C$_6$H$_5$ | F,H | |
| 497 | n-Bu | —(CH$_2$)S(CH$_2$)$_2$— | | O | —NHSO$_2$NHCO(n-Bu) | F,H | |
| 498 | n-Bu | —(CH$_2$)S(CH$_2$)$_2$— | | O | —NHSO$_2$NHCO(i-Bu) | F,H | |
| 499 | n-Bu | —(CH$_2$)S(CH$_2$)$_2$— | | O | —NHSO$_2$NHCO(n-C$_5$H$_{11}$) | F,H | |
| 500 | n-Bu | —(CH$_2$)S(CH$_2$)$_2$— | | O | —SO$_2$NHCONH(n-C$_5$H$_{11}$) | F,H | |
| 501 | n-Bu | —(CH$_2$)S(CH$_2$)$_2$— | | O | —NHSO$_2$NHCO(i-C$_5$H$_{11}$) | F,H | |
| 502 | n-Bu | —(CH$_2$)S(CH$_2$)$_2$— | | O | —NHSO$_2$NHCO(cy-C$_3$H$_5$) | F,H | |
| 503 | n-Bu | —(CH$_2$)S(CH$_2$)$_2$— | | O | —NHSO$_2$NHCOCH$_2$C$_6$H$_5$ | F,H | |
| 504 | n-Bu | —(CH$_2$)S(CH$_2$)$_2$— | | O | —SO$_2$NHCOC$_6$H$_5$ | H,n-Pr | |
| 505 | n-Bu | —(CH$_2$)S(CH$_2$)$_2$— | | O | —SO$_2$NHCO(n-C$_5$H$_{11}$) | H,n-Pr | |
| 506 | n-Bu | —(CH$_2$)S(CH$_2$)$_2$— | | O | —SO$_2$NHCO(cy-C$_3$H$_5$) | H,n-Pr | |
| 507 | n-Bu | —(CH$_2$)S(CH$_2$)$_2$— | | O | —SO$_2$NHCOCH$_2$C$_6$H$_5$ | H,n-Pr | |
| 508 | n-Bu | —(CH$_2$)S(CH$_2$)$_2$— | | O | —NHSO$_2$NHCO(n-Bu) | H,n-Pr | |
| 509 | n-Bu | —(CH$_2$)S(CH$_2$)$_2$— | | O | —NHSO$_2$NHCO(i-Bu) | H,n-Pr | |
| 510 | n-Bu | —(CH$_2$)S(CH$_2$)$_2$— | | O | —SO$_2$NHCONH(n-C$_5$H$_{11}$) | H,n-Pr | |
| 511 | n-Bu | —(CH$_2$)S(CH$_2$)$_2$— | | O | —NHSO$_2$NHCO(n-C$_5$H$_{11}$) | H,n-Pr | |
| 512 | n-Bu | —(CH$_2$)S(CH$_2$)$_2$— | | O | —NHSO$_2$NHCO(i-C$_5$H$_{11}$) | H,n-Pr | |
| 513 | n-Bu | —(CH$_2$)S(CH$_2$)$_2$— | | O | —NHSO$_2$NHCO(cy-C$_3$H$_5$) | H,n-Pr | |
| 514 | n-Bu | —(CH$_2$)S(CH$_2$)$_2$— | | O | —NHSO$_2$NHCOCH$_2$C$_6$H$_5$ | H,n-Pr | |
| 515 | n-Bu | —(CH$_2$)S(CH$_2$)$_2$— | | O | —SO$_2$NHCOC$_6$H$_5$ | Cl,n-Pr | |
| 516 | n-Bu | —(CH$_2$)S(CH$_2$)$_2$— | | O | —SO$_2$NHCO(n-C$_5$H$_{11}$) | Cl,n-Pr | |
| 517 | n-Bu | —(CH$_2$)S(CH$_2$)$_2$— | | O | —SO$_2$NHCO(cy-C$_3$H$_5$) | F,n-Pr | |
| 518 | n-Bu | —(CH$_2$)S(CH$_2$)$_2$— | | O | —SO$_2$NHCOCH$_2$C$_6$H$_5$ | F,n-Pr | |
| 519 | n-Bu | —(CH$_2$)S(CH$_2$)$_2$— | | O | —NHSO$_2$NHCO(n-Bu) | Cl,n-Pr | |
| 520 | n-Bu | —(CH$_2$)S(CH$_2$)$_2$— | | O | —SO$_2$NHCONH(n-Bu) | Cl,n-Pr | |
| 521 | n-Bu | —(CH$_2$)S(CH$_2$)$_2$— | | O | —SO$_2$NHCONH(i-Bu) | Cl,n-Pr | |
| 522 | n-Bu | —(CH$_2$)S(CH$_2$)$_2$— | | O | —NHSO$_2$NHCO(i-Bu) | F,n-Pr | |
| 523 | n-Bu | —(CH$_2$)S(CH$_2$)$_2$— | | O | —NHSO$_2$NHCO(n-C$_5$H$_{11}$) | Cl,n-Pr | |
| 524 | n-Bu | —(CH$_2$)S(CH$_2$)$_2$— | | O | —NHSO$_2$NHCO(i-C$_5$H$_{11}$) | F,n-Pr | |
| 525 | n-Bu | —(CH$_2$)S(CH$_2$)$_2$— | | O | —NHSO$_2$NHCO(cy-C$_3$H$_5$) | F,n-Pr | |
| 526 | n-Bu | —(CH$_2$)S(CH$_2$)$_2$— | | O | —NHSO$_2$NHCOCH$_2$C$_6$H$_5$ | Cl,n-Pr | |
| 527 | n-Pr | —(CH$_2$)O(CH$_2$)$_2$— | | O | —CONHSO$_2$CH$_2$C$_6$H$_5$ | H,H | |
| 528 | n-Pr | —(CH$_2$)O(CH$_2$)$_2$— | | O | —SO$_2$NHCOC$_6$H$_5$ | H,H | |
| 529 | n-Pr | —(CH$_2$)O(CH$_2$)$_2$— | | O | —SO$_2$NHCO(n-C$_5$H$_{11}$) | H,H | |
| 530 | n-Pr | —(CH$_2$)O(CH$_2$)$_2$— | | O | —SO$_2$NHCO(cy-C$_3$H$_5$) | H,H | |
| 531 | n-Pr | —(CH$_2$)O(CH$_2$)$_2$— | | O | —SO$_2$NHCOCH$_2$C$_6$H$_5$ | H,H | |
| 532 | n-Pr | —(CH$_2$)O(CH$_2$)$_2$— | | O | —NHSO$_2$NHCO(n-Bu) | H,H | |
| 533 | n-Pr | —(CH$_2$)O(CH$_2$)$_2$— | | O | —NHSO$_2$NHCO(i-Bu) | H,H | |
| 534 | n-Pr | —(CH$_2$)O(CH$_2$)$_2$— | | O | —NHSO$_2$NHCO(n-C$_5$H$_{11}$) | H,H | |
| 535 | n-Pr | —(CH$_2$)O(CH$_2$)$_2$— | | O | —NHSO$_2$NHCO(i-C$_5$H$_{11}$) | H,H | |
| 536 | n-Pr | —(CH$_2$)O(CH$_2$)$_2$— | | O | —NHSO$_2$NHCO(cy-C$_3$H$_5$) | H,H | |
| 537 | n-Pr | —(CH$_2$)O(CH$_2$)$_2$— | | O | —NHSO$_2$NHCOCH$_2$C$_6$H$_5$ | H,H | |
| 538 | n-Pr | —(CH$_2$)O(CH$_2$)$_2$— | | O | —CONHSO$_2$CH$_2$C$_6$H$_5$ | H,H | |
| 539 | n-Pr | —(CH$_2$)O(CH$_2$)$_2$— | | O | —SO$_2$NHCOC$_6$H$_5$ | H,H | |
| 540 | n-Pr | —(CH$_2$)O(CH$_2$)$_2$— | | O | —SO$_2$NHCO(n-C$_5$H$_{11}$) | H,H | |
| 541 | n-Pr | —(CH$_2$)O(CH$_2$)$_2$— | | O | —SO$_2$NHCO(cy-C$_3$H$_5$) | H,H | |
| 542 | n-Pr | —(CH$_2$)O(CH$_2$)$_2$— | | O | —SO$_2$NHCOCH$_2$C$_6$H$_5$ | H,H | |
| 543 | n-Pr | —(CH$_2$)O(CH$_2$)$_2$— | | O | —NHSO$_2$NHCO(n-Bu) | H,H | |
| 544 | n-Pr | —(CH$_2$)O(CH$_2$)$_2$— | | O | —NHSO$_2$NHCO(i-Bu) | H,H | |
| 545 | n-Pr | —(CH$_2$)O(CH$_2$)$_2$— | | O | —NHSO$_2$NHCO(n-C$_5$H$_{11}$) | H,H | |
| 546 | n-Pr | —(CH$_2$)O(CH$_2$)$_2$— | | O | —NHSO$_2$NHCO(i-C$_5$H$_{11}$) | H,H | |
| 547 | n-Pr | —(CH$_2$)O(CH$_2$)$_2$— | | O | —NHSO$_2$NHCO(cy-C$_3$H$_5$) | H,H | |
| 548 | n-Pr | —(CH$_2$)O(CH$_2$)$_2$— | | O | —NHSO$_2$NHCOCH$_2$C$_6$H$_5$ | H,H | |
| 549 | n-Pr | —(CH$_2$)SO(CH$_2$)$_2$— | | O | —CONHSO$_2$CH$_2$C$_6$H$_5$ | H,H | |

TABLE 1-continued

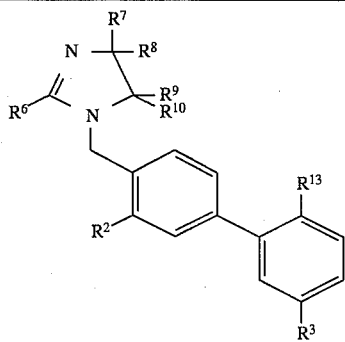

| Ex. | R$^6$ | R$^7$ | R$^8$ | R$^9$, R$^{10}$ | R$^{13}$ | R$^2$, R$^3$ | MS(M + H)$^+$ |
|---|---|---|---|---|---|---|---|
| 550 | n-Pr | —(CH$_2$)SO(CH$_2$)$_2$— | | O | —SO$_2$NHCOC$_6$H$_5$ | H,H | |
| 551 | n-Pr | —(CH$_2$)SO(CH$_2$)$_2$— | | O | —SO$_2$NHCO(n-C$_5$H$_{11}$) | H,H | |
| 552 | n-Pr | —(CH$_2$)SO(CH$_2$)$_2$— | | O | —SO$_2$NHCO(cy-C$_3$H$_5$) | H,H | |
| 553 | n-Pr | —(CH$_2$)SO(CH$_2$)$_2$— | | O | —SO$_2$NHCOCH$_2$C$_6$H$_5$ | H,H | |
| 554 | n-Pr | —(CH$_2$)SO(CH$_2$)$_2$— | | O | —NHSO$_2$NHCO(n-Bu) | H,H | |
| 555 | n-Pr | —(CH$_2$)SO(CH$_2$)$_2$— | | O | —NHSO$_2$NHCO(i-Bu) | H,H | |
| 556 | n-Pr | —(CH$_2$)SO(CH$_2$)$_2$— | | O | —NHSO$_2$NHCO(n-C$_5$H$_{11}$) | H,H | |
| 557 | n-Pr | —(CH$_2$)SO(CH$_2$)$_2$— | | O | —NHSO$_2$NHCO(i-C$_5$H$_{11}$) | H,H | |
| 558 | n-Pr | —(CH$_2$)SO(CH$_2$)$_2$— | | O | —NHSO$_2$NHCO(cy-C$_3$H$_5$) | H,H | |
| 559 | n-Pr | —(CH$_2$)SO(CH$_2$)$_2$— | | O | —NHSO$_2$NHCOCH$_2$C$_6$H$_5$ | H,H | |
| 560 | n-Pr | —(CH$_2$)NCOMe(CH$_2$)$_2$— | | O | —NHSO$_2$CH$_2$C$_6$H$_5$ | H,H | |
| 561 | n-Pr | —(CH$_2$)NCOMe(CH$_2$)$_2$— | | O | —SO$_2$NHCOC$_6$H$_5$ | H,H | |
| 562 | n-Pr | —(CH$_2$)NCOMe(CH$_2$)$_2$— | | O | —SO$_2$NHCO(n-C$_5$H$_{11}$) | H,H | |
| 563 | n-Pr | —(CH$_2$)NCOMe(CH$_2$)$_2$— | | O | —SO$_2$NHCO(cy-C$_3$H$_5$) | H,H | |
| 564 | n-Pr | —(CH$_2$)NCOMe(CH$_2$)$_2$— | | O | —SO$_2$NHCOCH$_2$C$_6$H$_5$ | H,H | |
| 565 | n-Pr | —(CH$_2$)NCOMe(CH$_2$)$_2$— | | O | —NHSO$_2$NHCO(n-Bu) | H,H | |
| 566 | n-Pr | —(CH$_2$)NCOMe(CH$_2$)$_2$— | | O | —NHSO$_2$NHCO(i-Bu) | H,H | |
| 567 | n-Pr | —(CH$_2$)NCOMe(CH$_2$)$_2$— | | O | —NHSO$_2$NHCO(n-C$_5$H$_{11}$) | H,H | |
| 568 | n-Pr | —(CH$_2$)NCOMe(CH$_2$)$_2$— | | O | —NHSO$_2$NHCO(i-C$_5$H$_{11}$) | H,H | |
| 569 | n-Pr | —(CH$_2$)NCOMe(CH$_2$)$_2$— | | O | —NHSO$_2$NHCO(cy-C$_3$H$_5$) | H,H | |
| 570 | n-Pr | —(CH$_2$)NCOMe(CH$_2$)$_2$— | | O | —NHSO$_2$NHCOCH$_2$C$_6$H$_5$ | H,H | |
| 571 | n-Pr | —(CH$_2$)NCOPh(CH$_2$)$_2$— | | O | —CONHSO$_2$CH$_2$C$_6$H$_5$ | H,H | |
| 572 | n-Pr | —(CH$_2$)NCOPh(CH$_2$)$_2$— | | O | —SO$_2$NHCOC$_6$H$_5$ | H,H | |
| 573 | n-Pr | —(CH$_2$)NCOPh(CH$_2$)$_2$— | | O | —SO$_2$NHCO(n-C$_5$H$_{11}$) | H,H | |
| 574 | n-Pr | —(CH$_2$)NCOPh(CH$_2$)$_2$— | | O | —SO$_2$NHCO(cy-C$_3$H$_5$) | H,H | |
| 575 | n-Pr | —(CH$_2$)NCOPh(CH$_2$)$_2$— | | O | —SO$_2$NHCOCH$_2$C$_6$H$_5$ | H,H | |
| 576 | n-Pr | —(CH$_2$)NCOPh(CH$_2$)$_2$— | | O | —NHSO$_2$NHCO(n-Bu) | H,H | |
| 577 | n-Pr | —(CH$_2$)NCOPh(CH$_2$)$_2$— | | O | —NHSO$_2$NHCO(i-Bu) | H,H | |
| 578 | n-Pr | —(CH$_2$)NCOPh(CH$_2$)$_2$— | | O | —NHSO$_2$NHCO(n-C$_5$H$_{11}$) | H,H | |
| 579 | n-Pr | —(CH$_2$)NCOPh(CH$_2$)$_2$— | | O | —NHSO$_2$NHCO(i-C$_5$H$_{11}$) | H,H | |
| 580 | n-Pr | —(CH$_2$)NCOPh(CH$_2$)$_2$— | | O | —NHSO$_2$NHCO(cy-C$_3$H$_5$) | H,H | |
| 581 | n-Pr | —(CH$_2$)NCOPh(CH$_2$)$_2$— | | O | —NHSO$_2$NHCOCH$_2$C$_6$H$_5$ | H,H | |
| 582 | n-Pr | —(CH$_2$)NCH$_2$Ph(CH$_2$)$_2$— | | O | —CONHSO$_2$CH$_2$C$_6$H$_5$ | H,H | |
| 583 | n-Pr | —(CH$_2$)NCH$_2$Ph(CH$_2$)$_2$— | | O | —SO$_2$NHCOC$_6$H$_5$ | H,H | |
| 584 | n-Pr | —(CH$_2$)NCH$_2$Ph(CH$_2$)$_2$— | | O | —SO$_2$NHCO(n-C$_5$H$_{11}$) | H,H | |
| 585 | n-Pr | —(CH$_2$)NCH$_2$Ph(CH$_2$)$_2$— | | O | —SO$_2$NHCO(cy-C$_3$H$_5$) | H,H | |
| 586 | n-Pr | —(CH$_2$)NCH$_2$Ph(CH$_2$)$_2$— | | O | —SO$_2$NHCOCH$_2$C$_6$H$_5$ | H,H | |
| 587 | n-Pr | —(CH$_2$)NCH$_2$Ph(CH$_2$)$_2$— | | O | —NHSO$_2$NHCO(n-Bu) | H,H | |
| 588 | n-Pr | —(CH$_2$)NCH$_2$Ph(CH$_2$)$_2$— | | O | —NHSO$_2$NHCO(i-Bu) | H,H | |
| 589 | n-Pr | —(CH$_2$)NCH$_2$Ph(CH$_2$)$_2$— | | O | —NHSO$_2$NHCO(n-C$_5$H$_{11}$) | H,H | |
| 590 | n-Pr | —(CH$_2$)NCH$_2$Ph(CH$_2$)$_2$— | | O | —NHSO$_2$NHCO(i-C$_5$H$_{11}$) | H,H | |
| 591 | n-Pr | —(CH$_2$)NCH$_2$Ph(CH$_2$)$_2$— | | O | —NHSO$_2$NHCO(cy-C$_3$H$_5$) | H,H | |
| 592 | n-Pr | —(CH$_2$)NCH$_2$Ph(CH$_2$)$_2$— | | O | —NHSO$_2$NHCOCH$_2$C$_6$H$_5$ | H,H | |
| 593 | n-Pr | CF$_3$ | CF$_3$ | O | —SO$_2$NHCOC$_6$H$_5$ | H,H | |
| 594 | n-Pr | CF$_3$ | CF$_3$ | O | —SO$_2$NHCO(n-C$_5$H$_{11}$) | H,H | |
| 595 | n-Pr | CF$_3$ | CF$_3$ | O | —SO$_2$NHCO(cy-C$_3$H$_5$) | H,H | |
| 596 | n-Pr | CF$_3$ | CF$_3$ | O | —SO$_2$NHCOCH$_2$C$_6$H$_5$ | H,H | |
| 597 | n-Pr | CF$_3$ | CF$_3$ | O | —NHSO$_2$NHCO(n-Bu) | H,H | |
| 598 | n-Pr | CF$_3$ | CF$_3$ | O | —NHSO$_2$NHCO(i-Bu) | H,H | |
| 599 | n-Pr | CF$_3$ | CF$_3$ | O | —NHSO$_2$NHCO(n-C$_5$H$_{11}$) | H,H | |
| 600 | n-Pr | CF$_3$ | CF$_3$ | O | —NHSO$_2$NHCO(i-C$_5$H$_{11}$) | H,H | |
| 601 | n-Pr | CF$_3$ | CF$_3$ | O | —NHSO$_2$NHCO(cy-C$_3$H$_5$) | H,H | |
| 602 | n-Pr | CF$_3$ | CF$_3$ | O | —NHSO$_2$NHCOCH$_2$C$_6$H$_5$ | H,H | |
| 603 | n-Pr | Ph | Ph | O | —SO$_2$NHCOC$_6$H$_5$ | H,H | |
| 604 | n-Pr | Ph | Ph | O | —SO$_2$NHCO(n-C$_5$H$_{11}$) | H,H | |
| 605 | n-Pr | Ph | Ph | O | —SO$_2$NHCO(cy-C$_3$H$_5$) | H,H | |
| 606 | n-Pr | Ph | Ph | O | —SO$_2$NHCOCH$_2$C$_6$H$_5$ | H,H | |
| 607 | n-Pr | Ph | Ph | O | —NHSO$_2$NHCO(n-Bu) | H,H | |
| 608 | n-Pr | Ph | Ph | O | —NHSO$_2$NHCO(i-Bu) | H,H | |
| 609 | n-Pr | Ph | Ph | O | —NHSO$_2$NHCO(n-C$_5$H$_{11}$) | H,H | |
| 610 | n-Pr | Ph | Ph | O | —NHSO$_2$NHCO(i-C$_5$H$_{11}$) | H,H | |

TABLE 1-continued

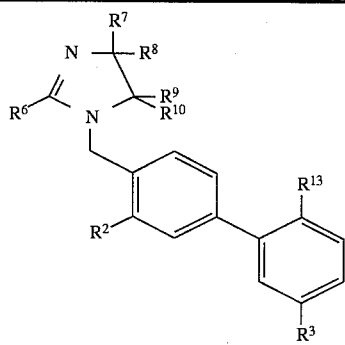

| Ex. | R⁶ | R⁷ | R⁸ | R⁹, R¹⁰ | R¹³ | R², R³ | MS(M + H)⁺ |
|---|---|---|---|---|---|---|---|
| 611 | n-Pr | Ph | Ph | | O | —NHSO$_2$NHCO(cy-C$_3$H$_5$) | H,H | |
| 612 | n-Pr | Ph | Ph | | O | —NHSO$_2$NHCOCH$_2$C$_6$H$_5$ | H,H | |
| 613 | n-Pr | | —(CH$_2$)$_2$— | | O | —SO$_2$NHCOC$_6$H$_5$ | H,H | |
| 614 | n-Pr | | —(CH$_2$)$_2$— | | O | —SO$_2$NHCO(n-C$_5$H$_{11}$) | H,H | |
| 615 | n-Pr | | —(CH$_2$)$_2$— | | O | —SO$_2$NHCO(cy-C$_3$H$_5$) | H,H | |
| 616 | n-Pr | | —(CH$_2$)$_2$— | | O | —SO$_2$NHCOCH$_2$C$_6$H$_5$ | H,H | |
| 617 | n-Pr | | —(CH$_2$)$_2$— | | O | —NHSO$_2$NHCO(n-Bu) | H,H | |
| 618 | n-Pr | | —(CH$_2$)$_2$— | | O | —NHSO$_2$NHCO(i-Bu) | H,H | |
| 619 | n-Pr | | —(CH$_2$)$_2$— | | O | —NHSO$_2$NHCO(n-C$_5$H$_{11}$) | H,H | |
| 620 | n-Pr | | —(CH$_2$)$_2$— | | O | —NHSO$_2$NHCO(i-C$_5$H$_{11}$) | H,H | |
| 621 | n-Pr | | —(CH$_2$)$_2$— | | O | —NHSO$_2$NHCO(cy-C$_3$H$_5$) | H,H | |
| 622 | n-Pr | | —(CH$_2$)$_2$— | | O | —NHSO$_2$NHCOCH$_2$C$_6$H$_5$ | H,H | |
| 623 | n-Pr | CH$_3$ | CH$_3$ | | S | —SO$_2$NHCOC$_6$H$_5$ | H,H | |
| 624 | n-Pr | CH$_3$ | CH$_3$ | | S | —CONHSO$_2$CH$_2$C$_6$H$_5$ | H,H | |
| 625 | n-Pr | CH$_3$ | CH$_3$ | | S | —SO$_2$NHCO(n-C$_5$H$_{11}$) | H,H | |

EXAMPLE 626

N-((4'-(((4-oxo-2-propyl-1,3-diazaspiro((4.4))non-1-en-3-yl)methyl))((1,1'-biphenyl-2-ylsulfonyl))-carbamicacid(n-butyl)ester N-((4'-(((4-oxo-2propyl-1,3-diazaspiro((4.4))non-1-en-3-yl-methyl))((1,1'-biphenyl-2-ylsulfonyl))-2-sulfonamide (100 mg, 0.20 mmol) was dissolved in methylene chloride (10 mL). 4-Dimethylaminopyridine (32 mg, 0.22 mmol) and pyridine(1 mL) were added. n-Butyl chloroformate (0.1 mL, 0.6 mmol) was added dropwise. The reaction mixture was allowed to stir at room temperature under N$_2$ overnight. The mixture was diluted with methylene chloride and washed with water and brine. It was filtered through phase separator paper and concentrated. The residue was chromatographed on silica gel eluting first with ethyl acetate-methylene chloride (1:1) and then with methanol- methylene chloride (5%) to give 45 mg of light yellow foam. MS m/e 526.2 (M+H)⁺, ¹HNMR (CDCl$_3$/TMS) δ0.86 (t, 3H, CH$_3$), 0.95 (t, 3H, CH$_3$), 1.22 (m, 2H, CH$_2$), 1.48 (m, 2H,CH$_2$), 1.69 (m, 2H, CH$_2$), 1.80–2.18 (m, 8H, CH$_2$), 2.37 (t, 2H, CH$_2$), 4.01 (t, 2H, CH$_2$), 4.77 (s, 2H, ArCH$_2$), 7.18–7.36 (m, 5H, ArH), 7.50–7.70 (m, 2H, ArH), 8.24 (d, 1H,t ArH).

Compounds 626–982 in Table 2 can be prepared by the procedures described in Examples 1, 2 and 626 employing the appropriately substituted imidazolines and benzyl halides or mesylates.

TABLE 2

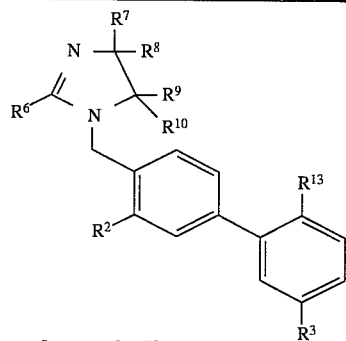

| Ex. | R⁶ | R⁷ | R⁸ | R⁹, R¹⁰ | R¹³ | R², R³ | MS(M + H)⁺ |
|---|---|---|---|---|---|---|---|
| 626 | n-Pr | | —(CH$_2$)$_4$— | | O | —SO$_2$NHCO$_2$(n-C$_4$H$_9$) | H,H | 526 |
| 627 | n-Pr | CH$_3$ | CH$_3$ | | O | —SO$_2$NHCO$_2$(n-C$_4$H$_9$) | H,H | |
| 628 | n-Pr | CH$_3$ | CH$_3$ | | O | —SO$_2$NHCO$_2$(n-C$_4$H$_9$) | H,H | |
| 629 | n-Pr | CH$_3$ | CH$_3$ | | O | —SO$_2$NHCO$_2$(n-C$_5$H$_{11}$) | H,H | |

TABLE 2-continued

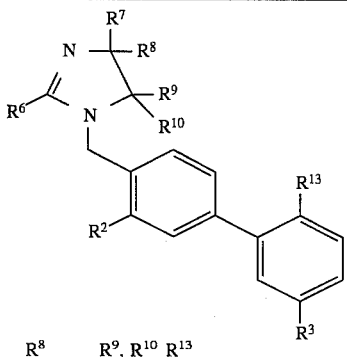

| Ex. | R6 | R7 | R8 | R9, R10 | R13 | R2, R3 | MS(M + H)+ |
|---|---|---|---|---|---|---|---|
| 630 | n-Pr | CH3 | CH3 | O | —SO2NHCO2(i-C5H11) | H,H | |
| 631 | n-Pr | CH3 | CH3 | O | —SO2NHCO2(cy-C3H5) | H,H | |
| 632 | n-Pr | CH3 | CH3 | O | —SO2NHCO2CH2C6H5 | H,H | |
| 633 | n-Pr | CH3 | CH3 | O | —SO2NHCO2(n-C4H9) | CH3,H | |
| 634 | n-Pr | CH3 | CH3 | O | —SO2NHCO2(i-C4H9) | CH3,H | |
| 635 | n-Pr | CH3 | CH3 | O | —SO2NHCO2(n-C5H11) | CH3,H | |
| 636 | n-Pr | CH3 | CH3 | O | —SO2NHCO2(i-C5H11) | CH3,H | |
| 637 | n-Pr | CH3 | CH3 | O | —SO2NHCO2(cy-C3H5) | CH3,H | |
| 638 | n-Pr | CH3 | CH3 | O | —SO2NHCO2CH2C6H5 | CH3,H | |
| 639 | n-Pr | CH3 | CH3 | O | —SO2NHCO2(n-C4H9) | Cl,H | |
| 640 | n-Pr | CH3 | CH3 | O | —SO2NHCO2(i-C4H9) | Cl,H | |
| 641 | n-Pr | CH3 | CH3 | O | —SO2NHCO2(n-C5H11) | Cl,H | |
| 642 | n-Pr | CH3 | CH3 | O | —SO2NHCO2(i-C5H11) | Cl,H | |
| 643 | n-Pr | CH3 | CH3 | O | —SO2NHCO2(cy-C3H5) | Cl,H | |
| 644 | n-Pr | CH3 | CH3 | O | —SO2NHCO2CH2C6H5 | Cl,H | |
| 645 | n-Pr | CH3 | CH3 | O | —SO2NHCO2(n-C4H9) | F,H | |
| 646 | n-Pr | CH3 | CH3 | O | —SO2NHCO2(i-C4H9) | F,H | |
| 647 | n-Pr | CH3 | CH3 | O | —SO2NHCO2(n-C5H11) | F,H | |
| 648 | n-Pr | CH3 | CH3 | O | —SO2NHCO2(i-C5H11) | F,H | |
| 649 | n-Pr | CH3 | CH3 | O | —SO2NHCO2(cy-C3H5) | F,H | |
| 650 | n-Pr | CH3 | CH3 | O | —SO2NHCO2CH2C6H5 | F,H | |
| 651 | n-Pr | CH3 | CH3 | O | —SO2NHCO2(n-C4H9) | H,n-Pr | |
| 652 | n-Pr | CH3 | CH3 | O | —SO2NHCO2(i-C4H9) | H,n-Pr | |
| 653 | n-Pr | CH3 | CH3 | O | —SO2NHCO2(n-C5H11) | H,n-Pr | |
| 654 | n-Pr | CH3 | CH3 | O | —SO2NHCO2(i-C5H11) | H,n-Pr | |
| 655 | n-Pr | CH3 | CH3 | O | —SO2NHCO2(cy-C3H5) | H,n-Pr | |
| 656 | n-Pr | CH3 | CH3 | O | —SO2NHCO2CH2C6H5 | H,n-Pr | |
| 657 | n-Pr | CH3 | CH3 | O | —SO2NHCO2(n-C4H9) | Cl,n-Pr | |
| 658 | n-Pr | CH3 | CH3 | O | —SO2NHCO2(i-C4H9) | F,n-Pr | |
| 659 | n-Pr | CH3 | CH3 | O | —SO2NHCO2(n-C5H11) | Cl,n-Pr | |
| 660 | n-Pr | CH3 | CH3 | O | —SO2NHCO2(i-C5H11) | F,n-Pr | |
| 661 | n-Pr | CH3 | CH3 | O | —SO2NHCO2(cy-C3H5) | F,n-Pr | |
| 662 | n-Pr | CH3 | CH3 | O | —SO2NHCO2CH2C6H5 | Cl,n-Pr | |
| 663 | n-Bu | CH3 | CH3 | O | —SO2NHCO2(n-C4H9) | H,H | |
| 664 | n-Bu | CH3 | CH3 | O | —SO2NHCO2(i-C4H9) | H,H | |
| 665 | n-Bu | CH3 | CH3 | O | —SO2NHCO2(n-C5H11) | H,H | |
| 666 | n-Bu | CH3 | CH3 | O | —SO2NHCO2(i-C5H11) | H,H | |
| 667 | n-Bu | CH3 | CH3 | O | —SO2NHCO2(cy-C3H5) | H,H | |
| 668 | n-Bu | CH3 | CH3 | O | —SO2NHCO2CH2C6H5 | H,H | |
| 669 | n-Bu | CH3 | CH3 | O | —SO2NHCO2(n-C4H9) | CH3,H | |
| 670 | n-Bu | CH3 | CH3 | O | —SO2NHCO2(i-C4H9) | CH3,H | |
| 671 | n-Bu | CH3 | CH3 | O | —SO2NHCO2(n-C5H11) | CH3,H | |
| 672 | n-Bu | CH3 | CH3 | O | —SO2NHCO2(i-C5H11) | CH3,H | |
| 673 | n-Bu | CH3 | CH3 | O | —SO2NHCO2(cy-C3H5) | CH3,H | |
| 674 | n-Bu | CH3 | CH3 | O | —SO2NHCO2CH2C6H5 | CH3,H | |
| 675 | n-Bu | CH3 | CH3 | O | —SO2NHCO2(n-C4H9) | Cl,H | |
| 676 | n-Bu | CH3 | CH3 | O | —SO2NHCO2(i-C4H9) | Cl,H | |
| 677 | n-Bu | CH3 | CH3 | O | —SO2NHCO2(n-C5H11) | Cl,H | |
| 678 | n-Bu | CH3 | CH3 | O | —SO2NHCO2(i-C5H11) | Cl,H | |
| 679 | n-Bu | CH3 | CH3 | O | —SO2NHCO2(cy-C3H5) | Cl,H | |
| 680 | n-Bu | CH3 | CH3 | O | —SO2NHCO2CH2C6H5 | Cl,H | |
| 681 | n-Bu | CH3 | CH3 | O | —SO2NHCO2(n-C4H9) | F,H | |
| 682 | n-Bu | CH3 | CH3 | O | —SO2NHCO2(i-C4H9) | F,H | |
| 683 | n-Bu | CH3 | CH3 | O | —SO2NHCO2(n-C5H11) | F,H | |
| 684 | n-Bu | CH3 | CH3 | O | —SO2NHCO2(i-C5H11) | F,H | |
| 685 | n-Bu | CH3 | CH3 | O | —SO2NHCO2(cy-C3H5) | F,H | |
| 686 | n-Bu | CH3 | CH3 | O | —SO2NHCO2CH2C6H5 | F,H | |
| 687 | n-Bu | CH3 | CH3 | O | —SO2NHCO2(n-C4H9) | H,n-Pr | |
| 688 | n-Bu | CH3 | CH3 | O | —SO2NHCO2(i-C4H9) | H,n-Pr | |
| 689 | n-Bu | CH3 | CH3 | O | —SO2NHCO2(n-C5H11) | H,n-Pr | |
| 690 | n-Bu | CH3 | CH3 | O | —SO2NHCO2(i-C5H11) | H,n-Pr | |
| 691 | n-Bu | CH3 | CH3 | O | —SO2NHCO2(cy-C3H5) | H,n-Pr | |

TABLE 2-continued

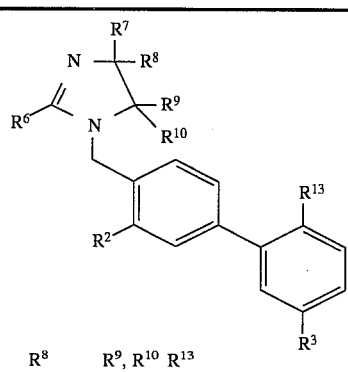

| Ex. | R⁶ | R⁷ | R⁸ | R⁹, R¹⁰ | R¹³ | R², R³ | MS(M + H)⁺ |
|---|---|---|---|---|---|---|---|
| 692 | n-Bu | $CH_3$ | $CH_3$ | O | $-SO_2NHCO_2CH_2C_6H_5$ | H,n-Pr | |
| 693 | n-Bu | $CH_3$ | $CH_3$ | O | $-SO_2NHCO_2(n-C_4H_9)$ | Cl,n-Pr | |
| 694 | n-Bu | $CH_3$ | $CH_3$ | O | $-SO_2NHCO_2(i-C_4H_9)$ | F,n-Pr | |
| 695 | n-Bu | $CH_3$ | $CH_3$ | O | $-SO_2NHCO_2(n-C_5H_{11})$ | Cl,n-Pr | |
| 696 | n-Bu | $CH_3$ | $CH_3$ | O | $-SO_2NHCO_2(i-C_5H_{11})$ | F,n-Pr | |
| 697 | n-Bu | $CH_3$ | $CH_3$ | O | $-SO_2NHCO_2(cy-C_3H_5)$ | F,n-Pr | |
| 698 | n-Bu | $CH_3$ | $CH_3$ | O | $-SO_2NHCO_2CH_2C_6H_5$ | Cl,n-Pr | |
| 699 | p-F-Ph | $CH_3$ | $CH_3$ | O | $-SO_2NHCO_2(n-C_4H_9)$ | H,H | |
| 700 | Ph | $CH_3$ | $CH_3$ | O | $-SO_2NHCO_2(i-C_4H_9)$ | H,H | |
| 701 | iPr | $CH_3$ | $CH_3$ | O | $-SO_2NHCO_2(n-C_5H_{11})$ | H,H | |
| 702 | Ph | $CH_3$ | $CH_3$ | O | $-SO_2NHCO_2(i-C_5H_{11})$ | H,H | |
| 703 | Ph | $CH_3$ | $CH_3$ | O | $-SO_2NHCO_2(cy-C_3H_5)$ | H,H | |
| 704 | Ph | $CH_3$ | $CH_3$ | O | $-SO_2NHCO_2CH_2C_6H_5$ | H,H | |
| 705 | n-Pr | $-(CH_2)_4-$ | | O | $-SO_2NHCO_2(i-C_4H_9)$ | H,H | |
| 706 | n-Pr | $-(CH_2)_4-$ | | O | $-SO_2NHCO_2(n-C_5H_{11})$ | H,H | |
| 707 | n-Pr | $-(CH_2)_4-$ | | O | $-SO_2NHCO_2(i-C_5H_{11})$ | H,H | |
| 708 | n-Pr | $-(CH_2)_4-$ | | O | $-SO_2NHCO_2(cy-C_3H_5)$ | H,H | |
| 709 | n-Pr | $-(CH_2)_4-$ | | O | $-SO_2NHCO_2CH_2C_6H_5$ | H,H | |
| 710 | n-Pr | $-(CH_2)_4-$ | | O | $-SO_2NHCO_2(i-C_4H_9)$ | $CH_3$,H | |
| 711 | n-Pr | $-(CH_2)_4-$ | | O | $-SO_2NHCO_2(n-C_5H_{11})$ | $CH_3$,H | |
| 712 | n-Pr | $-(CH_2)_4-$ | | O | $-SO_2NHCO_2(i-C_5H_{11})$ | $CH_3$,H | |
| 713 | n-Pr | $-(CH_2)_4-$ | | O | $-SO_2NHCO_2(cy-C_3H_5)$ | $CH_3$,H | |
| 714 | n-Pr | $-(CH_2)_4-$ | | O | $-SO_2NHCO_2CH_2C_6H_5$ | $CH_3$,H | |
| 715 | n-Pr | $-(CH_2)_4-$ | | O | $-SO_2NHCO_2(n-C_4H_9)$ | Cl,H | |
| 716 | n-Pr | $-(CH_2)_4-$ | | O | $-SO_2NHCO_2(i-C_4H_9)$ | Cl,H | |
| 717 | n-Pr | $-(CH_2)_4-$ | | O | $-SO_2NHCO_2(n-C_5H_{11})$ | Cl,H | |
| 718 | n-Pr | $-(CH_2)_4-$ | | O | $-SO_2NHCO_2(i-C_5H_{11})$ | Cl,H | |
| 719 | n-Pr | $-(CH_2)_4-$ | | O | $-SO_2NHCO_2(cy-C_3H_5)$ | Cl,H | |
| 720 | n-Pr | $-(CH_2)_4-$ | | O | $-SO_2NHCO_2CH_2C_6H_5$ | Cl,H | |
| 721 | n-Pr | $-(CH_2)_4-$ | | O | $-SO_2NHCO_2(n-C_4H_9)$ | F,H | |
| 722 | n-Pr | $-(CH_2)_4-$ | | O | $-SO_2NHCO_2(i-C_4H_9)$ | F,H | |
| 723 | n-Pr | $-(CH_2)_4-$ | | O | $-SO_2NHCO_2(n-C_5H_{11})$ | F,H | |
| 724 | n-Pr | $-(CH_2)_4-$ | | O | $-SO_2NHCO_2(i-C_5H_{11})$ | F,H | |
| 725 | n-Pr | $-(CH_2)_4-$ | | O | $-SO_2NHCO_2(cy-C_3H_5)$ | F,H | |
| 726 | n-Pr | $-(CH_2)_4-$ | | O | $-SO_2NHCO_2CH_2C_6H_5$ | F,H | |
| 727 | n-Pr | $-(CH_2)_4-$ | | O | $-SO_2NHCO_2(n-C_4H_9)$ | H,n-Pr | |
| 728 | n-Pr | $-(CH_2)_4-$ | | O | $-SO_2NHCO_2(i-C_4H_9)$ | H,n-Pr | |
| 729 | n-Pr | $-(CH_2)_4-$ | | O | $-SO_2NHCO_2(n-C_5H_{11})$ | H,n-Pr | |
| 730 | n-Pr | $-(CH_2)_4-$ | | O | $-SO_2NHCO_2(i-C_5H_{11})$ | H,n-Pr | |
| 731 | n-Pr | $-(CH_2)_4-$ | | O | $-SO_2NHCO_2(cy-C_3H_5)$ | H,n-Pr | |
| 732 | n-Pr | $-(CH_2)_4-$ | | O | $-SO_2NHCO_2CH_2C_6H_5$ | H,n-Pr | |
| 733 | n-Pr | $-(CH_2)_4-$ | | O | $-SO_2NHCO_2(n-C_4H_9)$ | Cl,n-Pr | |
| 734 | n-Pr | $-(CH_2)_4-$ | | O | $-SO_2NHCO_2(i-C_4H_9)$ | F,n-Pr | |
| 735 | n-Pr | $-(CH_2)_4-$ | | O | $-SO_2NHCO_2(n-C_5H_{11})$ | Cl,n-Pr | |
| 736 | n-Pr | $-(CH_2)_4-$ | | O | $-SO_2NHCO_2(i-C_5H_{11})$ | F,n-Pr | |
| 737 | n-Pr | $-(CH_2)_4-$ | | O | $-SO_2NHCO_2(cy-C_3H_5)$ | F,n-Pr | |
| 738 | n-Pr | $-(CH_2)_4-$ | | O | $-SO_2NHCO_2CH_2C_6H_5$ | Cl,n-Pr | |
| 739 | n-Bu | $-(CH_2)_4-$ | | O | $-SO_2NHCO_2(n-C_4H_9)$ | H,H | |
| 740 | n-Bu | $-(CH_2)_4-$ | | O | $-SO_2NHCO_2(i-C_4H_9)$ | H,H | |
| 741 | n-Bu | $-(CH_2)_4-$ | | O | $-SO_2NHCO_2(n-C_5H_{11})$ | H,H | |
| 742 | n-Bu | $-(CH_2)_4-$ | | O | $-SO_2NHCO_2(i-C_5H_{11})$ | H,H | |
| 743 | n-Bu | $-(CH_2)_4-$ | | O | $-SO_2NHCO_2(cy-C_3H_5)$ | H,H | |
| 744 | n-Bu | $-(CH_2)_4-$ | | O | $-SO_2NHCO_2CH_2C_6H_5$ | H,H | |
| 745 | n-Bu | $-(CH_2)_4-$ | | O | $-SO_2NHCO_2(n-C_4H_9)$ | $CH_3$,H | |
| 746 | n-Bu | $-(CH_2)_4-$ | | O | $-SO_2NHCO_2(i-C_4H_9)$ | $CH_3$,H | |
| 747 | n-Bu | $-(CH_2)_4-$ | | O | $-SO_2NHCO_2(n-C_5H_{11})$ | $CH_3$,H | |
| 748 | n-Bu | $-(CH_2)_4-$ | | O | $-SO_2NHCO_2(i-C_5H_{11})$ | $CH_3$,H | |
| 749 | n-Bu | $-(CH_2)_4-$ | | O | $-SO_2NHCO_2(cy-C_3H_5)$ | $CH_3$,H | |
| 750 | n-Bu | $-(CH_2)_4-$ | | O | $-SO_2NHCO_2CH_2C_6H_5$ | $CH_3$,H | |
| 751 | n-Bu | $-(CH_2)_4-$ | | O | $-SO_2NHCO_2(n-C_4H_9)$ | Cl,H | |
| 752 | n-Bu | $-(CH_2)_4-$ | | O | $-SO_2NHCO_2(i-C_4H_9)$ | Cl,H | |
| 753 | n-Bu | $-(CH_2)_4-$ | | O | $-SO_2NHCO_2(n-C_5H_{11})$ | Cl,H | |

TABLE 2-continued

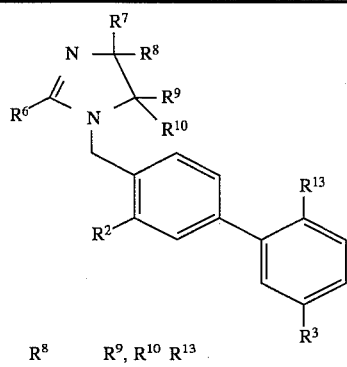

| Ex. | R$^6$ | R$^7$ | R$^8$ | R$^9$, R$^{10}$ | R$^{13}$ | R$^2$, R$^3$ | MS(M + H)$^+$ |
|---|---|---|---|---|---|---|---|
| 754 | n-Bu | —(CH$_2$)$_4$— | | O | —SO$_2$NHCO$_2$(i-C$_5$H$_{11}$) | Cl,H | |
| 755 | n-Bu | —(CH$_2$)$_4$— | | O | —SO$_2$NHCO$_2$(cy-C$_3$H$_5$) | Cl,H | |
| 756 | n-Bu | —(CH$_2$)$_4$— | | O | —SO$_2$NHCO$_2$CH$_2$C$_6$H$_5$ | Cl,H | |
| 757 | n-Bu | —(CH$_2$)$_4$— | | O | —SO$_2$NHCO$_2$(n-C$_4$H$_9$) | F,H | |
| 758 | n-Bu | —(CH$_2$)$_4$— | | O | —SO$_2$NHCO$_2$(i-C$_4$H$_9$) | F,H | |
| 759 | n-Bu | —(CH$_2$)$_4$— | | O | —SO$_2$NHCO$_2$(n-C$_5$H$_{11}$) | F,H | |
| 760 | n-Bu | —(CH$_2$)$_4$— | | O | —SO$_2$NHCO$_2$(i-C$_5$H$_{11}$) | F,H | |
| 761 | n-Bu | —(CH$_2$)$_4$— | | O | —SO$_2$NHCO$_2$(cy-C$_3$H$_5$) | F,H | |
| 762 | n-Bu | —(CH$_2$)$_4$— | | O | —SO$_2$NHCO$_2$CH$_2$C$_6$H$_5$ | F,H | |
| 763 | n-Bu | —(CH$_2$)$_4$— | | O | —SO$_2$NHCO$_2$(n-C$_4$H$_9$) | H,n-Pr | |
| 764 | n-Bu | —(CH$_2$)$_4$— | | O | —SO$_2$NHCO$_2$(i-C$_4$H$_9$) | H,n-Pr | |
| 765 | n-Bu | —(CH$_2$)$_4$— | | O | —SO$_2$NHCO$_2$(n-C$_5$H$_{11}$) | H,n-Pr | |
| 766 | n-Bu | —(CH$_2$)$_4$— | | O | —SO$_2$NHCO$_2$(i-C$_5$H$_{11}$) | H,n-Pr | |
| 767 | n-Bu | —(CH$_2$)$_4$— | | O | —SO$_2$NHCO$_2$(cy-C$_3$H$_5$) | H,n-Pr | |
| 768 | n-Bu | —(CH$_2$)$_4$— | | O | —SO$_2$NHCO$_2$CH$_2$C$_6$H$_5$ | H,n-Pr | |
| 769 | n-Bu | —(CH$_2$)$_4$— | | O | —SO$_2$NHCO$_2$(n-C$_4$H$_9$) | Cl,n-Pr | |
| 770 | n-Bu | —(CH$_2$)$_4$— | | O | —SO$_2$NHCO$_2$(i-C$_4$H$_9$) | F,n-Pr | |
| 771 | n-Bu | —(CH$_2$)$_4$— | | O | —SO$_2$NHCO$_2$(n-C$_5$H$_{11}$) | Cl,n-pr | |
| 772 | n-Bu | —(CH$_2$)$_4$— | | O | —SO$_2$NHCO$_2$(i-C$_5$H$_{11}$) | F,n-Pr | |
| 773 | n-Bu | —(CH$_2$)$_4$— | | O | —SO$_2$NHCO$_2$(cy-C$_3$H$_5$) | F,n-Pr | |
| 774 | n-Bu | —(CH$_2$)$_4$— | | O | —SO$_2$NHCO$_2$CH$_2$C$_6$H$_5$ | Cl,n-Pr | |
| 775 | n-Pr | —(CH$_2$)$_5$— | | O | —SO$_2$NHCO$_2$(n-C$_4$H$_9$) | H,H | |
| 776 | n-Pr | —(CH$_2$)$_5$— | | O | —SO$_2$NHCO$_2$(i-C$_4$H$_9$) | H,H | |
| 777 | n-Pr | —(CH$_2$)$_5$— | | O | —SO$_2$NHCO$_2$(n-C$_5$H$_{11}$) | H,H | |
| 778 | n-Pr | —(CH$_2$)$_5$— | | O | —SO$_2$NHCO$_2$(i-C$_5$H$_{11}$) | H,H | |
| 779 | n-Pr | —(CH$_2$)$_5$— | | O | —SO$_2$NHCO$_2$(cy-C$_3$H$_5$) | H,H | |
| 780 | n-Pr | —(CH$_2$)$_5$— | | O | —SO$_2$NHCO$_2$CH$_2$C$_6$H$_5$ | H,H | |
| 781 | n-Pr | —(CH$_2$)$_5$— | | O | —SO$_2$NHCO$_2$(n-C$_4$H$_9$) | CH$_3$,H | |
| 782 | n-Pr | —(CH$_2$)$_5$— | | O | —SO$_2$NHCO$_2$(i-C$_4$H$_9$) | CH$_3$,H | |
| 783 | n-Pr | —(CH$_2$)$_5$— | | O | —SO$_2$NHCO$_2$(n-C$_5$H$_{11}$) | CH$_3$,H | |
| 784 | n-Pr | —(CH$_2$)$_5$— | | O | —SO$_2$NHCO$_2$(i-C$_5$H$_{11}$) | CH$_3$,H | |
| 785 | n-Pr | —(CH$_2$)$_5$— | | O | —SO$_2$NHCO$_2$(cy-C$_3$H$_5$) | CH$_3$,H | |
| 786 | n-Pr | —(CH$_2$)$_5$— | | O | —SO$_2$NHCO$_2$CH$_2$C$_6$H$_5$ | CH$_3$,H | |
| 787 | n-Pr | —(CH$_2$)$_5$— | | O | —SO$_2$NHCO$_2$(n-C$_4$H$_9$) | Cl,H | |
| 788 | n-Pr | —(CH$_2$)$_5$— | | O | —SO$_2$NHCO$_2$(n-C$_4$H$_9$) | Cl,H | |
| 789 | n-Pr | —(CH$_2$)$_5$— | | O | —SO$_2$NHCO$_2$(n-C$_5$H$_{11}$) | Cl,H | |
| 790 | n-Pr | —(CH$_2$)$_5$— | | O | —SO$_2$NHCO$_2$(i-C$_5$H$_{11}$) | Cl,H | |
| 791 | n-Pr | —(CH$_2$)$_5$— | | O | —SO$_2$NHCO$_2$(cy-C$_3$H$_5$) | Cl,H | |
| 792 | n-Pr | —(CH$_2$)$_5$— | | O | —SO$_2$NHCO$_2$CH$_2$C$_6$H$_5$ | Cl,H | |
| 793 | n-Pr | —(CH$_2$)$_5$— | | O | —SO$_2$NHCO$_2$(n-C$_4$H$_9$) | F,H | |
| 794 | n-Pr | —(CH$_2$)$_5$— | | O | —SO$_2$NHCO$_2$(i-C$_4$H$_9$) | F,H | |
| 795 | n-Pr | —(CH$_2$)$_5$— | | O | —SO$_2$NHCO$_2$(n-C$_5$H$_{11}$) | F,H | |
| 796 | n-Pr | —(CH$_2$)$_5$— | | O | —SO$_2$NHCO$_2$(i-C$_5$H$_{11}$) | F,H | |
| 797 | n-Pr | —(CH$_2$)$_5$— | | O | —SO$_2$NHCO$_2$(cy-C$_3$H$_5$) | F,H | |
| 798 | n-Pr | —(CH$_2$)$_5$— | | O | —SO$_2$NHCO$_2$CH$_2$C$_6$H$_5$ | F,H | |
| 799 | n-Pr | —(CH$_2$)$_5$— | | O | —SO$_2$NHCO$_2$(n-C$_4$H$_9$) | H,n-Pr | |
| 800 | n-Pr | —(CH$_2$)$_5$— | | O | —SO$_2$NHCO$_2$(i-C$_4$H$_9$) | H,n-Pr | |
| 801 | n-Pr | —(CH$_2$)$_5$— | | O | —SO$_2$NHCO$_2$(n-C$_5$H$_{11}$) | H,n-Pr | |
| 802 | n-Pr | —(CH$_2$)$_5$— | | O | —SO$_2$NHCO$_2$(i-C$_5$H$_{11}$) | H,n-Pr | |
| 803 | n-Pr | —(CH$_2$)$_5$— | | O | —SO$_2$NHCO$_2$(cy-C$_3$H$_5$) | H,n-Pr | |
| 804 | n-Pr | —(CH$_2$)$_5$— | | O | —SO$_2$NHCO$_2$CH$_2$C$_6$H$_5$ | H,n-Pr | |
| 805 | n-Pr | —(CH$_2$)$_5$— | | O | —SO$_2$NHCO$_2$(n-C$_4$H$_9$) | Cl,n-Pr | |
| 806 | n-Pr | —(CH$_2$)$_5$— | | O | —SO$_2$NHCO$_2$(i-C$_4$H$_9$) | F,n-Pr | |
| 807 | n-Pr | —(CH$_2$)$_5$— | | O | —SO$_2$NHCO$_2$(n-C$_5$H$_{11}$) | Cl,n-Pr | |
| 808 | n-Pr | —(CH$_2$)$_5$— | | O | —SO$_2$NHCO$_2$(i-C$_5$H$_{11}$) | F,n-Pr | |
| 809 | n-Pr | —(CH$_2$)$_5$— | | O | —SO$_2$NHCO$_2$(cy-C$_3$H$_5$) | F,n-Pr | |
| 810 | n-Pr | —(CH$_2$)$_5$— | | O | —SO$_2$NHCO$_2$CH$_2$C$_6$H$_5$ | Cl,n-Pr | |
| 811 | n-Bu | —(CH$_2$)$_5$— | | O | —SO$_2$NHCO$_2$(n-C$_4$H$_9$) | H,H | |
| 812 | n-Bu | —(CH$_2$)$_5$— | | O | —SO$_2$NHCO$_2$(i-C$_4$H$_9$) | H,H | |
| 813 | n-Bu | —(CH$_2$)$_5$— | | O | —SO$_2$NHCO$_2$(n-C$_5$H$_{11}$) | H,H | |
| 814 | n-Bu | —(CH$_2$)$_5$— | | O | —SO$_2$NHCO$_2$(i-C$_5$H$_{11}$) | H,H | |
| 815 | n-Bu | —(CH$_2$)$_5$— | | O | —SO$_2$NHCO$_2$(cy-C$_3$H$_5$) | H,H | |

TABLE 2-continued

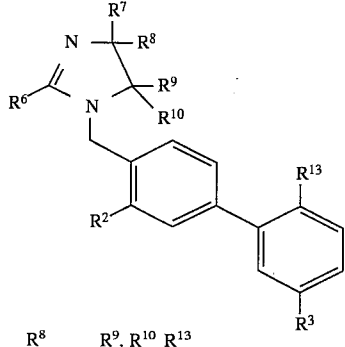

| Ex. | $R^6$ | $R^7$ | $R^8$ | $R^9, R^{10}$ | $R^{13}$ | $R^2, R^3$ | MS(M + H)+ |
|---|---|---|---|---|---|---|---|
| 816 | n-Bu | —(CH$_2$)$_5$— | | O | —SO$_2$NHCO$_2$CH$_2$C$_6$H$_5$ | H,H | |
| 817 | n-Bu | —(CH$_2$)$_5$— | | O | —SO$_2$NHCO$_2$(n-C$_4$H$_9$) | CH$_3$,H | |
| 818 | n-Bu | —(CH$_2$)$_5$— | | O | —SO$_2$NHCO$_2$(i-C$_4$H$_9$) | CH$_3$,H | |
| 819 | n-Bu | —(CH$_2$)$_5$— | | O | —SO$_2$NHCO$_2$(n-C$_5$H$_{11}$) | CH$_3$,H | |
| 820 | n-Bu | —(CH$_2$)$_5$— | | O | —SO$_2$NHCO$_2$(i-C$_5$H$_{11}$) | CH$_3$,H | |
| 821 | n-Bu | —(CH$_2$)$_5$— | | O | —SO$_2$NHCO$_2$(cy-C$_3$H$_5$) | CH$_3$,H | |
| 822 | n-Bu | —(CH$_2$)$_5$— | | O | —SO$_2$NHCO$_2$CH$_2$C$_6$H$_5$ | CH$_3$,H | |
| 823 | n-Bu | —(CH$_2$)$_5$— | | O | —SO$_2$NHCO$_2$(n-C$_4$H$_9$) | Cl,H | |
| 824 | n-Bu | —(CH$_2$)$_5$— | | O | —SO$_2$NHCO$_2$(i-C$_4$H$_9$) | Cl,H | |
| 825 | n-Bu | —(CH$_2$)$_5$— | | O | —SO$_2$NHCO$_2$(n-C$_5$H$_{11}$) | Cl,H | |
| 826 | n-Bu | —(CH$_2$)$_5$— | | O | —SO$_2$NHCO$_2$(i-C$_5$H$_{11}$) | Cl,H | |
| 827 | n-Bu | —(CH$_2$)$_5$— | | O | —SO$_2$NHCO$_2$(cy-C$_3$H$_5$) | Cl,H | |
| 828 | n-Bu | —(CH$_2$)$_5$— | | O | —SO$_2$NHCO$_2$CH$_2$C$_6$H$_5$ | Cl,H | |
| 829 | n-Bu | —(CH$_2$)$_5$— | | O | —SO$_2$NHCO$_2$C$_6$H$_5$ | F,H | |
| 830 | n-Bu | —(CH$_2$)$_5$— | | O | —SO$_2$NHCO$_2$(n-C$_4$H$_9$) | F,H | |
| 831 | n-Bu | —(CH$_2$)$_5$— | | O | —SO$_2$NHCO$_2$(i-C$_4$H$_9$) | F,H | |
| 832 | n-Bu | —(CH$_2$)$_5$— | | O | —SO$_2$NHCO$_2$(n-C$_5$H$_{11}$) | F,H | |
| 833 | n-Bu | —(CH$_2$)$_5$— | | O | —SO$_2$NHCO$_2$(i-C$_5$H$_{11}$) | F,H | |
| 834 | n-Bu | —(CH$_2$)$_5$— | | O | —SO$_2$NHCO$_2$(cy-C$_3$H$_5$) | F,H | |
| 835 | n-Bu | —(CH$_2$)$_5$— | | O | —SO$_2$NHCO$_2$CH$_2$C$_6$H$_5$ | F,H | |
| 836 | n-Bu | —(CH$_2$)$_5$— | | O | —SO$_2$NHCO$_2$(n-C$_4$H$_9$) | H,n-Pr | |
| 837 | n-Bu | —(CH$_2$)$_5$— | | O | —SO$_2$NHCO$_2$(i-C$_4$H$_9$) | H,n-Pr | |
| 838 | n-Bu | —(CH$_2$)$_5$— | | O | —SO$_2$NHCO$_2$(n-C$_5$H$_{11}$) | H,n-Pr | |
| 839 | n-Bu | —(CH$_2$)$_5$— | | O | —SO$_2$NHCO$_2$(i-C$_5$H$_{11}$) | H,n-Pr | |
| 840 | n-Bu | —(CH$_2$)$_5$— | | O | —SO$_2$NHCO$_2$(cy-C$_3$H$_5$) | H,n-Pr | |
| 841 | n-Bu | —(CH$_2$)$_5$— | | O | —SO$_2$NHCO$_2$CH$_2$C$_6$H$_5$ | H,n-Pr | |
| 842 | n-Bu | —(CH$_2$)$_5$— | | O | —SO$_2$NHCO$_2$(n-C$_4$H$_9$) | Cl,n-Pr | |
| 843 | n-Bu | —(CH$_2$)$_5$— | | O | —SO$_2$NHCO$_2$(i-C$_4$H$_9$) | F,n-Pr | |
| 844 | n-Bu | —(CH$_2$)$_5$— | | O | —SO$_2$NHCO$_2$(n-C$_5$H$_{11}$) | Cl,n-Pr | |
| 845 | n-Bu | —(CH$_2$)$_5$— | | O | —SO$_2$NHCO$_2$(i-C$_5$H$_{11}$) | F,n-Pr | |
| 846 | n-Bu | —(CH$_2$)$_5$— | | O | —SO$_2$NHCO$_2$(cy-C$_3$H$_5$) | F,n-Pr | |
| 847 | n-Bu | —(CH$_2$)$_5$— | | O | —SO$_2$NHCO$_2$CH$_2$C$_6$H$_5$ | Cl,n-Pr | |
| 848 | n-Pr | —(CH$_2$)S(CH$_2$)$_2$— | | O | —SO$_2$NHCO$_2$CH$_2$C$_6$H$_5$ | H,H | |
| 849 | n-Pr | —(CH$_2$)S(CH$_2$)$_2$— | | O | —SO$_2$NHCO$_2$(n-C$_4$H$_9$) | H,H | |
| 850 | n-Pr | —(CH$_2$)S(CH$_2$)$_2$— | | O | —SO$_2$NHCO$_2$(i-C$_4$H$_9$) | H,H | |
| 851 | n-Pr | —(CH$_2$)S(CH$_2$)$_2$— | | O | —SO$_2$NHCO$_2$(n-C$_5$H$_{11}$) | H,H | |
| 852 | n-Pr | —(CH$_2$)S(CH$_2$)$_2$— | | O | —SO$_2$NHCO$_2$(i-C$_5$H$_{11}$) | H,H | |
| 853 | n-Pr | —(CH$_2$)S(CH$_2$)$_2$— | | O | —SO$_2$NHCO$_2$(cy-C$_3$H$_5$) | H,H | |
| 854 | n-Pr | —(CH$_2$)S(CH$_2$)$_2$— | | O | —SO$_2$NHCO$_2$CH$_2$C$_6$H$_5$ | H,H | |
| 855 | n-Pr | —(CH$_2$)S(CH$_2$)$_2$— | | O | —SO$_2$NHCO$_2$(n-C$_4$H$_9$) | CH$_3$,H | |
| 856 | n-Pr | —(CH$_2$)S(CH$_2$)$_2$— | | O | —SO$_2$NHCO$_2$(i-C$_4$H$_9$) | CH$_3$,H | |
| 857 | n-Pr | —(CH$_2$)S(CH$_2$)$_2$— | | O | —SO$_2$NHCO$_2$(n-C$_5$H$_{11}$) | CH$_3$,H | |
| 858 | n-Pr | —(CH$_2$)S(CH$_2$)$_2$— | | O | —SO$_2$NHCO$_2$(i-C$_5$H$_{11}$) | CH$_3$,H | |
| 859 | n-Pr | —(CH$_2$)S(CH$_2$)$_2$— | | O | —SO$_2$NHCO$_2$(cy-C$_3$H$_5$) | CH$_3$,H | |
| 860 | n-Pr | —(CH$_2$)S(CH$_2$)$_2$— | | O | —SO$_2$NHCO$_2$CH$_2$C$_6$H$_5$ | CH$_3$,H | |
| 861 | n-Pr | —(CH$_2$)S(CH$_2$)$_2$— | | O | —SO$_2$NHCO$_2$(n-C$_4$H$_9$) | Cl,H | |
| 862 | n-Pr | —(CH$_2$)S(CH$_2$)$_2$— | | O | —SO$_2$NHCO$_2$(n-C$_4$H$_9$) | Cl,H | |
| 863 | n-Pr | —(CH$_2$)S(CH$_2$)$_2$— | | O | —SO$_2$NHCO$_2$(n-C$_5$H$_{11}$) | Cl,H | |
| 864 | n-Pr | —(CH$_2$)S(CH$_2$)$_2$— | | O | —SO$_2$NHCO$_2$(i-C$_5$H$_{11}$) | Cl,H | |
| 865 | n-Pr | —(CH$_2$)S(CH$_2$)$_2$— | | O | —SO$_2$NHCO$_2$(cy-C$_3$H$_5$) | Cl,H | |
| 866 | n-Pr | —(CH$_2$)S(CH$_2$)$_2$— | | O | —SO$_2$NHCO$_2$CH$_2$C$_6$H$_5$ | Cl,H | |
| 867 | n-Pr | —(CH$_2$)S(CH$_2$)$_2$— | | O | —SO$_2$NHCO$_2$(n-C$_4$H$_9$) | F,H | |
| 868 | n-Pr | —(CH$_2$)S(CH$_2$)$_2$— | | O | —SO$_2$NHCO$_2$NH(n-C$_4$H$_9$) | F,H | |
| 869 | n-Pr | —(CH$_2$)S(CH$_2$)$_2$— | | O | —SO$_2$NHCO$_2$(i-C$_4$H$_9$) | F,H | |
| 870 | n-Pr | —(CH$_2$)S(CH$_2$)$_2$— | | O | —SO$_2$NHCO$_2$(n-C$_5$H$_{11}$) | F,H | |
| 871 | n-Pr | —(CH$_2$)S(CH$_2$)$_2$— | | O | —SO$_2$NHCO$_2$(i-C$_5$H$_{11}$) | F,H | |
| 872 | n-Pr | —(CH$_2$)S(CH$_2$)$_2$— | | O | —SO$_2$NHCO$_2$(cy-C$_3$H$_5$) | F,H | |
| 873 | n-Pr | —(CH$_2$)S(CH$_2$)$_2$— | | O | —SO$_2$NHCO$_2$CH$_2$C$_6$H$_5$ | F,H | |
| 874 | n-Pr | —(CH$_2$)S(CH$_2$)$_2$— | | O | —SO$_2$NHCO$_2$(n-C$_4$H$_9$) | H,n-Pr | |
| 875 | n-Pr | —(CH$_2$)S(CH$_2$)$_2$— | | O | —SO$_2$NHCO$_2$NH(n-C$_4$H$_9$) | H,n-Pr | |
| 876 | n-Pr | —(CH$_2$)S(CH$_2$)$_2$— | | O | —SO$_2$NHCO$_2$(i-C$_4$H$_9$) | H,n-Pr | |
| 877 | n-Pr | —(CH$_2$)S(CH$_2$)$_2$— | | O | —SO$_2$NHCO$_2$(n-C$_5$H$_{11}$) | H,n-Pr | |

TABLE 2-continued

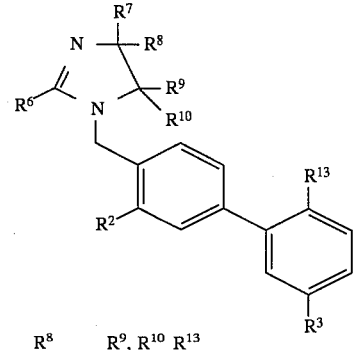

| Ex. | R⁶ | R⁷ R⁸ | R⁹, R¹⁰ | R¹³ | R², R³ | MS(M + H)⁺ |
|---|---|---|---|---|---|---|
| 878 | n-Pr | —(CH₂)S(CH₂)₂— | O | —SO₂NHCO₂(i-C₅H₁₁) | H,n-Pr | |
| 879 | n-Pr | —(CH₂)S(CH₂)₂— | O | —SO₂NHCO₂(cy-C₃H₅) | H,n-Pr | |
| 880 | n-Pr | —(CH₂)S(CH₂)₂— | O | —SO₂NHCO₂CH₂C₆H₅ | H,n-Pr | |
| 881 | n-Pr | —(CH₂)S(CH₂)₂— | O | —SO₂NHCO₂(n-C₄H₉) | Cl,n-Pr | |
| 882 | n-Pr | —(CH₂)S(CH₂)₂— | O | —SO₂NHCO₂(i-C₄H₉) | F,n-Pr | |
| 883 | n-Pr | —(CH₂)S(CH₂)₂— | O | —SO₂NHCO₂(n-C₅H₁₁) | Cl,n-Pr | |
| 884 | n-Pr | —(CH₂)S(CH₂)₂— | O | —SO₂NHCO₂(i-C₅H₁₁) | F,n-Pr | |
| 885 | n-Pr | —(CH₂)S(CH₂)₂— | O | —SO₂NHCO₂(cy-C₃H₅) | F,n-Pr | |
| 886 | n-Pr | —(CH₂)S(CH₂)₂— | O | —SO₂NHCO₂CH₂C₆H₅ | Cl,n-Pr | |
| 887 | n-Bu | —(CH₂)S(CH₂)₂— | O | —SO₂NHCO₂(n-C₄H₉) | H,H | |
| 888 | n-Bu | —(CH₂)S(CH₂)₂— | O | —SO₂NHCO₂(i-C₄H₉) | H,H | |
| 889 | n-Bu | —(CH₂)S(CH₂)₂— | O | —SO₂NHCO₂(n-C₄H₉) | H,H | |
| 890 | n-Bu | —(CH₂)S(CH₂)₂— | O | —SO₂NHCO₂(i-C₅H₁₁) | H,H | |
| 891 | n-Bu | —(CH₂)S(CH₂)₂— | O | —SO₂NHCO₂(cy-C₃H₅) | H,H | |
| 892 | n-Bu | —(CH₂)S(CH₂)₂— | O | —SO₂NHCO₂CH₂C₆H₅ | H,H | |
| 893 | n-Bu | —(CH₂)S(CH₂)₂— | O | —SO₂NHCO₂(n-C₄H₉) | CH₃,H | |
| 894 | n-Bu | —(CH₂)S(CH₂)₂— | O | —SO₂NHCO₂(i-C₄H₉) | CH₃,H | |
| 895 | n-Bu | —(CH₂)S(CH₂)₂— | O | —SO₂NHCO₂(n-C₅H₁₁) | CH₃,H | |
| 896 | n-Bu | —(CH₂)S(CH₂)₂— | O | —SO₂NHCO₂(i-C₅H₁₁) | CH₃,H | |
| 897 | n-Bu | —(CH₂)S(CH₂)₂— | O | —SO₂NHCO₂(cy-C₃H₅) | CH₃,H | |
| 898 | n-Bu | —(CH₂)S(CH₂)₂— | O | —SO₂NHCO₂CH₂C₆H₅ | CH₃,H | |
| 899 | n-Bu | —(CH₂)S(CH₂)₂— | O | —SO₂NHCO₂(n-C₄H₉) | Cl,H | |
| 900 | n-Bu | —(CH₂)S(CH₂)₂— | O | —SO₂NHCO₂(i-C₄H₉) | Cl,H | |
| 901 | n-Bu | —(CH₂)S(CH₂)₂— | O | —SO₂NHCO₂(n-C₅H₁₁) | Cl,H | |
| 902 | n-Bu | —(CH₂)S(CH₂)₂— | O | —SO₂NHCO₂(i-C₅H₁₁) | Cl,H | |
| 903 | n-Bu | —(CH₂)S(CH₂)₂— | O | —SO₂NHCO₂(cy-C₃H₅) | Cl,H | |
| 904 | n-Bu | —(CH₂)S(CH₂)₂— | O | —SO₂NHCO₂CH₂C₆H₅ | Cl,H | |
| 905 | n-Bu | —(CH₂)S(CH₂)₂— | O | —SO₂NHCO₂(n-C₄H₉) | F,H | |
| 906 | n-Bu | —(CH₂)S(CH₂)₂— | O | —SO₂NHCO₂(i-C₄H₉) | F,H | |
| 907 | n-Bu | —(CH₂)S(CH₂)₂— | O | —SO₂NHCO₂(n-C₅H₁₁) | F,H | |
| 908 | n-Bu | —(CH₂)S(CH₂)₂— | O | —SO₂NHCO₂(i-C₅H₁₁) | F,H | |
| 909 | n-Bu | —(CH₂)S(CH₂)₂— | O | —SO₂NHCO₂(cy-C₃H₅) | F,H | |
| 910 | n-Bu | —(CH₂)S(CH₂)₂— | O | —SO₂NHCO₂CH₂C₆H₅ | F,H | |
| 911 | n-Bu | —(CH₂)S(CH₂)₂— | O | —SO₂NHCO₂(n-C₄H₉) | H,n-Pr | |
| 912 | n-Bu | —(CH₂)S(CH₂)₂— | O | —SO₂NHCO₂(i-C₄H₉) | H,n-Pr | |
| 913 | n-Bu | —(CH₂)S(CH₂)₂— | O | —SO₂NHCO₂(n-C₅H₁₁) | H,n-Pr | |
| 914 | n-Bu | —(CH₂)S(CH₂)₂— | O | —SO₂NHCO₂(i-C₅H₁₁) | H,n-Pr | |
| 915 | n-Bu | —(CH₂)S(CH₂)₂— | O | —SO₂NHCO₂(cy-C₃H₅) | H,n-Pr | |
| 916 | n-Bu | —(CH₂)S(CH₂)₂— | O | —SO₂NHCO₂CH₂C₆H₅ | H,n-Pr | |
| 917 | n-Bu | —(CH₂)S(CH₂)₂— | O | —SO₂NHCO₂(n-C₄H₉) | Cl,n-Pr | |
| 918 | n-Bu | —(CH₂)S(CH₂)₂— | O | —SO₂NHCO₂(i-C₄H₉) | F,n-Pr | |
| 919 | n-Bu | —(CH₂)S(CH₂)₂— | O | —SO₂NHCO₂(n-C₅H₁₁) | F,n-Pr | |
| 920 | n-Bu | —(CH₂)S(CH₂)₂— | O | —SO₂NHCO₂(i-C₅H₁₁) | F,n-Pr | |
| 921 | n-Bu | —(CH₂)S(CH₂)₂— | O | —SO₂NHCO₂(cy-C₃H₅) | F,n-Pr | |
| 922 | n-Bu | —(CH₂)S(CH₂)₂— | O | —SO₂NHCO₂CH₂C₆H₅ | Cl,n-Pr | |
| 923 | n-Pr | —(CH₂)O(CH₂)₂— | O | —SO₂NHCO₂(n-C₄H₉) | H,H | |
| 924 | n-Pr | —(CH₂)O(CH₂)₂— | O | —SO₂NHCO₂(i-C₄H₉) | H,H | |
| 925 | n-Pr | —(CH₂)O(CH₂)₂— | O | —SO₂NHCO₂(n-C₅H₁₁) | H,H | |
| 926 | n-Pr | —(CH₂)O(CH₂)₂— | O | —SO₂NHCO₂(i-C₅H₁₁) | H,H | |
| 927 | n-Pr | —(CH₂)O(CH₂)₂— | O | —SO₂NHCO₂(cy-C₃H₅) | H,H | |
| 928 | n-Pr | —(CH₂)O(CH₂)₂— | O | —SO₂NHCO₂CH₂C₆H₅ | H,H | |
| 929 | n-Pr | —(CH₂)O(CH₂)₂— | O | —SO₂NHCO₂(n-C₄H₉) | F,H | |
| 930 | n-Pr | —(CH₂)O(CH₂)₂— | O | —SO₂NHCO₂(i-C₄H₉) | F,H | |
| 931 | n-Pr | —(CH₂)O(CH₂)₂— | O | —SO₂NHCO₂(n-C₅H₁₁) | F,H | |
| 932 | n-Pr | —(CH₂)O(CH₂)₂— | O | —SO₂NHCO₂(i-C₅H₁₁) | F,H | |
| 933 | n-Pr | —(CH₂)O(CH₂)₂— | O | —SO₂NHCO₂(cy-C₃H₅) | F,H | |
| 934 | n-Pr | —(CH₂)O(CH₂)₂— | O | —SO₂NHCO₂CH₂C₆H₅ | F,H | |
| 935 | n-Pr | —(CH₂)O(CH₂)₂— | O | —SO₂NHCO₂(n-C₄H₉) | Cl,H | |
| 936 | n-Pr | —(CH₂)O(CH₂)₂— | O | —SO₂NHCO₂(i-C₄H₉) | Cl,H | |
| 937 | n-Pr | —(CH₂)O(CH₂)₂— | O | —SO₂NHCO₂(n-C₅H₁₁) | Cl,H | |
| 938 | n-Pr | —(CH₂)O(CH₂)₂— | O | —SO₂NHCO₂(i-C₅H₁₁) | Cl,H | |
| 939 | n-Pr | —(CH₂)O(CH₂)₂— | O | —SO₂NHCO₂(cy-C₃H₅) | Cl,H | |

TABLE 2-continued

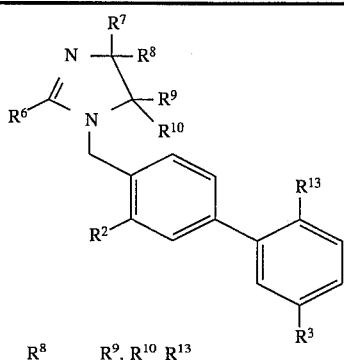

| Ex. | R⁶ | R⁷ | R⁸ | R⁹, R¹⁰ | R¹³ | R², R³ | MS(M + H)⁺ |
|---|---|---|---|---|---|---|---|
| 940 | n-Pr | —(CH₂)O(CH₂)₂— | | O | —SO₂NHCO₂CH₂C₆H₅ | Cl,H | |
| 941 | n-Pr | —(CH₂)SO₂(CH₂)₂— | | O | —SO₂NHCO₂(n-C₄H₉) | H,H | |
| 942 | n-Pr | —(CH₂)SO₂(CH₂)₂— | | O | —SO₂NHCO₂(i-C₄H₉) | H,H | |
| 943 | n-Pr | —(CH₂)SO₂(CH₂)₂— | | O | —SO₂NHCO₂(n-C₅H₁₁) | H,H | |
| 944 | n-Pr | —(CH₂)SO₂(CH₂)₂— | | O | —SO₂NHCO₂(i-C₅H₁₁) | H,H | |
| 945 | n-Pr | —(CH₂)SO₂(CH₂)₂— | | O | —SO₂NHCO₂(cy-C₃H₅) | H,H | |
| 946 | n-Pr | —(CH₂)SO₂(CH₂)₂— | | O | —SO₂NHCO₂CH₂C₆H₅ | H,H | |
| 947 | n-Pr | —(CH₂)NCOMe(CH₂)₂— | | O | —SO₂NHCO₂(n-C₄H₉) | H,H | |
| 948 | n-Pr | —(CH₂)NCOMe(CH₂)₂— | | O | —SO₂NHCO₂(i-C₄H₉) | H,H | |
| 949 | n-Pr | —(CH₂)NCOMe(CH₂)₂— | | O | —SO₂NHCO₂(n-C₅H₁₁) | H,H | |
| 950 | n-Pr | —(CH₂)NCOMe(CH₂)₂— | | O | —SO₂NHCO₂(i-C₅H₁₁) | H,H | |
| 951 | n-Pr | —(CH₂)NCOMe(CH₂)₂— | | O | —SO₂NHCO₂(cy-C₃H₅) | H,H | |
| 952 | n-Pr | —(CH₂)NCOMe(CH₂)₂— | | O | —SO₂NHCO₂CH₂C₆H₅ | H,H | |
| 953 | n-Pr | —(CH₂)NCOPh(CH₂)₂— | | O | —SO₂NHCO₂(n-C₄H₉) | H,H | |
| 954 | n-Pr | —(CH₂)NCOPh(CH₂)₂— | | O | —SO₂NHCO₂(i-C₄H₉) | H,H | |
| 955 | n-Pr | —(CH₂)NCOPh(CH₂)₂— | | O | —SO₂NHCO₂CH₂C₆H₅ | H,H | |
| 956 | n-Pr | —(CH₂)NCOPh(CH₂)₂— | | O | —SO₂NHCO₂(i-C₅H₁₁) | H,H | |
| 957 | n-Pr | —(CH₂)NCOPh(CH₂)₂— | | O | —SO₂NHCO₂(cy-C₃H₅) | H,H | |
| 958 | n-Pr | —(CH₂)NCOPh(CH₂)₂— | | O | —SO₂NHCO₂CH₂C₆H₅ | H,H | |
| 959 | n-Pr | —(CH₂)NCH₂Ph(CH₂)₂— | | O | —SO₂NHCO₂(n-C₄H₉) | F,H | |
| 960 | n-Pr | —(CH₂)NCH₂Ph(CH₂)₂— | | O | —SO₂NHCO₂(i-C₄H₉) | F,H | |
| 961 | n-Pr | —(CH₂)NCH₂Ph(CH₂)₂— | | O | —SO₂NHCO₂(n-C₅H₁₁) | F,H | |
| 962 | n-Pr | —(CH₂)NCH₂Ph(CH₂)₂— | | O | —SO₂NHCO₂(i-C₅H₁₁) | F,H | |
| 963 | n-Pr | —(CH₂)NCH₂Ph(CH₂)₂— | | O | —SO₂NHCO₂(cy-C₃H₅) | F,H | |
| 964 | n-Pr | —(CH₂)NCH₂Ph(CH₂)₂— | | O | —SO₂NHCO₂CH₂C₆H₅ | F,H | |
| 965 | n-Pr | CF₃ | CF₃ | O | —SO₂NHCO₂(n-C₄H₉) | H,H | |
| 966 | n-Pr | CF₃ | CF₃ | O | —SO₂NHCO₂(i-C₄H₉) | H,H | |
| 967 | n-Pr | CF₃ | CF₃ | O | —SO₂NHCO₂(n-C₅H₁₁) | H,H | |
| 968 | n-Pr | CF₃ | CF₃ | O | —SO₂NHCO₂(i-C₅H₁₁) | H,H | |
| 969 | n-Pr | CF₃ | CF₃ | O | —SO₂NHCO₂(cy-C₃H₅) | H,H | |
| 970 | n-Pr | CF₃ | CF₃ | O | —SO₂NHCO₂CH₂C₆H₅ | H,H | |
| 971 | n-Pr | Ph | Ph | O | —SO₂NHCO₂(n-C₄H₉) | H,H | |
| 972 | n-Pr | Ph | Ph | O | —SO₂NHCO₂(i-C₄H₉) | H,H | |
| 973 | n-Pr | Ph | Pb | O | —SO₂NHCO₂(n-C₅H₁₁) | H,H | |
| 974 | n-Pr | Ph | Ph | O | —SO₂NHCO₂(i-C₅H₁₁) | H,H | |
| 975 | n-Pr | Ph | Ph | O | —SO₂NHCO₂(cy-C₃H₅) | H,H | |
| 976 | n-Pr | Ph | Ph | O | —SO₂NHCO₂CH₂C₆H₅ | H,H | |
| 977 | n-Pr | —(CH₂)₂— | | O | —SO₂NHCO₂(n-C₄H₉) | H,H | |
| 978 | n-Pr | —(CH₂)₂— | | O | —SO₂NHCO₂(i-C₄H₉) | H,H | |
| 979 | n-Pr | —(CH₂)₂— | | O | —SO₂NHCO₂(n-C₅H₁₁) | H,H | |
| 980 | n-Pr | —(CH₂)₂— | | O | —SO₂NHCO₂(i-C₅H₁₁) | H,H | |
| 981 | n-Pr | —(CH₂)₂— | | O | —SO₂NHCO₂(cy-C₃H₅) | H,H | |
| 982 | n-Pr | —(CH₂)₂— | | O | —SO₂NHCO₂CH₂C₆H₅ | H,H | |

Utility

Angiotensin II (AII) produces numerous biological responses (e.g., vasoconstriction) through stimulation of its receptors on cell membranes. For the purpose of identifying compounds such as AII antagonists which are capable of interacting with the AII receptor, a ligand-receptor binding assay was utilized for the initial screen. The assay was carried out according to the method described by Chiu et al., Receptor, 1, 33 (1990). In brief, aliquots of a fleshly prepared particulate fraction of rat adrenal cortex were incubated with 0.05 nM [$^{125}$I]AII and varying concentrations of potential AII antagonists in a Tris buffer. After a 1 h incubation the reaction was terminated by addition of cold assay buffer. The bound and free radioactivity were rapidly separated through glass-fiber filters, and the trapped radioactivity was quantitated by scintillation counting. The inhibitory concentration ($Ic_{50}$) of potential AII antagonists which gives 50% displacement of the total specifically bound [125I]AII is presented as a measure of the affinity of such compound for the AII receptor.

Using the assay method described above, the compounds of this invention are found to exhibit an activity of at least $Ic_{50} < 10$ micromolar, thereby demonstrating and confirming the activity of these compounds as effective AII antagonists.

The potential antihypertensive effects of the compounds of this invention may be demonstrated by administering the compounds to awake rats made hypertensive by ligation of the left renal artery [Cangiano et at., J. Pharmacol. Exp.

Ther., 208, 310 (1979)]. This procedure increases blood pressure by increasing renin production with consequent elevation of AII levels. Compounds are administered intravenously via a cannula in the jugular vein at 10 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds.

Using the in vivo methodology described above, the compounds of this invention are found to exhibit an activity (intravenous) which is 10 mg/kg or less, and/or an activity (oral) which is 100 mg/kg or less, thereby demonstrating and confirming the utility of these compounds as effective agents in lowering blood pressure.

The compounds of the invention are useful in treating hypertension. They are also of value in the management of acute and chronic congestive heart failure and angina. These compounds may also be expected to be useful in the treatment of primary and secondary hyperaldosteronism; renal diseases such as diabetic nephropathy, glomemlonephritis, glomerular sclerosis, nephrotic syndrome, hypertensive nephrosclerosis, end stage renal disease, used in renal transplant therapy, and to treat renovascular hypertension, scleroderma, left ventricular dysfunction, systolic and diastolic dysfunction, diabetic retinopathy and in the management of vascular disorders such as migraine, Raynaud's disease, and as prophylaxis to minimize the atherosclerotic process and neointimal hyperplasia following angioplasty or vascular injury and to retard the onset of type II diabetes. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, insets, gels and the like. Pharmaceutical formulations prepared to treat intraocular pressure would typically contain about 0.1% to 15% by weight, preferably 0.5% to 2% by weight, of a compound of this invention. For this use, the compounds of this invention may also be used in combination with other medications for the treatment of glaucoma including choline esterase inhibitors such as physostigmine salicylate or demecarium bromide, parasympathominetic agents such as pilocarpine nitrate, β-adrenergic antagonists such as timolol maleate, adrenergic agonists such as epinephrine and carbonic anhydrase inhibitors such as MK-507.

In the management of hypertension and the clinical conditions noted above, the compounds of this invention may be utilized with a pharmaceutical carder in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diet that is being followed by a patient, concurrent medication, and other factors which those skilled in the art will recognize, the dosage range will generally be about 1 to 1000 mg per patient per day which can be administered in single or multiple doses. Preferably, the dosage range will be about 5 to 500 mg per patient per day; more preferably about 5 to 300 mg per patient per day.

The compounds of this invention can also be administered in combination with other antihypertensives and/or diuretics. For example, the compounds of this invention can be given in combination with diuretics such as hydrochlorothiazide, chlorothiazide, chlorthalidone, methylclothiazide, furosemide, ethacrynic acid, triamterene, amiloride spironolactone and atriopeptin; calcium channel blockers, such as diltiazem, felodipine, nifedipine, amlodipine, nimodipine, isradipine, nitrendipine and verapamil; β adrenergic antagonists such as timolol, atenolol, metoprolol, propanolol, nadolol and pindolol; angiotensin converting enzyme inhibitors such as enalapril, lisinopril, captopril, ramipril, quinapril and zofenopril; renin inhibitors such as A-69729, FK 906 and FK 744; α-adrenergic antagonists such as prazosin, doxazosin, and terazosin; sympatholytic agents such as methyldopa, clonidine and guanabenz; atriopeptidase inhibitors (alone or with ANP) such as UK-79300; serotonin antagonists such as ketanserin; $A_2$-adrenosine receptor agonists such as CGS 22492C; potassium channel agonists such as pinacidil and cromakalim; and various other antihypertensive drugs including reserpine, minoxidil, guanethidine, hydralazinc hydrochloride and sodium nitroprusside as well as combinations of the above-named drugs. Combinations useful in the management of congestive heart failure include, in addition, compounds of this invention with cardiac stimulants such as dobutamine and xamoterol and phosphodiesterase inhibitors including amirinone and milrinone.

Typically, the individual daily dosages for these combinations can range from about one-fifth of the minimally recommended clinical dosages to the maximum recommended levels for the entities when they are given singly. To illustrate these combinations, one of the angiotensin II antagonists of this invention effective clinically in the 5–500 milligrams per day range can be effectively combined at levels at the 1.0–500 milligrams per day range with the following compounds at the indicated per day dose range; hydrochlorothiazide (6–100 mg), chlorothiazide (125–500 rag), ethacrynic acid (5–200 mg), amiloride (5–20 mg), furosemide (5–80 mg), propranolol (10–480 mg), timolol maleate (1–20 mg), methyldopa (125–2000 mg), felodipine (1–20 mg), nifedipine (5–120 mg), nitrendipine (5–60 mg), and diltiazem (30–540 mg). In addition, triple drag combinations of hydrochlorothiazide (5–100 mg) plus amiloride (5–20 mg) plus angiotensin II antagonists of this invention (1–500 mg) or hydrochlorothiazide (5–100 mg) plus timolol maleate (5–60 mg) plus an angiotensin II antagonists of this invention (1–500 mg) or hydrochlorothiazide (5–200 mg) and nifedipine (5–60 mg) plus an angiotensin II antagonist of this invention (1–500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

The active ingredient can be administered orally in solid dosage forms, such as capsules, tablets, and powders, or in liquid dosage forms, such as elixirs syrups, and suspensions. It can also be administered parenterally, in sterile liquid dosage forms. Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences,* A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed off or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parentered composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when stepwise in conjunction with another therapeutic agent. When the drugs are administered in physical combination, the dosage form and administration route should be selected for compatibility with both drugs.

What is claimed is:

1. A compound of formula (I)

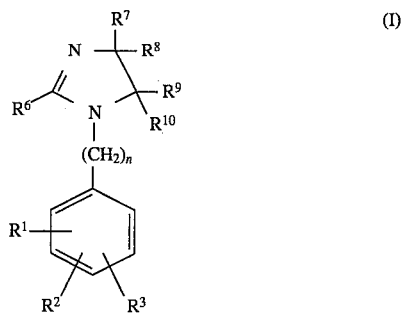

wherein:

$R^1$ is other than in the ortho position and is:

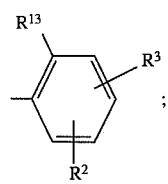

$R^2$ is (a) H, (b) halo (F, Cl, Br, I), (c) $C_1$–$C_4$ alkyl, (d) $C_1$–$C_4$ alkoxy, (e) $C_1$–$C_4$ acyloxy, (f) $C_1$–$C_4$ alkylthio, (g) $C_1$–$C_4$ alkylsulfinyl, (h) $C_1$–$C_4$ alkylsulfonyl, (i) hydroxy ($C_1$–$C_4$) alkyl, (j) phenyl ($C_1$–$C_4$) alkyl, (k) —$CO_2H$, (l) —CN, (m) —$CONHOR^{12}$, (n) —$SO_2NHR^{21}$, (o) —$NH_2$, (p) $C_1$–$C_4$ alkylamino, (q) $C_1$–$C_4$ dialkylamino, (r) —$NHSO_2R^{20}$, (s) —$NO_2$, (t) furyl, (u) aryl; wherein aryl is phenyl optionally substituted with one or two substituents selected from the group consisting of halo, $C_1$–$C_4$ alkyl, $C_1$–$C_4$ alkoxy, —$NO_2$, $CF_3$, $C_1$–$C_4$ alkylthio, —OH, —$NH_2$, $C_1$–$C_4$ alkylamino, $C_1$–$C_4$ dialkylamino, —CN, —$CO_2H$, —$CO_2CH_3$, —$CO_2CH_2CH_3$, —$CO_2$-benzyl;

$R^3$ is (a) H, (b) halo, (c) $C_1$–$C_4$ alkyl, (d) $C_1$–$C_4$ alkoxy, (e) $C_1$–$C_4$ alkoxyalkyl;

$R^4$ is (a) —CN,
(b) —NO$_2$,
(c) —CO$_2$R$^{11}$,

R$^5$ is
(a) H,
(b) C$_1$–C$_6$ alkyl,
(c) C$_3$–C$_6$ cycloalkyl,
(d) C$_2$–C$_4$ alkenyl,
(e) C$_2$–C$_4$ alkynyl;

R$^6$ is
(a) C$_1$–C$_{10}$ alkyl,
(b) C$_3$–C$_8$ alkenyl,
(c) C$_3$–C$_8$ alkynyl,
(d) C$_3$–C$_8$ cycloalkyl,
(e) C$_4$–C$_8$ cycloalkenyl,
(f) C$_4$–C$_{10}$ cycloalkylalkyl,
(g) C$_5$–C$_{10}$ cycloalkylalkenyl,
(h) C$_5$–C$_{10}$ cycloalkylalkynyl,
(i) —(CH$_2$)SZ(CH$_2$)$_m$R$^5$,
(j) phenyl, optionally substituted with 1–2 substituents selected from the group of halo, C$_1$–C$_4$ alkyl, C$_1$–C$_4$ alkoxy, —NO$_2$, —NH$_2$, —OH and benzyloxy,
(k) benzyl, optionally substituted on the phenyl ring with 1–2 substituents selected from the group of halo, C$_1$–C$_4$ alkyl, C$_1$–C$_4$ alkoxy and —NO$_2$;

R$^7$ and R$^8$ taken together are —(CH$_2$)$_t$—,
R$^9$ and R$^{10}$ taken together are O;

R$^{11}$ is
(a) H,
(b) C$_1$–C$_4$ alkyl,
(c) C$_1$–C$_4$ cycloalkyl,
(d) phenyl,
(e) benzyl;

R$^{12}$ is
(a) H,
(b) methyl,
(c) benzyl;

R$^{13}$ is
(a) —CH$_2$CO$_2$H,
(b) —C(CF$_3$)$_2$OH,
(c) —CONHNHSO$_2$CF$_3$,
(d) —CONHOR$^{12}$,
(e) —CONHSO$_2$R$^{20}$,
(f) —CONHSO$_2$NHR$^{19}$,
(g) —C(OH)R$^{19}$PO$_3$H$_2$,
(h) —NHCONHSO$_2$R$^{20}$,
(i) —NHPO$_3$H$_2$,
(j) —SO$_2$NHCOR$^{20}$,
(k) —OPO$_3$H$_2$,
(l) —OSO$_3$H,
(m) —PO(OH)R$^{19}$,
(n) —PO$_3$H$_2$,
(o) —SO$_3$H,
(p) —SO$_2$NHR$^{19}$,
(q) —NHSO$_2$NHCOR$^{20}$,
(r) —SO$_2$NHCONHR$^{19}$,

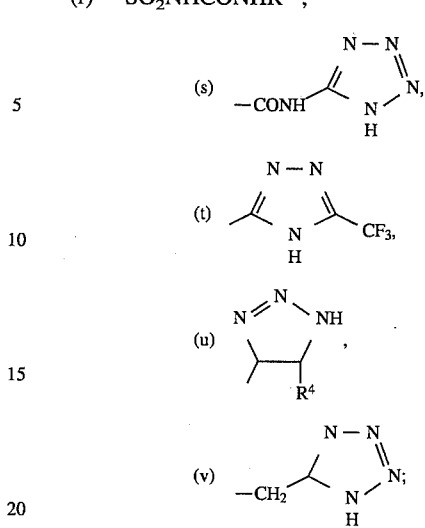

R$^{19}$ is
(a) H,
(b) C$_1$–C$_5$ alkyl optionally substituted with a substituent selected from the group consisting of aryl, as defined above, —OH, —SH, C$_1$–C$_4$ alkyl, C$_1$–C$_4$ alkoxy, C$_1$–C$_4$ alkylthio, —CF$_3$, halo, —NO$_2$, —CO$_2$H, —CO$_2$CH$_3$, —CO$_2$-benzyl, —NH$_2$, C$_1$–C$_4$ alkylamino, C$_1$–C$_4$ dialkylamino, —PO$_3$H$_2$,
(c) aryl, as defined above,
(d) benzyl R$^{20}$ is
(a) aryl, as defined above,
(b) C$_3$–C$_7$ cycloalkyl,
(c) C$_1$–C$_4$ perfluoroalkyl,
(d) C$_1$–C$_4$ alkyl optionally substituted with a substituent selected from the group consisting of aryl, as defined above, —OH, —SH, C$_1$–C$_4$ alkyl, C$_1$–C$_4$ alkoxy, C$_1$–C$_4$ alkylthio, —CF$_3$, halo, —NO$_2$, —CO$_2$H, —CO$_2$CH$_3$, —CO$_2$-benzyl, —NH$_2$, C$_1$–C$_4$ alkylamino, C$_1$–C$_4$ dialkylamino, —PO$_3$H$_2$,
(e) C$_1$–C$_4$ alkoxy optionally substituted with a substituent selected from the group consisting of aryl as defined above, —OH, —SH, C$_1$–C$_4$ alkyl, C$_1$–C$_4$ alkoxy, C$_1$–C$_4$ alkylthio, —CF$_3$, halo, —NO$_2$, —CO$_2$H, —CO$_2$CH$_3$, —CO$_2$-benzyl, —NH$_2$, C$_1$–C$_4$ alkylamino, C$_1$–C$_4$ dialkylamino, —PO$_3$H$_2$,
(f) furyl;
(g) thienyl;

R$^{21}$ is
(a) H,
(b) C$_1$–C$_6$ alkyl,
(c) phenyl,
(d) benzyl;

Z is
(a) —O—,
(b) —S—,
(c) —NR$^{11}$—;

m is 1 to 5;
n is 1 to 4;
t is 2 to 5;
or a pharmaceutically acceptable salt thereof.

2. A compound of claim 1 wherein $R^1$ is in the para position and is

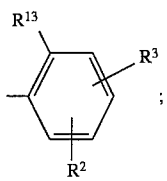

$R^6$ is
(a) $C_1$–$C_{10}$ alkyl,
(b) $C_3$–$C_{10}$ alkenyl,
(c) $C_3$–$C_{10}$ alkynyl,
(d) $C_3$–$C_8$ cycloalkyl,
(e) phenyl, optionally substituted with 1–2 substituents selected from the group of halo, $C_1$–$C_4$ alkyl, $C_1$–$C_4$ alkoxy, —$NO_2$, —$NH_2$, —OH and benzyloxy,
(f) benzyl, optionally substituted on the phenyl ring with one or two substituents selected from the group consisting of halo, $C_1$–$C_4$ alkyl, $C_1$–$C_4$ alkoxy and —$NO_2$;
$R^7$ and $R^8$ taken together are —$(CH_2)_4$—,
$R^9$ and $R^{10}$ taken together are O;
$R^{13}$ is
(a) —$CONHSO_2R^{20}$;
(b) —$NHCONHSO_2R^{20}$,
(c) —$NHSO_2NHCOR^{20}$,
(d) —$PO_3H_2$,
(e) —$SO_3H$,
(f) —$SO_2NHR^{19}$,
(g) —$SO_2NHCOR^{20}$,
(h) —$SO_2NHCONHR^{19}$,
(i)

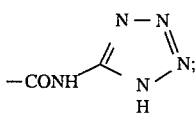

or a pharmaceutically acceptable salt thereof.
3. A compound of claim 2 wherein
$R^6$ is
(a) $C_1$–$C_7$ alkyl,
(b) $C_3$–$C_4$ alkenyl,
(c) $C_3$–$C_4$ alkynyl,
(d) phenyl, optionally substituted with 1–2 substituents selected from the group of halo, $C_1$–$C_4$ alkyl, $C_1$–$C_4$ alkoxy, —$NO_2$, —$NH_2$, —OH and benzyloxy;
$R^{13}$ is
(a) —$CONHSO_2R^{20}$,
(b) —$NHCONHSO_2R^{20}$,
(c) —$SO_2NHR^{19}$,
(d) —$SO_2NHCONHR^{19}$,
(e) —$SO_2NHCOR^{20}$,
(f) —$SO_2NHCONHR^{19}$;

or a pharmaceutically acceptable salt thereof.
4. A compound of claim 3 wherein $R^1$ is

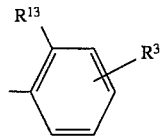

or a pharmaceutically acceptable salt thereof.
5. A compound of claim 4 selected from the group consisting of
N-[4'-[[4-oxo-2-butyl-1,3-diazaspiro[4.4]non-1-en-3 -yl]methyl](1,1'-biphenyl-2-ylsulfonyl)]-benzamide
N-[4'-[[4-oxo-2-butyl-1,3-diazaspiro[4.4]non-1-en-3-yl]methyl](1,1'-biphenyl-2-ylsulfonyl)]-benzamide
N-[4'-[[4-oxo-2-propyl-1,3-diazaspiro[2.4]hept-1-en-3-yl]methyl] (1,1'-biphenyl-2-ylsulfonyl)]-hexanamide
N-[4'-[[4-oxo-2-propyl-1,3-diazaspiro[4.4]non-1-en-3-yl]methyl](1,1'-biphenyl-2-ylsulfonyl)]-hexanamide
N-[4'-[[4-oxo-2-propyl-1,3-diazaspiro[4.5]dec-1-en-3-yl]methyl](1,1'-biphenyl-2-ylsulfonyl)]-hexanamide
N-[4'-[[4-oxo-2-butyl-1,3-diazaspiro[4.4]non-1-en-3 -yl]methyl](1,1'-biphenyl-2-ylsulfonyl)]-hexanamide
N-[4'-[[4-oxo-2-propyl-1,3-diazaspiro[4.4]non-1-en-3-yl]methyl][(3-chloro-(1,1'-biphenyl-2-ylsulfonyl)] ]-carbamic acid, n-butyl ester
N-[4'-[[4-oxo-2-propyl-1,3-diazaspiro[4.4]non-1-en-3-yl]methyl](1,1'-biphenyl-2-ylsulfonyl)]-carbamic acid, 2-methylpropyl ester
N-[4'-[[4-oxo-2-propyl-1,3-diazaspiro[4.4]non-1-en-3-yl]methyl][3'-methyl (1,1'-biphenyl-2-ylsulfonyl)] ]-carbamic acid, n-butyl ester
N-[4'-[[4-oxo-2-propyl-1,3-diazaspiro[4.4]non-1-en-3-yl]methyl][4-propyl(1,1'-biphenyl-2-ylsulfonyl)]]carbamic acid, n-butyl ester.
6. A pharmaceutical composition comprising a pharmaceutically suitable carrier and a compound of any one of claims 1 through 4.
7. A pharmaceutical composition comprising a pharmaceutically suitable carrier and a compound of claim 5.
8. A method of treating hypertension in a warm blooded animal comprising administering to an animal in need of such treatment an effective mount of a compound of any one of claims 1 through 4.
9. A method of treating hypertension in a warm blooded animal comprising administering to an animal in need of such treatment an effective amount of a compound of claim 5.
10. A method of treating congestive heart failure in a warm blooded animal comprising administering to an animal in need of such treatment an effective amount of a compound of any of one claims 1 through 4.
11. A method of treating congestive heart failure in a warm blooded animal comprising administering to an animal in need of such treatment effective of a compound of claim 5.

* * * * *